(12) United States Patent
Shannon et al.

(10) Patent No.: US 10,973,790 B2
(45) Date of Patent: Apr. 13, 2021

(54) EFLORNITHINE AND SULINDAC, FIXED DOSE COMBINATION FORMULATION

(71) Applicant: Cancer Prevention Pharmaceuticals, Inc., Tucson, AZ (US)

(72) Inventors: Patrick Shannon, Pensacola, FL (US); Roberto Carlos Bravo González, Binningen (CH); Jean Ducassou, Cestas (FR)

(73) Assignee: CANCER PREVENTION PHARMACEUTICALS, INC., Tucson, AZ (US)

( * ) Notice: Subject to any disclaimer, the term of this patent is extended or adjusted under 35 U.S.C. 154(b) by 106 days.

(21) Appl. No.: 15/771,484

(22) PCT Filed: Oct. 31, 2016

(86) PCT No.: PCT/US2016/059689
§ 371 (c)(1),
(2) Date: Apr. 27, 2018

(87) PCT Pub. No.: WO2017/075576
PCT Pub. Date: May 4, 2017

(65) Prior Publication Data
US 2020/0009098 A1 Jan. 9, 2020

Related U.S. Application Data

(60) Provisional application No. 62/248,810, filed on Oct. 30, 2015, provisional application No. 62/358,698, filed on Jul. 6, 2016.

(30) Foreign Application Priority Data

Oct. 28, 2016 (EP) ..................................... 16306429
Oct. 28, 2016 (EP) ..................................... 16306430

(51) Int. Cl.
*A61K 31/198* (2006.01)
*A61K 9/20* (2006.01)
(Continued)

(52) U.S. Cl.
CPC .......... *A61K 31/198* (2013.01); *A61K 9/2009* (2013.01); *A61K 9/2013* (2013.01);
(Continued)

(58) Field of Classification Search
None
See application file for complete search history.

(56) References Cited

U.S. PATENT DOCUMENTS

| 4,309,442 A | 1/1982 | Bey |
| 4,330,559 A | 5/1982 | Bey et al. |

(Continued)

FOREIGN PATENT DOCUMENTS

| CA | 2 165 481 | 1/1995 |
| CN | 101898978 | 12/2010 |

(Continued)

OTHER PUBLICATIONS

Li et al., "Lubricants in Pharmaceutical Solid Dosage Forms", Lubricants 2014, 2, 21-43 . (Year: 2014).*

(Continued)

*Primary Examiner* — Kyung S Chang
(74) *Attorney, Agent, or Firm* — Parker Highlander PLLC

(57) ABSTRACT

Provided herein are fixed-dose combination formulations of a pharmaceutically effective amount of eflornithine together with a pharmaceutically effective amount of sulindac. Also provided are methods of use and of methods of manufacture of these formulations.

23 Claims, 7 Drawing Sheets

| Product | Conditions | Packaging | T6 M | T0 |
|---|---|---|---|---|
| Eflornithine/ Sulindac 375mg/75mg | 25°C/75% HR | Closed bottles | 6,0 | 6,1 |
| | 30°C/65% HR | Closed bottles | 6,0 | |
| | 40°C/75% HR | Opened bottles | 6,4 | |
| | 40°C/75% HR | Closed bottles | 6,2 | |
| Eflornithine 250mg | 25°C/75% HR | Closed bottles | 6,9 | 6,5 |
| | 30°C/65% HR | Closed bottles | 7,1 | |
| | 40°C/75% HR | Opened bottles | 7,5 | |
| | 40°C/75% HR | Closed bottles | 7,3 | |
| Sulindac 150mg | 25°C/75% HR | Closed bottles | 2,9 | 2,9 |
| | 30°C/65% HR | Closed bottles | 3,2 | |
| | 40°C/75% HR | Opened bottles | 3,5 | |
| | 40°C/75% HR | Closed bottles | 3,2 | |

(51) Int. Cl.
  *A61K 9/28* (2006.01)
  *A61K 31/192* (2006.01)
  *A61K 45/06* (2006.01)
  *A61P 25/00* (2006.01)
  *A61P 17/00* (2006.01)
  *A61P 1/00* (2006.01)
  *A61P 35/00* (2006.01)

(52) U.S. Cl.
  CPC .......... *A61K 9/2054* (2013.01); *A61K 9/2095* (2013.01); *A61K 9/2813* (2013.01); *A61K 9/2853* (2013.01); *A61K 9/2866* (2013.01); *A61K 31/192* (2013.01)

(56) References Cited

U.S. PATENT DOCUMENTS

| | | |
|---|---|---|
| 4,413,141 A | 11/1983 | Bey et al. |
| 4,499,072 A | 2/1985 | Sunkara |
| 4,859,452 A | 8/1989 | Ajani et al. |
| 4,925,835 A | 5/1990 | Heston |
| 5,002,879 A | 3/1991 | Bowlin |
| 5,814,625 A | 9/1998 | Larson et al. |
| 5,843,929 A | 12/1998 | Larson et al. |
| 6,258,845 B1 | 7/2001 | Gerner et al. |
| 6,573,290 B1 | 6/2003 | Love |
| 6,602,910 B2 | 8/2003 | Levenson |
| 6,753,422 B2 | 6/2004 | O'Brien et al. |
| 7,273,888 B2 | 9/2007 | Ramesh |
| 7,592,319 B2 | 9/2009 | Li et al. |
| 8,329,636 B2 | 12/2012 | Gerner et al. |
| 9,072,778 B2 | 7/2015 | Bachmann |
| 9,121,852 B2 | 9/2015 | Gerner et al. |
| 9,937,141 B2 | 4/2018 | Gerner et al. |
| 2002/0081611 A1 | 6/2002 | O'Brien |
| 2002/0098161 A1 | 7/2002 | Uhrich |
| 2002/0110590 A1* | 8/2002 | Shaked ............... A61K 9/2081 424/469 |
| 2005/0032726 A1 | 2/2005 | Li et al. |
| 2005/0037090 A1 | 2/2005 | McKearn et al. |
| 2005/0059690 A1 | 3/2005 | Newman et al. |
| 2010/0120727 A1 | 5/2010 | Xu |
| 2010/0197718 A1 | 8/2010 | Pisano et al. |
| 2010/0317708 A1 | 12/2010 | Gerner et al. |
| 2011/0158983 A1 | 6/2011 | Bascomb et al. |
| 2011/0256161 A1 | 10/2011 | Burns et al. |
| 2012/0259013 A1 | 10/2012 | Motwani et al. |
| 2013/0137746 A1* | 5/2013 | Govek ............... A61K 9/0014 514/428 |
| 2013/0157972 A1 | 6/2013 | Cheng |
| 2013/0164751 A1 | 6/2013 | Gerner et al. |
| 2013/0216528 A1 | 8/2013 | Cheung et al. |
| 2013/0217743 A1 | 8/2013 | Raj et al. |
| 2015/0301060 A1 | 10/2015 | Gerner et al. |
| 2016/0213634 A1 | 7/2016 | Gerner et al. |
| 2017/0362658 A1 | 12/2017 | Gerner et al. |

FOREIGN PATENT DOCUMENTS

| | | |
|---|---|---|
| EP | 2 438 919 | 4/2012 |
| JP | 2002-509884 | 4/2002 |
| JP | 2002-533416 | 10/2002 |
| JP | 2012-511052 | 5/2012 |
| WO | WO 2016/130918 | 8/1916 |
| WO | WO 99/49859 | 10/1999 |
| WO | WO 2000-37107 | 6/2000 |
| WO | WO 01/68076 | 9/2001 |
| WO | WO 02/15895 | 2/2002 |
| WO | WO 2009/048932 | 4/2009 |
| WO | WO 2010/056919 | 5/2010 |
| WO | WO 2010/132817 | 11/2010 |
| WO | WO 2011/135459 | 11/2011 |
| WO | WO 2014-070767 | 5/2014 |
| WO | WO 2014/140072 | 9/2014 |
| WO | WO 2015-195120 | 12/2015 |

OTHER PUBLICATIONS

Office Communication issued in corresponding Taiwanese Application No. 105135187, dated Oct. 30, 2019. (English translation appended).
Stahl, "Preventing Tablet Capping", URL: <https://www.gea.com/en/stories/preventing-tablet-capping.jsp>, 2014.
"NCT01245816" dated Apr. 23, 2015, retrieved from clinicaltrials.gov archive on Jan. 20, 2017.
"NCT01483144" dated Jul. 28, 2015, retrieved from clinicaltrials.gov archive on Jan. 20, 2017.
"NCT01483144" updated Sep. 27, 2018, retrieved from clinicaltrials.gov on Feb. 4, 2019.
"NCT00003076" updated Dec. 19, 2012, retrieved from clinicaltrials.gov on Feb. 4, 2019.
"NCT00003814" updated Dec. 18, 2013, retrieved from clinicaltrials.gov on Feb. 5, 2019.
"NCT00005882" updated Feb. 19, 2015, retrieved from apps.who.int on Feb. 5, 2019.
"NCT00005884" updated Oct. 2, 2015, retrieved from clinicaltrials.gov on Feb. 5, 2019.
"NCT00006079" updated Oct. 25, 2018, retrieved from clinicaltrials.gov on Feb. 4, 2019.
"NCT00006101" updated May 14, 2018, retrieved from clinicaltrials.gov on Feb. 5, 2019.
"NCT00021294" updated Sep. 11, 2018, retrieved from clinicaltrials.gov on Feb. 5, 2019.
"NCT00033371" updated Feb. 15, 2017, retrieved from clinicaltrials.gov on Feb. 4, 2019.
"NCT00086736" updated Nov. 19, 2013, retrieved from clinicaltrials.gov on Feb. 4, 2019.
"NCT00118365" updated Jan. 22, 2015, retrieved from clinicaltrials.gov on Feb. 4, 2019.
"NCT00146627" updated Sep. 29, 2016, retrieved from clinicaltrials.gov on Feb. 4, 2019.
"NCT00152048" updated Jun. 9, 2014, 2018, retrieved from clinicaltrials.gov on Feb. 4, 2019.
"NCT00176995" updated Nov. 13, 2006, retrieved from clinicaltrials.gov on Feb. 4, 2019.
"NCT00204789" updated Oct. 2, 2015, retrieved from clinicaltrials.gov on Feb. 5, 2019.
"NCT00330148" updated May 26, 2006, retrieved from clinicaltrials.gov on Feb. 5, 2019.
"NCT00489658" updated Jun. 21, 2007, retrieved from clinicaltrials.gov on Feb. 4, 2019.
"NCT00601640" updated Mar. 23, 2017, retrieved from clinicaltrials.gov on Feb. 4, 2019.
"NCT00906880" updated May 31, 2013, retrieved from clinicaltrials.gov on Feb. 4, 2019.
"NCT00983580" updated Apr. 30, 2018, retrieved from clinicaltrials.gov on Feb. 4, 2019.
"NCT01059071" updated Oct. 2, 2018, retrieved from clinicaltrials.gov on Feb. 4, 2019.
"NCT01349881" updated Dec. 21, 2018, retrieved from clinicaltrials.gov on Feb. 4, 2019.
"NCT01586260" updated Jul. 10, 2018, retrieved from clinicaltrials.gov on Feb. 4, 2019.
"NCT01636128" updated Jul. 30, 2014, retrieved from clinicaltrials.gov on Feb. 4, 2019.
"NCT01685827" updated Feb. 20, 2018, retrieved from clinicaltrials.gov on Feb. 4, 2019.
"NCT01817894" updated Dec. 2, 2013, retrieved from clinicaltrials.gov on Feb. 5, 2019.
"NCT02030964" updated Nov. 20, 2018, retrieved from clinicaltrials.gov on Feb. 5, 2019.
"NCT02139397" updated Jul. 10, 2018, retrieved from clinicaltrials.gov on Feb. 5, 2019.
"NCT02384889" updated Aug. 16, 2018, retrieved from clinicaltrials.gov on Feb. 5, 2019.
"NCT02395666" updated Jul. 10, 2018, retrieved from clinicaltrials.gov on Feb. 5, 2019.

(56) References Cited

OTHER PUBLICATIONS

"VANIQA®" (eflornithine hydrochloride) Prescription Information, dated Jul. 2010.
Alberts et al., "Do NSAIDs exert their colon cancer chemoprevention activities through the inhibition of mucosal prostaglandin synthetase?," *J. Cell. Biochem. Supp.*, (22):18-23, 1995.
Arber et al., "A K-ras oncogene increases resistance to sulindac-induces apoptosis in rat enterocytes," Gastroenterology, 113: 1892-1990, 1997.
Babbar et al., "Induction of spermidine/spermine N1-acetyltransferase (SSAT) by aspirin in Caco-2 colon cancer cells," *Biochem. J.*, 394:317-24, 2006.
Bachrach et al., "Polyamines: new cues in cellular signal transduction," *News Physiol. Sci.*, 16:106-109, 2001.
Barry et al., "Ornithine decarboxylase polymorphism modification of response to aspirin treatment for colorectal adenoma prevention," *J. Natl. Cancer Inst.*, 98(20):1494-500, 2006.
Basuroy and Gerner, "Emerging concepts in targeting the polyamine metabolic pathway in epithelial cancer chemoprevention and chemotherapy," *J. Biochem.*, 139(1):27-33, 2006.
Bedi et al., "Inhibition of apoptosis during development of colorectal cancer," *Cancer Res.*, 55(9):1811-1816, 1995.
Bello-Fernandez et al., "The ornithine decarboxylase gene is a transcriptional target of c-Myc," *Proc. Natl. Acad. Sci. USA*, 90:7804-8, 1993.
Boolbol et al., "Cyclooxygenase-2 overexpression and tumor formation are blocked by sulindac in a mutine model of familial adenomatous polyposis," *Cancer Research*, 56:2556-2560, 1996.
Boone et al., "Biomarker end-points in cancer chemoprevention trails," IARC Scientific Publications, 142:273-280, 1997.
Boyle et al., "Polyamine contents in rectal and buccal mucosae in humans treated with oral difluoromethylornithine," *Cancer Epidemiol. Biomarkers Prev.*, 1: 131-135, 1992.
Brabender et al., "Upregulation of ornithine decarboxylase mRNA expression in Barrett's esophagus and Barrett's-associated adenocarcinoma," *J. Gastrointest. Surg.*, 5:174-181; discussion 182, 2001.
Braverman et al., "Ornithine decarboxylase: an unreliable marker for the identification of population groups at risk for colonic neoplasia," Am. J. Gastronenterology, 85:723-726, 1990.
Castel et al., "Treatment of high-risk neuroblastoma with anti-GD2 antibodies," Clinical and Translational Oncology, 12:788-793, 2010.
Childs et al., "Polyamine-dependent gene expression," *Cell. Molec. Life Sci.*, 60:1394-1406, 2003.
Croghan et al., "Dose-related alpha-difluoromethylornithine ototoxicity," Am. J. Clin. Oncol., (14):331-5, 1991.
Declaration submitted in U.S. Appl. No. 13/709,753, dated Mar. 10, 2015.
Derynck et al., "TGF-beta signaling in tumor suppression and cancer progression," *Nature Genetics*, 29:117-29, 2001.
DuBois et al., "G1 delay in cells overexpressing prostaglandin endoperoxide synthase-2," *Cancer Res.*, 56:733-737, 1996.
Erdman et al., "Assessment of Mutations in Ki-ras and P53 in colon cancers from azoxymethane-and dimethylhydrazine-treated rats," Mol. Carcin., (19):137-144, 1997.
Erdman et al., "APC-dependent changes in expression of genes influencing polyamine metabolism, and consequences for gastrointestinal carcinogenesis, in the Min mouse," *Carcinogenesis*, 20(9):1709-13, 1999.
Extended European Search Report issued in European Patent Application No. 10775626.4, dated Feb. 4, 2013.
Fearon et al., "A genetic model for colorectal tumorigenesis," *Cell*, 61:759-767, 1990.
Fultz and Gerner, "APC-dependent regulation of ornithine decarboxylase in human colon tumor cells," *Mol. Carcinog.*, 34:10-8, 2002.
Gamble et al., "Polyamine pathway inhibition as a novel therapeutic approach to treating neuroblastoma," Frontier in Oncology, 2(162):1-10, 2012.
Gann et al., "Low-dose aspirin and incidence of colorectal tumors in a randomized trial," *J. Natl. Cancer Inst.*, 85:1220-1224, 1993.

Gerner and Meyskens, "Polyamines and cancer: old molecules, new understanding," *Nature Rev. Cancer*, 4:781-92, 2004.
Gerner et al., "Combination chemoprevention for colon cancer targeting polyamine synthesis and inflammation," *Clinical Cancer Research*, 15(3):758-761, 2009.
Gerner et al., "Gastrointestinal tissue polyamine contents of patients with Barrett's esophagus treated with alpha-difluoromethylornithine," *Cancer Epidemiol. Biomarkers Prev.*, 3:325-330, 1994.
Gerner, "Impact of dietary amino acids and polyamines on intestinal carcinogenesis and chemoprevention in mouse models," *Biochemical Society Transactions*, 35(2):322-325, 2007.
Gerner. E. W., et al. "Rationale for, and design of, a clinical trial targeting polyamine metabolism for colon cancer chemoprevention." *Amino acids* 33.2 (2007): 189-195.
Giardiello et al., "Ornithine decarboxylase and polyamines in familial adenomatous polyposis," *Cancer Res.*, (57):199-201, 1997.
Greenberg et al., "Reduced risk of large bowel adenomas among aspirin users," *J. Natl. Cancer Inst.*, 85:912-916, 1993.
Guo et al., "Functional analysis of human ornithine decarboxylase alleles," *Cancer Res.*, 60(22):6314-6317, 2000.
Hanif et al., "Effects of nonsteroidal anti-inflammatory drugs on proliferation and on induction of apoptosis in colon cancer cells by a prostaglandin-independent pathway," *Biochemical Pharmacology*, (52):237-245, 1996.
Hessels et al., "Microbial flora in the gastrointestinal tract abolishes cytostatic effects of α-difluoromethylornithine in vivo," *Int. J. Cancer*, 43: 1155-1164, 1989.
Hixson et al., "Ornithine decarboxylase and polyamines in colorectal neoplasia and mucosa," *Cancer Epidemiology Biomarkers Prev.*, 2:369-374, 1993.
Hixson et al., "Sources of variability in measurements of ornithine decarboxylase activity and polyamine contents in colorectal mucosa," *Cancer Epidemoil. Biomarkers Prev.*, 3:317-323, 1994.
Hogarty et al., "ODC1 is a critical determinant of MYCN oncogenesis and a therapeutic target in neuroblastoma," Cancer Res., 68:9735-9745, 2008.
Hubner et al., "Ornithine decarboxylase G316A genotype is prognostic for colorectal adenoma recurrence and predicts efficacy of aspirin chemoprevention," *Clin. Cancer Res.*, 14(8):2303-9, 2008.
Hughes, et al., "Polyarnines reverse non-steroidal anti-inflammatory drug-induced toxicity in human colorectal cancer cells", Biochem J, 374:481-8, 2003.
Ignatenko et al., "Dietary putrescine reduces the intestinal anticarcinogenic activity of sulindac in a mutine model of familial adenomatous polyposis," *Nutrition and Cancer*, 56(2): 172-181, 2006.
Ignatenko et al., "Role of c-Myc in intestinal tumorigenesis of the ApcMin/+ mouse," *Cancer Biol. Ther.*, 5(12):1658-64, 2006.
Iwamoto et al., "Expression of beta-catenin and full-length APC protein in normal and neoplastic colonic tissues," *Carcinogenesis*, 21:1935-40, 2000.
Jass et al., "Emerging concepts in colorectal neoplasia," *Gastroenterology*, 123:862-876, 2002.
Johnson et al. "Relationships between drug activity in NCI preclinical in vitro and in vivo models and early clinical trials." *British Journal of Cancer* 84.10 (2001): 1424.
Kawamori et al., "Chemopreventive activity of celecoxib, a specific cyclooxygenase-2 inhibitor, against colon carcinogenesis," *Cancer Research*, 58:409-412, 1998.
Kelloff et al., "Chemopreventive drug development: perspectives and progress," *Cancer Epidemiology Biomarks and Prevention*, 3:85-98, 1994.
Kelloff et al., "New agents for cancer chemoprevention," *J. Cell. Biochem.*, 265:1-28, 1996.
Kelloff et al., "Perspectives on chemoprevention agent selection and short term clinical prevention trials," *European J. Cancer Prevention*, 5(Supp. 2):79-85, 1996.
Kingsnorth et al., "Effects of alpha-difluoromethylornithine and 5-fluorouracil on the proliferation of a human colon adenocarcinoma cell line," *Cancer Res.*, 43(9):4035-8, 1983.
Kruh et al., "Expression Pattern of MRP in Human Tissues and Adult Solid Tumor Cell Lines," *J. Natl. Cancer Inst.*, 87(16):1256-1258, 1995.

(56) References Cited

OTHER PUBLICATIONS

Ladenheim et al., "Effect of sulindac on sporadic colonic polyps," *Gastroenterology*, 108:1083-1087, 1995.

Lanza et al., "Peptic ulcer and gastrointestinal hemorrhage associated with nonsteroidal anti-inflammatory drug use in patients younger than 65 years. A large health maintenance organization cohort study," *Arch. Intern. Med.*, 155:1371-1377, 1995.

Le et al., "Effects of socioeconomic status and treatment disparities in colorectal cancer survival," *Cancer Epidemiol. Biomarkers Prev.*, 17:1950-62, 2008.

Levin et al., "Relationship between ornithine decarboxylase levels in anaplastic gliomas and pregression-free survival in patients treated with DFMO-PCV chemotherapy," *International Journal of Cancer*, 121:(10): 2279-2283, 2010.

Linsalata et al., "Nutritional factors and polyamine metabolism in colorectal cancer," *Nutrition*, 24:382-389, 2008.

Lipkin, "New rodent models for studies of chemopreventive agents," *J. Cell Biochem. Suppl.*, 28-29:144-7, 1997.

Love et al., "Randomized phase I chemoprevention dose-seeking study of alpha-difluoromethylornithine," *J. Natl. Cancer Inst.*, 85:732-7, 1993.

Lozier et al., "Targeting ornithine decarboxylase reverses the LIN28/Let-7 axis and inhibits glycolytic metabolism in neuroblastoma," *Oncotarget*, 6:196-206, 2015.

Luk and Baylin, "Ornithine decarboxylase as a biologic marker in familial colonic polyposis," *N. Engl. J. Med.*, 311(2):80-83, 1984.

Lupulescu, "Control of precancer cell transformation into cancer cells: its relevance to cancer prevention," *Cancer Detect. Prev.*, 20(6):634-637, 1996.

Mackenzie, Gerardo G., et al. "Phospho-sulindac (OXT-328) combined with difluoromethylornithine prevents colon cancer in mice." Cancer prevention research 4.7 (2011): 1052-1060.

Martinez et al., "Pronounced reduction in adenoma recurrence associated with aspirin use and a polymorphism in the ornithine decarboxylase gene," *Proc. Natl. Acad. Sci. USA*, 100:7859-64, 2003.

Matsubara et al., "Association between high levels of ornithine decarboxylase activity and favorable prognosis in human colorectal carcinoma," *Clinical Cancer Res.*, 1:665-71, 1995.

McGarrity et al., "Colonic polyamine content and ornithine decarboxylase activity as markers for adenomas," *Cancer*, 66:1539-1543, 1990.

McLaren et al., "Longitudinal assessment of air conduction audiograms in a phase III clinical trial of difluoromethylornithine and sulindac for prevention of sporadic colorectal adenomas," *Cancer Prev. Res.*, 1(7):514-21, 2008.

Meyskens and Gerner, "Development of difluoromethylornithine as a chemoprevention agent for the management of colon cancer," *J. Cell. Biochem.*, 22:126-131, 1995.

Meyskens et al., "Development of difluoromethylornithine (DFMO) as a chemoprevention agent," *Clin. Cancer Res.*, 5:945-951, 1999.

Meyskens et al., "Difluoromethylornithine plus sulindac for the prevention of sporadic colorectal adenomas: a randomized placebo-controlled, double-blind trial," *Cancer Prev. Res.*, 1(1):32-8, 2008.

Meyskens et al., "Dose de-escalation chemoprevention trial of alpha-difluoromethylornithine in patients with colon polyps," *J. Natl. Cancer Inst.*, 86(15):1122-1130, 1994.

Meyskens et al., "Effect of alpha-difluoromethylornithine on rectal mucosal levels of polyamines in a randomized, double-blinded trial for colon cancer prevention," *J. Natl. Cancer Inst.*, 90(16):1212-8, 1998.

Muscat et al., "Nonsteroidal antiinflammatory drugs and colorectal cancer," *Cancer*, 74:1847-1854, 1994.

Nishimura et al., "Independent roles of eIF5A and polyamines in cell proliferation," Biochem. J., 385:779-785, 2005.

O'Brien et al., "Differences in ornithine decarboxylase and androgen receptor allele frequencies among ethnic groups," *Molec. Carcinog.*, 41(2):120-3, 2004.

Office Communication issued in U.S. Appl. No. 12/780,592, dated Aug. 14, 2012.

Office Communication issued in U.S. Appl. No. 13/709,753, dated Sep. 10, 2014.

Office Communication issued in U.S. Appl. No. 13/709,753, dated Apr. 21, 2015.

Office Communication issued in U.S. Appl. No. 14/841,750, dated Apr. 21, 2017.

Office Communication issued in U.S. Appl. No. 14/841,750, dated Nov. 24, 2017.

Office Communication issued in U.S. Appl. No. 15/319,857, dated Sep. 13, 2018.

Office Communication issued in U.S. Appl. No. 12/780,592, dated Mar. 20, 2012.

Pardali and Moustakas, "Actions of TGF-beta as tumor suppressor and pro-metastatic factor in human cancer," *Biochimica et Biophysica Acta*, 1775 :21-62, 2007.

Pasricha et al., "The effects of sulindac on colorectal proliferation and apoptosis in familial adenomatous polyposis," *Gastroenterology*, 109:994-998, 1995.

Paz et al., "Polyamines are oncometabolites that regulate the LIN28/let-7 pathway in colorectal cancer cells," Molecular Carcinogensis, 2013.

PCT International Search Report and Written Opinion, issued in International Application No. PCT/US2016/059689, dated Jan. 31, 2017.

Peel et al., "Characterization of hereditary nonpolyposis colorectal cancer families from a population-based series of cases," *J. Natl. Cancer Inst.*, 92:1517-22, 2000.

Pegg, "Recent advances in the biochemistry of polyamines in eukaryotes," *Biochem.*, 234(2):249-262, 1986.

Piazza et al., "Antineoplastic drugs sulindac sulfide and sulfone inhibit cell growth by inducing apoptosis," *Cancer Res.*, (55):3110-3116, 1995.

Piazza et al., "Apoptosis primarily accounts for the growth-inhibitory properties of sulindac metabolites and involves a mechanism that is independent of cyclooxygenase inhibition, cell cycle arrest, and p53 induction," *Cancer Res.*, (57):2452-2459, 1997a.

Piazza et al., "Sulindac sulfone inhibits azoxymethane-induced colon carcinogenesis in rats without reducing prostaglandin levels," *Cancer Res.*, (57):2909-2915, 1997b.

Pollard and Luckert, "Prevention and treatment of primary intestinal tumors in rats by piroxicam,"*Cancer Res.*, 49:6471-6473, 1989.

Porter et al., "Polyamine biosynthetic activity in normal and neoplastic human colorectal tissue," *Cancer*, 60:1275-1281, 1987.

Quemener et al., "Polyamine deprivation: a new tool in cancer treatment," *Institute of Anticancer Research*, 14:443-448, 1994.

Raj et al., "Role of dietary polyamines in a phase III clinical trial of difluoromethylornithine (DFMO) and sulindac for prevention of sporadic colorectal adenomas," *British Journal of Cancer*, 108(3):512-518, 2013.

Rao et al., "Chemoprevention of colon carcinogenesis by sulindac, a nonsteroidal anti-inflammatory agent," *Cancer Res.*, (55):1464-1472, 1995.

Reddy et al., "Chemoprevention of colon carcinogenesis by concurrent administration of piroxicam, a nonsteroidal antiinflammatory drug with D,L-alpha-difluoromethylornithine, an ornithine decarboxylase inhibitor, in diet," *Cancer Research*, 50:2562-2568, 1990.

Reddy et al., "Dose-related inhibition of colon carcinogenesis by dietary piroxicam, a nonsteroidal antiinflammatory drug, during different stages of rat colon tumor development," *Cancer Res.*, 47:5340-5346, 1987.

Rial, Nathaniel S., Frank L. Meyskens, and Eugene W. Gerner. "Polyamines as mediators of APC-dependent intestinal carcinogenesis and cancer chemoprevention." Essays in biochemistry 46 (2009): 111-124.

Roberts and Wakefield, "The two faces of transforming growth factor beta in carcinogenesis," *Proc. Natl. Acad. Sci. USA*, 100:8621-3, 2003.

Rounbehler et al., "Targeting ornithine decarboxylase impairs development of MYCN-amplified neuroblastoma," Cancer Res., 69:547-553, 2009.

Saletta et al., "Molecular profiling of childhood cancer: Biomarkers and novel therapies," BBA Clinical, 1:59-77, 2014.

(56) References Cited

OTHER PUBLICATIONS

Samaha, Hanan S., et al. "Modulation of apoptosis by sulindac, curcumin, phenylethyl-3-methylcaffeate, and 6-phenylhexyl isothiocyanate: apoptotic index as a biomarker in colon cancer chemoprevention and promotion." *Cancer research* 57.7 (1997): 1301-1305.

Samal et al., "AMXT-1501, a novel polyamine transport inhibitor, synergizes with DFMO in inhibiting neuroblastoma cell proliferation by targeting both ornithine decarboxylase and golyamine transport," Int. J. Cancer, 133: 1323 -1334, 2013.

Sausville, Edward A., and Angelika M. Burger. "Contributions of human tumor xenografts to anticancer drug development." Cancer Research 66.7 (2006): 3351-3354.

Seiler and Knodgen, "High-performance liquid chromatographic procedure for the simultaneous determination of the natural polyamines and their monoacetyl derivatives," *J. Chromatogr.*, 221(2):227-235, 1980.

Seiler et al., "Endogenous and exogenous polyamines in support of tumor growth," *Cancer Research*, 50:5077-5083, 1990.

Sholler et al., [abstract]. In: Proceedings of the 104th Annual Meeting of the American Association for Cancer Research; Apr. 6-10, 2013; Washington, DC. Philadelphia (PA): AACR; Cancer Res 2013;73(8 Suppl):Abstract nr LB-179. doi: 10.1158/1538-7445.

Silva et al., "Role of peripheral polyamines in the development of inflammatory pain," Biochemical Pharmacology, 82:269-277, 2011.

Simoneau et al., "Alpha-difluoromethylornithine and polyamine levels in the human prostate: results of a phase IIa trial," *J. Natl. Cancer Inst.*, 93:57-9, 2001.

Simoneau et al., "The effect of difluoromethylornithine on decreasing prostate size and polyamines in men: results of a year-long phase IIb randomized placebo-controlled chemoprevention trial," *Cancer Epidemiol. Biomarkers Prev.*, 17:292-9, 2008.

Singh and Reddy, "Molecular markers in chemoprevention of colon cancer. Inhibition of expression of ras-p21 and p53 by sulindac during azoxymethane-induced colon carcinogenesis," *Annals. NY Acad. Sci.*, (768):205-209, 1995.

Singh et al., "*Bifidobacterium longum*, a lactic acid-producing intestinal bacterium inhibits colon cancer and modulates the intermediate biomarkers of colon carcinogenesis," *Carcinogenesis*, 18:833-841, 1997.

Singh et al., "Modulation of azoxymethane-induced mutational activation of ras protooncogenes by chemopreventive agents in colon carcinogenesis," *Carcinogenesis*, (15):1317-1323, 1994.

Smithson et al., "Discovery of potent and selective inhibitors of Trypanosoma brucei ornithine decarboxylase," *The Journal of Biological Chemistry*, 265(22):16771-16781, 2010.

Soda et al., "Polyamine-rich food decreases age-associated pathology and mortality in aged mice," *Experimental Gerontology*, 44: 727-732, 2009.

Su et al., "Multiple intestinal neoplasia caused by a mutation in the murine homolog of the APC gene," Science, (256):668-670, 1992.

Supplementary European Search Report issued in European Application No. 11 78 1359, dated Nov. 5, 2013.

Tabib et al., "Role of polyamines in mediating malignant transformation and oncogene expression," *Int. J. Biochem. Cell. Biol.*, 31:1289-1295, 1999.

Tempero et al., "Chemoprevention of mouse colon tumors with difluoromethylornithine during and after carcinogen treatment," *Cancer Res.*, 49(21):5793-7, 1989.

Thomas and Thomas, "Polyamine metabolism and cancer," *J. Cell Mol. Med.*, 7:113-26, 2003.

Thompson et al., "Inhibition of mammary carcinogenesis by sulfone metabolite of sulindac," *J. Natl. Cancer Inst.*, 1872:125-1260, 1995.

Thompson et al., "Levels of rectal mucosal polyamines and prostaglandin E2 predict ability of DFMO and sulindac to prevent colorectal adenoma," *Gastroenterology*, 139(3): 797-805, 2010.

Thompson, et al., "Sulfone metabolite of sulindac inhibits mammary carcinogenesis," Cancer Research, 57:267-271, 1997.

Vane and Botting, "Mechanism of action of anti-inflammatory drugs," *Scand. J. Rheumatol.*, 25(Suppl. 102):9-21, 1996.

Visvanathan et al., "Association among an ornithine decarboxylase polymorphism, androgen receptor gene (CAG) repeat length and prostate cancer risk," *J. Urol.*, 171(2 Pt 1):652-5, 2004.

Wallace and Caslake, "Polyamines and colon cancer," *Eur J Gastroenterol Helatol.*, 13(9): 1033-1039, 2001.

Wallace, "The physiological role of the polyamines," *Eur. J. Clin. Invest.*, 30:1-3, 2000.

Wang et al., "Mucosal polyamine measurements and colorectal cancer risk," *J. Cell. Biochem.*, 63:252-257, 1996.

Zell et al., "Associations of a polymorphism in the ornithine decarboxylase gene with colorectal cancer survival," *Clin. Cancer Res.*, 15(19):6208-16, 2009.

Zell et al., "Ornithine decarboxylase (Odc)-1 gene polymorphism effects on baseline tissue polyamine levels and adenoma recurrence in a randomized phase III adenoma prevention trial of DFMO + sulindac versus placebo," *J. Clin. Oncol.*, 26(15S):Abstract 1502, 2008.

Zell et al., "Ornithine decarboxylase-1 polymorphism, chemoprevention with eflornithine and sulindac, and outcomes among colorectal adenoma patients," *J. Natl. Cancer Inst.*, 102(19):1513-1516, 2010.

Zell et al., "Risk and risk reduction involving arginine intake and meat consumption in colorectal tumorgenesis and survival," *Intl. J. Cancer*, 120:459-68, 2007.

Zell et al., "Risk of cardiovascular events in a randomized placebo-controlled, double-blind trial of difluoromethylornithine plus sulindac for the prevention of sporadic colorectal adenomas," *Cancer Prev. Res.*, 2(3):209-12, 2009.

Zell et al., "Survival after colorectal cancer diagnosis is associated with colorectal cancer family history," *Cancer Epidemiol. Biomarkers Prev.*, 17:3134-40, 2008.

Zeng, G. X., et al. "New concept and clinical application of colorectal intraepithelial neoplasia and carcinoma." Zhonghua wai ke za zhi [Chinese journal of surgery] 45.7 (2007): 449-451.

Ziogas and Anton-Culver, "Validation of family history data in cancer family registries," *Am. J. Prev. Med.*, 24:190-8, 2003.

Zoumas-Morse et al., "Development of a polyamine database for assessing dietary intake," *J. Am. Diet. Assoc.*, 107:1024-1027, 2007.

Office Communication issued in Chilean Application No. 201801157, dated May 15, 2019. Original—English Translation provided below.

Office Communication issued in Chilean Application No. 201801157, dated May 15, 2019. (Machine Translation).

Burke, Carol A., et al. "Efficacy and safety of eflornithine (CPP-1X)/sulindac combination therapy versus each as monotherapy in patients with familial adenomatous polyposis (FAP): design and rationale of a randomized, double-blind, Phase III trial." *BMC gastroenterology* 16.1 (2016): 87.

Office Communication issued in corresponding Taiwanese Application No. 105135187, dated Jun. 29, 2020. (English translation appended).

Carbone et al., "Bioavailability Study of Oral Liquid and Tablet Forms of α-Difluoromethylornithine[1]," Clinical cancer research, Oct. 2000,vol. 6(10), 3850-3854.

Clinoril Tablet, appended paper, 2009.

Matsubara et al., "Chemoprevention for Familial Adenomatous Polyposis," Japanese Journal of Cancer and Chemotherapy, English Abstract, Jun. 2015, 42(6), 699-703.

Ooya et al, "Combination Drugs and Adherence to Taking Medicines," The Journal of the Japanese Society of Internal Medicine, 2011, Abstract.

Kawana et al, Prevent Colorectal Cancer (Part 2), The Journal of Therapy, 2010 Introduction.

Office Communication issued in corresponding Japanese Application No. 2018-543001, dated Sep. 3, 2020. (English translation appended).

* cited by examiner

| Product | Conditions | Packaging | T6 M | T0 |
|---|---|---|---|---|
| Eflornithine/ Sulindac 375mg/75mg | 25°C/75% HR | Closed bottles | 6,0 | 6,1 |
| | 30°C/65% HR | Closed bottles | 6,0 | |
| | 40°C/75% HR | Opened bottles | 6,4 | |
| | 40°C/75% HR | Closed bottles | 6,2 | |
| Eflornithine 250mg | 25°C/75% HR | Closed bottles | 6,9 | 6,5 |
| | 30°C/65% HR | Closed bottles | 7,1 | |
| | 40°C/75% HR | Opened bottles | 7,5 | |
| | 40°C/75% HR | Closed bottles | 7,3 | |
| Sulindac 150mg | 25°C/75% HR | Closed bottles | 2,9 | 2,9 |
| | 30°C/65% HR | Closed bottles | 3,2 | |
| | 40°C/75% HR | Opened bottles | 3,5 | |
| | 40°C/75% HR | Closed bottles | 3,2 | |

FIG. 1 ns in turn may lead to reduced# EFLORNITHINE AND SULINDAC, FIXED DOSE COMBINATION FORMULATION The present application is a national phase application under 35 U.S.C. § 371 of International Application No. PCT/US2016/059689, filed Oct. 31, 2016, which claims the priority benefit of U.S. provisional application No. 62/248,810, filed Oct. 30, 2015, U.S. provisional application No. 62/358,698, filed Jul. 6, 2016, European application No. 16306429.8, filed Oct. 28, 2016, and European application No. 16306430.6, filed Oct. 28, 2016, the entire contents of each of which are specifically incorporated herein by reference.

BACKGROUND OF THE INVENTION

1. Field of the Invention

The present invention relates generally to the field of cancer biology and medicine. More particularly, it concerns compositions for the prevention and treatment of carcinomas.

2. Description of Related Art

Cancer cells have the ability to co-opt multiple pathways to fulfill their increased requirement for specific metabolites (Vander Heiden, 2011). The nonsteroidal anti-inflammatory drugs (NSAIDs), including aspirin, ibuprofen, piroxicam (Reddy et al., 1990; Singh et al., 1994), indomethacin (Narisawa, 1981), and sulindac (Piazza et al., 1997; Rao et al., 1995), effectively inhibit colon carcinogenesis in the AOM-treated rat model. Sulindac sulfone, a metabolite of the NSAID sulindac, lacks COX-inhibitory activity yet induces apoptosis in tumor cells (Piazza et al., 1995; Piazza et al., 1997b) and inhibits tumor development in several rodent models of carcinogenesis (Thompson et al., 1995; Piazza et al., 1995, 1997a).

α-Difluoromethylornithine (DFMO) is an enzyme-activated, irreversible inhibitor of ornithine decarboxylase (ODC) and causes depletion in the intracellular concentrations of putrescine and its derivative, spermidine (Pegg, 1988). In experimental animal models, DFMO is a potent inhibitor of carcinogenesis that is especially active in preventing carcinogen-induced epithelial cancers of many organs, including those of the colon (Weeks et al., 1982; Thompson et al., 1985; Nowels et al., 1986; Nigro et al., 1987).

A major impediment to the translation of cancer chemoprevention research into clinical practice has been marginal agent efficacy and toxicities that exceed benefit (Psaty and Potter, 2006; Lippman, 2006). For example, the demonstrated marked efficacy of polyamine-inhibitory combination of long-term daily oral D,L-α-difluoromethylornithine (DFMO, eflornithine) and sulindac among colorectal adenoma (CRA) patients has been demonstrated (Meyskens et al., 2008), however, treatment was associated with modest, subclinical ototoxicity (McLaren et al., 2008), and a greater number of cardiovascular events among patients with high baseline cardiovascular risk (Zell et al., 2009).

The convenience of co-administering two or more active pharmaceutical ingredients in a unit dosage form, as opposed to the administration of a number of separate doses of two or more pharmaceuticals at regular intervals, has been recognized in the pharmaceutical arts and is described in U.S. Pat. Nos. 6,428,809 and 6,702,683. Potential advantages to the patient and clinician include (1) minimization or elimination of local and/or systemic side effects; (2) more effective treatment of co-morbid conditions; (3) improved polypharmacy; and (4) better patient compliance with overall disease management, which in turn may lead to reduced costs due to fewer trips to the physician, reduced hospitalization, and improved patient well-being. Fixed dose combination products, with two or more formulations combined or co-formulated in a single dosage form, may be useful in multiple drug regimens where improved clinical effectiveness, enhanced patient adherence and simplified dosing are desired. However, pharmaceutical drug product development of solid oral dosage forms is complicated at both the research and development level and at the commercial manufacturing level even for single active pharmaceutical ingredient (API) formulation. For more-than-one API, additional complicating factors are expected, including (1) drug-drug interaction, (2) drug-excipient interaction, (3) simultaneous release profiles, (4) differential release profiles, and (5) blend uniformity of each drug component. In view of these hurdles, developing fixed-dose combinations with the same or similar release profiles as the single entity drug products typically represents a significant challenge. Fixed dose combinations of eflornithine and sulindac that overcome some or all of these challenges would have a significant potential impact for the effective treatment and/or prevention of a wide range of diseases or disorders, including familial adenoma polyposis (FAP).

SUMMARY OF THE INVENTION

In one aspect, the present invention provides compositions comprising a fixed dose combination of a pharmaceutically effective amount of eflornithine and a pharmaceutically effective amount of a nonsteroidal anti-inflammatory drug (NSAID) or a metabolite thereof. In some embodiments, the fixed dose combination is a pharmaceutically effective amount of eflornithine and a pharmaceutically effective amount of sulindac.

In some embodiments, the eflornithine is eflornithine hydrochloride monohydrate. In some embodiments, the eflornithine is eflornithine hydrochloride monohydrate racemate. In some embodiments, the eflornithine hydrochloride monohydrate is a racemic mixture of its two enantiomers. In some embodiments, the eflornithine hydrochloride monohydrate is a substantially optically pure preparation. In some embodiments, the eflornithine hydrochloride monohydrate is L-eflornithine hydrochloride monohydrate or D-eflornithine hydrochloride monohydrate. In some embodiments, the eflornithine is anhydrous free base eflornithine.

In some embodiments, the eflornithine is present in an amount of about 10 to about 1000 mg. In some embodiments, the eflornithine is present in an amount of about 250 to about 500 mg. In some embodiments, the eflornithine is present in an amount of about 300 to about 450 mg. In some embodiments, the eflornithine is present in an amount of about 350 to about 400 mg. In some embodiments, the eflornithine is present in an amount of about 35 to about 60 weight percent. In some embodiments, the eflornithine is present in an amount of about 40 to about 55 weight percent. In some embodiments, the eflornithine is present in an amount of about 50 to about 55 weight percent. In some embodiments, the eflornithine is present in an amount of about 52 to about 54 weight percent. In some embodiments, the amount of eflornithine hydrochloride monohydrate racemate is from 52 to 54 weight percent. In some embodiments, the eflornithine is present in an amount of about 375 mg. In some embodiments, the amount of eflornithine hydrochloride monohydrate racemate is 375 mg.

In some embodiments, the sulindac is present in an amount from about 10 to about 1500 mg. In some embodiments, the sulindac is present in an amount of about 50 to about 100 mg. In some embodiments, the sulindac is present in an amount of about 70 to about 80 mg. In some embodiments, the sulindac is present in an amount of about 75 mg. In some embodiments, the amount of sulindac is 75 mg. In some embodiments, the sulindac is present in an amount of about 5 to about 20 weight percent. In some embodiments, the sulindac is present in an amount of about 8 to about 15 weight percent. In some embodiments, the sulindac is present in an amount of about 10 to about 12 weight percent. In some embodiments, the amount of sulindac is from 10 to 11 weight percent.

In some embodiments, the eflornithine is present in an amount of about 375 mg and the sulindac is present in an amount of about 75 mg.

In some embodiments, the formulation further comprises an excipient. In some embodiments, the excipient is starch, colloidal silicon dioxide, or silicified microcrystalline cellulose. In some embodiments, the excipient is colloidal silicon dioxide. In some embodiments, the formulation further comprises a second excipient. In some embodiments, the second excipient is silicified microcrystalline cellulose.

In some embodiments, the formulation further comprises a lubricant. In some embodiments, the lubricant is magnesium stearate, calcium stearate, sodium stearate, glyceryl monostearate, aluminum stearate, polyethylene glycol, boric acid or sodium benzoate. In some embodiments, the lubricant is magnesium stearate. In some embodiments, magnesium stearate is present in an amount of about 0.25 to about 2 weight percent. In some embodiments, the amount of magnesium stearate is from about 0.75 to about 2 weight percent. In some embodiments, the amount of magnesium stearate is from about 1 to about 1.5 weight percent. In some embodiments, the amount of magnesium stearate is about 1.1 weight percent. In some embodiments, magnesium stearate is present in an amount of about 1.5 weight percent.

In some embodiments, the compositions are in the form of a capsule, tablet, mini tablets, granules, pellets, solution, gel, cream, foam or patch. In some embodiments, the composition is in the form of a tablet, for example, a monolayer tablet.

In some embodiments, the weight of the tablet is from about 10 mg to about 2,500 mg. In some embodiments, the weight of the tablet is from about 250 mg to about 1,500 mg. In some embodiments, the weight of the tablet is from about 650 mg to about 1,000 mg. In some embodiments, the weight of the tablet is from about 675 mg to about 725 mg. In some embodiments, the weight of the tablet is about 700 mg.

In some embodiments, the weight of the capsule, mini tablet, granules, or pellets is from about 10 mg to about 2,500 mg. In some embodiments, the weight of the capsule, mini tablet, granules, or pellets is from about 250 mg to about 1,500 mg. In some embodiments, the weight of the capsule, mini tablet, granules, or pellets is from about 650 mg to about 1,000 mg. In some embodiments, the weight of the capsule, mini tablet, granules, or pellets is from about 675 mg to about 725 mg. In some embodiments, the weight of the capsule, mini tablet, granules, or pellets is about 700 mg.

In some embodiments, the tablet further comprises a coating. In some embodiments, the coating is a modified release coating or an enteric coating. In some embodiments, the coating is a pH-responsive coating. In some embodiments, the coating comprises cellulose acetate phthalate (CAP), cellulose acetate trimelletate (CAT), poly (vinyl acetate) phthalate (PVAP), hydroxypropylmethylcellulose phthalate (HP), poly(methacrylate ethylacrylate) (1:1) copolymer (MA-EA), poly(methacrylate methylmethacrylate) (1:1) copolymer (MA MMA), poly(methacrylate methylmethacrylate) (1:2) copolymer, or hydroxypropylmethylcellulose acetate succinate (HPMCAS). In some embodiments, the coating masks the taste of eflornithine. In some embodiments, the coating comprises hydroxypropyl methylcellulose, titanium dioxide, polyethylene glycol, and iron oxide yellow.

In some embodiments, the amount of coating is from about 1 to about 5 weight percent. In some embodiments, the amount of coating is from about 2 to about 4 weight percent. In some embodiments, the amount of coating is about 3 weight percent. In some embodiments, the amount of coating is from about 5 mg to about 30 mg. In some embodiments, the amount of coating is from about 15 mg to about 25 mg. In some embodiments, the amount of coating is about 21 mg.

In some embodiments, the weight of the tablet comprising a coating is from about 675 mg to about 750 mg. In some embodiments, the weight of the tablet comprising a coating is from about 700 mg to about 725 mg. In some embodiments, the weight of the tablet comprising a coating is about 721 mg.

In one aspect, there is provided a method of preventing and/or treating a disease or condition in a patient in need thereof, comprising administering to the patient the fixed dose combination of a pharmaceutically effective amount of eflornithine and a pharmaceutically effective amount of sulindac provided herein.

In some embodiments, the method further comprises administering to the patient a second composition comprising the fixed dose combination of a pharmaceutically effective amount of eflornithine and a pharmaceutically effective amount of sulindac provided herein. In some embodiments, the first and the second compositions comprise the same fixed dose combinations. In some embodiments, the first and the second administration occurs simultaneously. In some embodiments, the second administration follows the first administration by an interval of 1 second to 1 hour. In some embodiments, the first and the second compositions are both formulated as tablets and contain the same amounts of eflornithine and sulindac.

In some embodiments, the disease is cancer. In some embodiments, the cancer is colon cancer, breast cancer, pancreatic cancer, brain cancer, lung cancer, stomach cancer, a blood cancer, skin cancer, testicular cancer, prostate cancer, ovarian cancer, liver cancer, or esophageal cancer. In some embodiments, the colon cancer is familial adenomatous polyposis. In some embodiments, the cancer is a neuroendocrine tumor. In some embodiments, the neuroendocrine tumor is neuroblastoma.

In some embodiments, the condition is a skin condition. In some embodiments, the skin condition is facial hirsutism.

In some embodiments, the composition is administered orally, intraarterially, intravenously, or topically. In some embodiments, the composition is administered orally.

In some embodiments, the composition is administered orally. In some embodiments, the composition is administered every 12 hours. In some embodiments, the composition is administered every 24 hours. In some embodiments, the composition is administered at least a second time.

In another aspect, there is provided a method of producing a tablet comprising about 375 mg eflornithine hydrochloride and about 75 mg of sulindac comprising: (a) pre-mixing sulindac and an excipient to form a first mixture; (b) mixing the first mixture with a second mixture comprising eflornithine and an excipient to form a blend; (c) screening the blend to form a granulated blend; (d) adding a lubricant to the granulated blend to obtain a final blend; and (e) applying a compression force to the final blend to form a tablet. In some embodiments, the method further comprises mixing the granulated blend prior to step (d) and mixing the final blend prior to step (e).

In some embodiments, there are two excipients in the first mixture, wherein the first excipient is colloidal silicon dioxide, and the second excipient is silicified microcrystalline cellulose. In some embodiments, the excipient of the second mixture is silicified microcrystalline cellulose.

In some embodiments, the pre-mixing is performed in a polyethylene-coated container. In some embodiments, the mixing is performed in a diffusion blender.

In some embodiments, the lubricant is magnesium stearate. In some embodiments, the magnesium stearate is sieved through a screen prior to step (d). In some embodiments, the screen is a 500 µm screen.

In some embodiments, screening comprises applying the blend to a rotative calibrator. In some embodiments, the rotative calibrator comprises a 1.0 mm screen.

In some embodiments, the method further comprises a pre-compression step after step (d) and prior to step (e), wherein the blend is compressed with a force lower than the force of step (e) to form a pre-compressed blend, further wherein the compression force of step (e) then acts on the pre-compressed blend to form the tablet. In some embodiments, the pre-compression step prevents tablet capping. In some embodiments, a compression force of the pre-compression step is applied at about 5 to about 15 percent of the compression force applied in step (e). In some embodiments, the compression force of the pre-compression step is from 2.5 to 3.5 kN. In some embodiments, the compression force of the pre-compression step is about 3 kN. In some embodiments, the compression force of step (e) is from 20 to 35 kN. In some embodiments, the compression force of step (e) is about 25 kN.

In some embodiments, the method further comprises coating the tablet. In some embodiments, the coating comprises hydroxypropyl methylcellulose, titanium dioxide, polyethylene glycol, and iron oxide yellow.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1: Stability analysis of prototype Lot 7107/04 of 700 mg tablets of eflornithine HCl monohydrate (375 mg) and sulindac (75 mg). Tablets have a 3% w/w coating. Samples were analyzed at time zero (T0) and at 6 months (T6) using a validated Karl Fischer titration method for determination of water content. Samples were stored in HDPE bottles with and without caps in verified stability chambers. Values represent the percentage of water in each tablet at the specified conditions.

DESCRIPTION OF ILLUSTRATIVE EMBODIMENTS

Figure 2A:
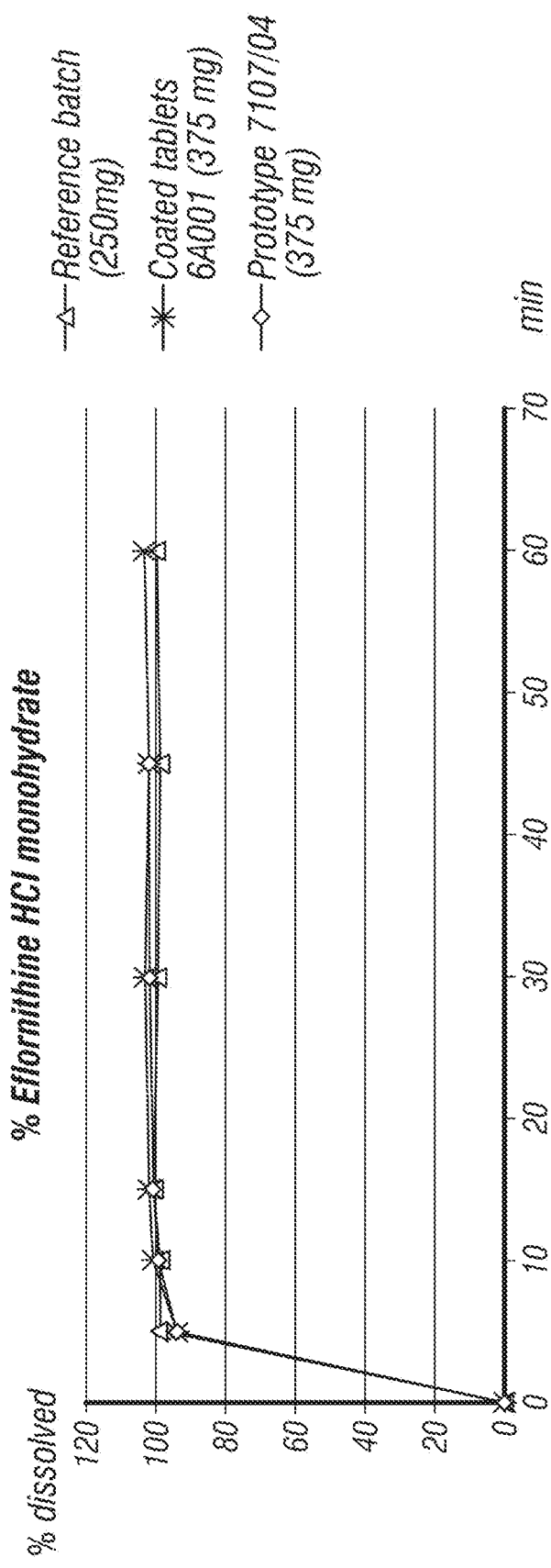
FIGS. 2A-2B: Results of dissolution analysis of coated tablet Lots 7107/04 and 6A001. Reference tablets of 250 mg eflornithine HCl monohydrate and commercial 150 mg sulindac are included for comparison. Co-formulated tablets contain 375 mg of eflornithine HCl monohydrate and 75 mg of sulindac with a 3% w/w coating.

In several aspects, compositions are provided for a fixed dose combination (FDC) of eflornithine and sulindac. Methods are also provided for the manufacture of the fixed dose combinations of the present invention which overcome problems associated with current methods. The methods of manufacture have been designed to solve problems including drug-drug interactions, drug-excipient interactions, and blend uniformity of each drug component. Accordingly, the fixed dose combination of the present invention may be used to minimize local and/or systemic side effects, provide more effective treatments, improve polypharmacy, and provide better patient compliance.

I. FAMILIAL ADENOMATOUS POLYPOSIS

Excess polyamine formation has long been implicated in epithelial carcinogenesis, particularly colorectal carcinogenesis. Polyamines are small ubiquitous molecules involved in various processes, including, for example, transcription, RNA stabilization, and ion channel gating (Wallace, 2000). Ornithine decarboxylase (ODC), the first enzyme in polyamine synthesis, is essential for normal development and tissue repair in mammals but is down-regulated in most adult tissues (Gerner and Meyskens, 2004). Multiple abnormalities in the control of polyamine metabolism and transport result in increased polyamine levels that can promote tumorigenesis in several tissues (Thomas and Thomas, 2003).

Familial adenomatous polyposis (FAP) is a syndrome associated with high risk of colon and other cancers. FAP is caused by mutations in the adenomatous polyposis coli (APC) tumor suppressor gene, and APC signaling has been shown to regulate ODC expression in both human cells (Fultz and Gerner, 2002) and in a mouse model of FAP (Erdman et al., 1999). Polyamine metabolism is up-regulated in intestinal epithelial tissues of humans with (Giardiello et al., 1997) FAP.

Wild type APC expression leads to decreased expression of ODC, while mutant APC leads to increased expression of ODC. The mechanism of APC-dependent regulation of ODC involves E-box transcription factors, including the transcriptional activator c-MYC and the transcriptional repressor MAD1 (Fultz and Gerner, 2002; Martinez et al., 2003). c-MYC was shown by others to regulate ODC transcription (Bellofernandez et al., 1993). Several genes involved in polyamine metabolism are essential genes for optimal growth in most organisms, and are down-regulated in non-proliferating and/or adult cells and tissues (Gerner and Meyskens, 2004). The polyamines influence specific cellular phenotypes, in part, by affecting patterns of gene expression, as reviewed elsewhere (Childs et al., 2003).

Familial Adenomatous Polyposis (FAP), an inherited polyposis syndrome, is the result of germ-line mutation of the adenomatous polyposis coli (APC) tumor suppressor gene (Su et al., 1992). This autosomal-dominant condition with variable expression is associated with the development of hundreds of colonic adenomas, which uniformly progress to adenocarcinoma by forty years of age, two decades earlier than the mean age diagnosis for sporadic colon cancer (Bussey, 1990). In prior studies of pre-symptomatic individuals with FAP, increased levels of the polyamines spermidine and spermine, and their diamine precursor putrescine, have been detected in normal-appearing colorectal biopsies when compared to normal family member controls (Giardiello et al., 1997). The activity of ornithine decarboxylase (ODC), the first and rate-limiting enzyme in mammalian polyamine synthesis, also is elevated in apparently normal colonic mucosal biopsies from FAP patients (Giardiello et al., 1997; Luk and Baylin, 1984). These findings are of interest as the polyamines are necessary for optimal cell proliferation (Pegg, 1986). Further, suppression of ODC activity, using the enzyme-activated irreversible inhibitor DFMO, inhibits colon carcinogenesis in carcinogen-treated rodents (Kingsnorth et al., 1983; Tempero et al., 1989).

The Min (multiple intestinal neoplasia) mouse, which shares a mutated APC/apc genotype with FAP, serves as a useful experimental animal model for human FAP patients (Lipkin, 1997). The Min mouse can develop greater than 100 gastrointestinal adenomas/adenocarcinomas throughout the gastrointestinal tract by 120 days of life leading to GI bleeding, obstruction and death. A combination therapy of DFMO and sulindac was shown to be effective in reducing adenomas in these mice. See U.S. Pat. No. 6,258,845 and Gerner and Meyskens, 2004, which are incorporated herein by reference.

II. EFLORNITHINE

The term "eflornithine" when used by itself and free of context refers to 2,5-diamino-2-(difluoromethyl)pentanoic acid in any of its forms, including non-salt and salt forms (e.g., eflornithine HCl), anhydrous and hydrate forms of non-salt and salt forms (e.g., eflornithine hydrochloride monohydrate), solvates of non-salt and salts forms, its enantiomers (R and S forms, which may also by identified as d and l forms), and mixtures of these enantiomers (e.g., racemic mixture). By "substantially optically pure preparation" is meant a preparation of a first enantiomer which contains about 5% wt. or less of the opposite enantiomer. Specific forms of eflornithine include eflornithine hydrochloride monohydrate (i.e., CAS ID: 96020-91-6; MW: 236.65), eflornithine hydrochloride (i.e., CAS ID: 68278-23-9; MW: 218.63), and anhydrous free base eflornithine (i.e., CAS ID: 70052-12-9; MW: 182.17). Where necessary, the specific form of eflornithine has been further specified. In some embodiments, the eflornithine of the present disclosure is eflornithine hydrochloride monohydrate (i.e., CAS ID: 96020-91-6). The terms "eflornithine" and "DFMO" are used interchangeably herein. DFMO is an abbreviation for difluoromethylornithine. Other synonyms of eflornithine and DFMO include: α-difluoromethylornithine, 2-(difluoromethyl)-DL-ornithine, 2-(difluoromethyl)-dl-ornithine, 2-(Difluoromethyl)ornithine, DL-α-difluoromethylornithine, N-Difluoromethylornithine, αδ-diamino-α-(difluoromethyl) valeric acid, and 2,5-diamino-2-(difluoromethyl)pentanoic acid.

Eflornithine is an enzyme-activated irreversible inhibitor of ornithine decarboxylase (ODC), the rate-limiting enzyme of the polyamine biosynthetic pathway. As a result of this inhibition of polyamine synthesis, the compound is effective in preventing cancer formation in many organ systems, inhibiting cancer growth, and reducing tumor size. It also has synergistic action with other antineoplastic agents.

Eflornithine has been shown to decrease APC-dependent intestinal tumorigenesis in mice (Erdman et al., 1999). Oral eflornithine administered daily to humans inhibits ODC enzyme activity and polyamine contents in a number of epithelial tissues (Love et al., 1993; Gerner et al., 1994; Meyskens et al., 1994; Meyskens et al., 1998; Simoneau et al., 2001; Simoneau et al., 2008). Eflornithine in combination with the non-steroidal anti-inflammatory drug (NSAID) sulindac, has been reported to markedly lower the adenoma recurrence rate among individuals with colonic adenomas when compared to placebos in a randomized clinical trial (Meyskens et al., 2008).

Eflornithine was originally synthesized by Centre de Recherche Merrell, Strasbourg. Current U.S. Food and Drug Administration (FDA) approvals include:

African sleeping sickness. High dose systemic IV dosage form—not marketed (Sanofi/WHO)

Hirsutis (androgen-induced excess hair growth) topical dosage form

While no oral formulations of eflornithine have yet been approved by the FDA, topical and injectable forms have been approved. Vaniqa® is a cream, which contains 15% w/w eflornithine hydrochloride monohydrate, corresponding to 11.5% w/w anhydrous eflornithine (EU), respectively 13.9% w/w anhydrous eflornithine hydrochloride (U.S.), in a cream for topical administration. Ornidyl® is an eflornithine HCl solution suitable for injection or infusion. It is supplied in the strength of 200 mg eflornithine hydrochloride monohydrate per ml (20 g/100 mL).

Eflornithine and its use in the treatment of benign prostatic hypertrophy are described in U.S. Pat. Nos. 4,413,141, and 4,330,559. The '141 Patent describes eflornithine as being a powerful inhibitor of ODC, both in vitro and in vivo. Administration of eflornithine is reported to cause a decrease in putrescine and spermidine concentrations in cells in which these polyamines are normally actively produced. Additionally, eflornithine has been shown to be capable of slowing neoplastic cell proliferation when tested in standard tumor models. The '559 Patent describes the use of eflornithine and eflornithine derivatives for the treatment of benign prostatic hypertrophy. Benign prostatic hypertrophy, like many disease states characterized by rapid cell proliferation, is accompanied by abnormal elevation of polyamine concentrations.

Eflornithine can potentially be given continuously with significant anti-tumor effects. This drug is relatively non-toxic at low doses of 0.4 $g/m^2$/day to humans while producing inhibition of putrescine synthesis in tumors. Studies in a rat-tumor model demonstrate that eflornithine infusion can produce a 90% decrease in tumor putrescine levels without suppressing peripheral platelet counts.

Side effects observed with eflornithine include effects on hearing at high doses of 4 g/m$^2$/day that resolve when it is discontinued. These effects on hearing are not observed at lower doses of 0.4 g/m$^2$/day when administered for up to one year (Meyskens et al., 1994). In addition, a few cases of dizziness/vertigo are seen that resolve when the drug is stopped. Thrombocytopenia has been reported predominantly in studies using high "therapeutic" doses of eflornithine (>1.0 g/m$^2$/day) and primarily in cancer patients who had previously undergone chemotherapy or patients with compromised bone marrow. Although the toxicity associated with eflornithine therapy is not, in general, as severe as other types of chemotherapy, in limited clinical trials it has been found to promote a dose-related thrombocytopenia. Moreover, studies in rats have shown that continuous infusion of eflornithine for 12 days significantly reduces platelet counts compared with controls. Other investigations have made similar observations in which thrombocytopenia is the major toxicity of continuous intravenous eflornithine therapy. These findings suggest that eflornithine may significantly inhibit ODC activity of the bone marrow precursors of megakaryocytes. Eflornithine may inhibit proliferative repair processes, such as epithelial wound healing.

A phase III clinical trial assessed the recurrence of adenomatous polyps after treatment for 36 months with DFMO plus sulindac or matched placebos. Temporary hearing loss is a known toxicity of treatment with DFMO, thus a comprehensive approach was developed to analyze serial air conduction audiograms. The generalized estimating equation method estimated the mean difference between treatment arms with regard to change in air conduction pure tone thresholds while accounting for within-subject correlation due to repeated measurements at frequencies. Based on 290 subjects, there was an average difference of 0.50 dB between subjects treated with DFMO plus sulindac compared with those treated with placebo (95% confidence interval, −0.64 to 1.63 dB; P=0.39), adjusted for baseline values, age, and frequencies. There is a <2 dB difference in mean threshold for patients treated with DFMO plus sulindac compared with those treated with placebo. The results of this study are discussed in greater detail in McLaren et al., 2008, which is incorporated herein by reference in its entirety.

III. NSAIDS

NSAIDs are anti-inflammatory agents that are not steroids. In addition to anti-inflammatory effects, they are also reported to have analgesic, antipyretic, and platelet-inhibitory effects. They are used, for example, in the treatment of chronic arthritic conditions and certain soft tissue disorders associated with pain and inflammation. They have been reported to act by blocking the synthesis of prostaglandins by inhibiting cyclooxygenase, which converts arachidonic acid to cyclic endoperoxides, precursors of prostaglandins. Inhibition of prostaglandin synthesis accounts for their analgesic, antipyretic, and platelet-inhibitory actions; other mechanisms may contribute to their anti-inflammatory effects. Certain NSAIDs also may inhibit lipoxygenase enzymes or phospholipase C or may modulate T-cell function. See AMA Drug Evaluations Annual, 1814-5, 1994.

The nonsteroidal anti-inflammatory drugs (NSAIDs), including aspirin, ibuprofen, piroxicam (Reddy et al., 1990; Singh et al., 1994), indomethacin (Narisawa, 1981), and sulindac (Piazza et al., 1997; Rao et al., 1995), effectively inhibit colon carcinogenesis in the AOM-treated rat model. NSAIDs also inhibit the development of tumors harboring an activated Ki-ras (Singh and Reddy, 1995). NSAIDs appear to inhibit carcinogenesis via the induction of apoptosis in tumor cells (Bedi et al., 1995; Lupulescu, 1996; Piazza et al., 1995; Piazza et al., 1997b). A number of studies suggest that the chemopreventive properties of the NSAIDs, including the induction of apoptosis, are a function of their ability to inhibit prostaglandin synthesis (reviewed in DuBois et al., 1996; Lupulescu, 1996; Vane and Bating, 1997). Studies, however, indicate that NSAIDs may act through both prostaglandin-dependent and -independent mechanisms (Alberts et al., 1995; Piazza et al., 1997a; Thompson et al., 1995; Hanif, 1996). Sulindac sulfone, a metabolite of the NSAID sulindac, lacks COX-inhibitory activity yet induces apoptosis in tumor cells (Piazza et al., 1995; Piazza et al., 1997b) and inhibits tumor development in several rodent models of carcinogenesis (Thompson et al., 1995; Piazza et al., 1995, 1997a).

Several NSAIDs have been examined for their effects in human clinical trials. A phase IIa trial (one month) of ibuprofen was completed and even at the dose of 300 mg/day, a significant decrease in prostoglandin $E_2$ ($PGE_2$) levels in flat mucosa was seen. A dose of 300 mg of ibuprofen is very low (therapeutic doses range from 1200-3000 mg/day or more), and toxicity is unlikely to be seen, even over the long-term. However, in animal chemoprevention models, ibuprofen is less effective than other NSAIDs.

A. Aspirin

Aspirin, also known as acetylsalicylic acid, is a salicylate drug, often used as an analgesic to relieve minor aches and pains, as an antipyretic to reduce fever, and as an anti-inflammatory medication. Aspirin was first isolated by Felix Hoffmann, a chemist with the German company Bayer in 1897. Salicylic acid, the main metabolite of aspirin, is an integral part of human and animal metabolism. While in humans much of it is attributable to diet, a substantial part is synthesized endogenously. Today, aspirin is one of the most widely used medications in the world, with an estimated 40,000 tons of it being consumed each year. In countries where aspirin is a registered trademark owned by Bayer, the generic term is acetylsalicylic acid (ASA).

Aspirin also has an antiplatelet effect by inhibiting the production of thromboxane, which under normal circumstances binds platelet molecules together to create a patch over damaged walls of blood vessels. Because the platelet patch can become too large and also block blood flow, locally and downstream, aspirin is also used long-term, at low doses, to help prevent heart attacks, strokes, and blood clot formation in people at high risk of developing blood clots. It has also been established that low doses of aspirin may be given immediately after a heart attack to reduce the risk of another heart attack or of the death of cardiac tissue. Aspirin may be effective at preventing certain types of cancer, particularly colorectal cancer.

Undesirable side effects of taking aspirin orally include gastrointestinal ulcers, stomach bleeding, and tinnitus, especially in higher doses. In children and adolescents, aspirin is no longer indicated to control flu-like symptoms or the symptoms of chickenpox or other viral illnesses, because of the risk of Reye's syndrome.

Aspirin is part of a group of medications called nonsteroidal anti-inflammatory drugs (NSAIDs), but differs from most other NSAIDS in the mechanism of action. Though aspirin, and others in its group called the salicylates, have similar effects (antipyretic, anti-inflammatory, analgesic) to the other NSAIDs and inhibit the same enzyme cyclooxygenase, aspirin (but not the other salicylates) does so in an irreversible manner and, unlike others, affects more the COX-1 variant than the COX-2 variant of the enzyme.

B. Sulindac and its Major Metabolites, Sulidac Sulfone and Sulindac Sulfide

Sulindac is a nonsteroidal, anti-inflammatory indene derivative with the following chemical designation; (Z)-5-fluoro-2-methyl-1-((4-(methylsulfinyl)phenyl)methylene)-1H-indene-3-acetic acid (Physician's Desk Reference, 1999). Without being bound by theory, the sulfinyl moiety is converted in vivo by reversible reduction to a sulfide metabolite and by irreversible oxidation to a sulfone metabolite (exisulind). See U.S. Pat. No. 6,258,845, which is incorporated herein by reference. Sulindac, which also inhibits Ki-ras activation, is metabolized to two different molecules, which differ in their ability to inhibit COX, yet both are able to exert chemopreventive effects via the induction of apoptosis. Sulindac sulfone lacks COX-inhibitory activity, and most likely facilitates the induction of apoptosis in a manner independent of prostaglandin synthesis. Available evidence indicates that the sulfide derivative is at least one of the biologically active compounds. Based on this, sulindac may be considered a prodrug.

Sulindac (Clinoril®) is available, for example, as 150 mg and 200 mg tablets. The most common dosage for adults is 150 to 200 mg twice a day, with a maximal daily dose of 400 mg. After oral administration, about 90% of the drug is absorbed. Peak plasma levels are achieved in about 2 hours in fasting patients and 3 to 4 hours when administered with food. The mean half-life of sulindac is 7.8 hours: the mean half-life of the sulfide metabolite is 16.4 hours. U.S. Pat. Nos. 3,647,858 and 3,654,349 cover preparations of sulindac; both patents are incorporated by reference herein in their entireties.

Sulindac is indicated for the acute and long-term relief of signs and symptoms of osteoarthritis, rheumatoid arthritis, ankylosing spondylitis, acute gout, and acute painful shoulder. The analgesic and anti-inflammatory effects exerted by sulindac (400 mg per day) are comparable to those achieved by aspirin (4 g per day), ibuprofen (1200 mg per day), indometacin (125 mg per day), and phenylbutazone (400 to 600 mg per day). Side effects of sulindac include mild gastrointestinal effects in nearly 20% of patients, with abdominal pain and nausea being the most frequent complaints. CNS side effects are seen in up to 10% of patients, with drowsiness, headache, and nervousness being those most frequently reported. Skin rash and pruritus occur in 5% of patients. Chronic treatment with sulindac can lead to serious gastrointestinal toxicity such as bleeding, ulceration, and perforation.

The potential use of sulindac for chemoprevention of cancers, and in particular colorectal polyps, has been well studied. For example, U.S. Pat. Nos. 5,814,625 and 5,843,929, which are both incorporated herein by reference, report potential chemopreventive uses of sulindac in humans. Sulindac has been shown to produce regression of adenomas in Familial Adenomatous Polyposis (FAP) patients (Muscat et al., 1994), although at least one study in sporadic adenomas has shown no such effect (Ladenheim et al., 1995). Sulindac and its sulfone metabolite exisulind have been tested and continue to be tested clinically for the prevention and treatment of several cancer types.

C. Piroxicam

Piroxicam is a non-steroidal anti-inflammatory agent that is well established in the treatment of rheumatoid arthritis and osteoarthritis with the following chemical designation: 4-hydroxy-2-methyl-N-2-pyridyl-2H-1,2-benzothiazine-3-carboxamide 1,1-dioxide. Its usefulness also has been demonstrated in the treatment of musculoskeletal disorders, dysmenorrhea, and postoperative pain. Its long half-life enables it to be administered once daily. The drug has been shown to be effective if administered rectally. Gastrointestinal complaints are the most frequently reported side effects.

Piroxicam has been shown to be an effective chemoprevention agent in animal models (Pollard and Luckert, 1989; Reddy et al., 1987), although it demonstrated side effects in a recent IIb trial. A large meta-analysis of the side effects of the NSAIDs also indicates that piroxicam has more side effects than other NSAIDs (Lanza et al., 1995).

The combination of DFMO and piroxicam has been shown to have a synergistic chemopreventive effect in the AOM-treated rat model of colon carcinogenesis (Reddy et al., 1990), although DFMO exerted a greater suppressive effect than piroxicam on Ki-ras mutation and tumorigenesis when each agent was administered separately (Reddy et al., 1990). In one study, administration of DFMO or piroxicam to AOM-treated rats reduced the number of tumors harboring Ki-ras mutations from 90% to 36% and 25%, respectively (Singh et al., 1994). Both agents also reduced the amount of biochemically active p21 ras in existing tumors.

D. Celecoxib

Celecoxib is a non-steroidal anti-inflammatory agent that is well established in the treatment of osteoarthritis, rheumatoid arthritis, acute pain, ankylosing spondylitis, and to reduce the number of colon and rectal polyps in patients with FAP with the following chemical designation: 4-[5-(4-Methylphenyl)-3-(trifluoromethyl)pyrazol-1-yl]benzenesulfonamide. Celecoxib is marketed under the brand names Celebrex, Celebra, and Onsenal by Pfizer. Celecoxib is a selective COX-2 inhibitor. Side effects of celecoxib include a 30% increase in rates of heart and blood vessel disease. Additionally, the risks of gastrointestinal side effects are greater than 80%.

E. Combinations of NSAIDs

Combinations of various NSAIDs may also be used in some embodiments. By using lower doses of two or more NSAIDs, it is possible, in some embodiments, to reduce the side effects or toxicities associated with higher doses of individual NSAIDs. For example, in some embodiments, sulindac may be used together with celecoxib. Examples of NSAIDs that may be used in combination with one another include, but are not limited to: ibuprofen, naproxen, fenoprofen, ketoprofen, flurbiprofen, oxaprozin, indomethacin, sulindac, etodolac, diclofenac, piroxicam, meloxicam, tenoxicam, droxicam, lomoxicam, isoxicam, mefenamic acid, meclofenamic acid, flufenamic acid, tolfenamic acid, celecoxib, rofecoxib, valdecoxib, parecoxib, lumiracoxib, and etoricoxib.

IV. EFLORNITHINE/SULINDAC COMBINATION THERAPY

The compositions provided herein may be used, in some embodiments, to reduce the number of, inhibit the growth of, and/or prevent the occurrence of cancer cells in patients. Target cancer cells include cancers of the lung, brain, prostate, kidney, liver, ovary, breast, skin, stomach, esophagus, head and neck, testicles, colon, cervix, lymphatic system and blood. In some embodiments, the compositions may be used to treat and/or prevent colon cancer, familial adenomatous polyposis (FAP), pancreatic cancer, and/or neuroblastoma.

In some embodiments, the compositions provided herein may be used to treat patients exhibiting pre-cancerous symptoms and thereby prevent the onset of cancer. Target cells and tissues for such preventative treatments include polyps and other precancerous lesions, premalignancies, preneoplastic, or other aberrant phenotype indicating probable progression to a cancerous state. For example, the compositions provided herein may be used to prevent adenomas with little additional toxicities. The Min (multiple intestinal neoplasia) mouse, which shares a mutated APC/apc genotype with FAP, serves as a useful experimental animal model for human FAP patients (Lipkin, 1997). The Min mouse can develop greater than 100 gastrointestinal adenomas/adenocarcinomas throughout the gastrointestinal tract by 120 days of life leading to GI bleeding, obstruction and death. A combination therapy of DFMO and sulindac was shown to be effective in reducing adenomas in these mice. See U.S. Pat. No. 6,258,845, which is incorporated herein by reference in its entirety.

V. FIXED DOSE COMBINATIONS AND ROUTES OF ADMINISTRATION

In one aspect, the present invention provides compositions comprising a fixed dose combination of a pharmaceutically effective amount of eflornithine and a pharmaceutically effective amount of a nonsteroidal anti-inflammatory drug (NSAID) or a metabolite thereof. In some embodiments, the fixed dose combination is a pharmaceutically effective amount of eflornithine and a pharmaceutically effective amount of sulindac.

In some embodiments, the eflornithine is eflornithine hydrochloride monohydrate. In some embodiments, the eflornithine is eflornithine hydrochloride monohydrate racemate. In some embodiments, the eflornithine hydrochloride monohydrate is a racemic mixture of its two enantiomers.

In some embodiments, the eflornithine is present in an amount of about 10 to about 1000 mg. In some embodiments, the eflornithine is present in an amount of about 250 to about 500 mg. In some embodiments, the eflornithine is present in an amount of about 300 to about 450 mg. In some embodiments, the eflornithine is present in an amount of about 350 to about 400 mg. In some embodiments, the eflornithine is present in an amount of about 35 to about 60 weight percent. In some embodiments, the eflornithine is present in an amount of about 40 to about 55 weight percent. In some embodiments, the eflornithine is present in an amount of about 50 to about 55 weight percent. In some embodiments, the eflornithine is present in an amount of about 52 to about 54 weight percent. In some embodiments, the amount of eflornithine hydrochloride monohydrate racemate is from 52 to 54 weight percent. In some embodiments, the eflornithine is present in an amount of about 375 mg. In some embodiments, the amount of eflornithine hydrochloride monohydrate racemate is 375 mg.

In some embodiments, the sulindac is present in an amount from about 10 to about 1500 mg. In some embodiments, the sulindac is present in an amount of about 50 to about 100 mg. In some embodiments, the sulindac is present in an amount of about 70 to about 80 mg. In some embodiments, the sulindac is present in an amount of about 75 mg. In some embodiments, the amount of sulindac is 75 mg. In some embodiments, the sulindac is present in an amount of about 5 to about 20 weight percent. In some embodiments, the sulindac is present in an amount of about 8 to about 15 weight percent. In some embodiments, the sulindac is present in an amount of about 10 to about 12 weight percent. In some embodiments, the amount of sulindac is from 10 to 11 weight percent.

In some embodiments, the eflornithine is present in an amount of about 375 mg and the sulindac is present in an amount of about 75 mg.

In some embodiments, the formulation further comprises an excipient. In some embodiments, the excipient is starch, colloidal silicon dioxide, or silicified microcrystalline cellulose. In some embodiments, the excipient is colloidal silicon dioxide. In some embodiments, the formulation further comprises a second excipient. In some embodiments, the second excipient is silicified microcrystalline cellulose.

In some embodiments, the formulation further comprises a lubricant. In some embodiments, the lubricant is magnesium stearate, calcium stearate, sodium stearate, glyceryl monostearate, aluminum stearate, polyethylene glycol, boric acid or sodium benzoate. In some embodiments, the lubricant is magnesium stearate. In some embodiments, magnesium stearate is present in an amount of about 0.25 to about 2 weight percent. In some embodiments, the amount of magnesium stearate is from about 0.75 to about 2 weight percent. In some embodiments, the amount of magnesium stearate is from about 1 to about 1.5 weight percent. In some embodiments, the amount of magnesium stearate is about 1.1 weight percent. In some embodiments, magnesium stearate is present in an amount of about 1.5 weight percent.

In some embodiments, the compositions are in the form of a capsule, tablet, mini tablets, granules, pellets, solution, gel, cream, foam or patch. In some embodiments, the composition is in the form of a tablet, for example, a monolayer tablet.

In some embodiments, the weight of the tablet is from about 650 mg to about 1,000 mg. In some embodiments, the weight of the tablet is from about 675 mg to about 725 mg. In some embodiments, the weight of the tablet is about 700 mg.

In some embodiments, the tablet further comprises a coating. In some embodiments, the coating is a modified release coating or an enteric coating. In some embodiments, the coating is a pH-responsive coating. In some embodiments, the coating comprises cellulose acetate phthalate (CAP), cellulose acetate trimelletate (CAT), poly (vinyl acetate) phthalate (PVAP), hydroxypropylmethylcellulose phthalate (HP), poly(methacrylate ethylacrylate) (1:1) copolymer (MA-EA), poly(methacrylate methylmethacrylate) (1:1) copolymer (MA MMA), poly(methacrylate methylmethacrylate) (1:2) copolymer, or hydroxypropylmethylcellulose acetate succinate (HPMCAS). In some embodiments, the coating masks the taste of eflornithine. In some embodiments, the coating comprises hydroxypropyl methylcellulose, titanium dioxide, polyethylene glycol, and iron oxide yellow.

In some embodiments, the amount of coating is from about 1 to about 5 weight percent. In some embodiments, the amount of coating is from about 2 to about 4 weight percent. In some embodiments, the amount of coating is about 3 weight percent. In some embodiments, the amount of coating is from about 5 mg to about 30 mg. In some embodiments, the amount of coating is from about 15 mg to about 25 mg. In some embodiments, the amount of coating is about 21 mg.

In some embodiments, the weight of the tablet comprising a coating is from about 675 mg to about 750 mg. In some embodiments, the weight of the tablet comprising a coating is from about 700 mg to about 725 mg. In some embodiments, the weight of the tablet comprising a coating is about 721 mg.

In one aspect, the present invention provides compositions comprising a fixed dose combination of a pharmaceutically effective amount of eflornithine and a pharmaceutically effective amount of sulindac. In some embodiments, the compositions are in the form of a capsule, tablet, mini tablets, granules, pellets, solution, gel, cream, foam or patch. In some embodiments, the compositions are solid and take the form of a tablet, for example, a monolayer tablet. In some embodiments, the tablet is film coated.

In some aspects, the present disclosure provides oral fixed dose combination formulations of eflornithine and an NSAID. In some embodiments, pharmaceutical compositions are provided that comprise a pharmaceutically effective amount eflornithine and a pharmaceutically effective amount of an NSAID. In some embodiments, the NSAID is sulindac, aspirin, piroxicam or celecoxib. In some preferred embodiments, the NSAID is sulindac.

In some embodiments, the pharmaceutical compositions and formulations of the present invention are for enteral, such as oral, and also rectal or parenteral, with the compositions comprising the pharmacologically active compounds either alone or together with pharmaceutical auxiliary substances (excipients). Pharmaceutical preparations for enteral or parenteral administration are, for example, in unit dose forms, such as coated tablets, tablets, capsules or suppositories and also ampoules. These are prepared in a manner, which is known per se, for example using conventional mixing, granulation, coating, solubilizing or lyophilizing processes. Thus, pharmaceutical preparations for oral use can be obtained by combining the active compounds with solid excipients, if desired granulating a mixture which has been obtained, and, if required or necessary, processing the mixture or granulate into tablets or coated tablet cores after having added suitable auxiliary substances. In a preferred embodiment, a mixture of active ingredients and excipients are formulated into a tablet form. Appropriate coatings may be applied to increase palatability or delay absorption. For example, a coating may be applied to a tablet to mask the disagreeable taste of the active compound, such as DFMO, or to sustain and/or to delay the release of the active molecules to a certain area in the gastrointestinal tract.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, or wafers.

In certain embodiments, the tablets and/or capsules provided herein comprise the active ingredients and powdered carriers, such as lactose, starch, cellulose derivatives, magnesium stearate, and stearic acid. Similar diluents can be used to make compressed tablets. In other embodiments, tablets and capsules can be manufactured for immediate or modified release. In some embodiments, the tablet and/or capsule is manufactured as a sustained release product to provide for continuous release of medication over a period of hours. In some embodiments, the compressed tablet is sugar-coated and/or film-coated to mask unpleasant taste and/or protect the tablet from the atmosphere. In some embodiments, the tablet is enteric coated for selective disintegration in the gastrointestinal tract.

In some embodiments, the tablet or capsule is able to disintegrate or dissolve to liberate multiparticulates comprising particles of different populations of a first component and a second component, e.g. modified release coated multiparticles. In some of these embodiments, the tablet or capsule may disintegrate or dissolve in the mouth, stomach, small intestine, terminal ileum, or colon. In some of these embodiments, the tablet or capsule may release the multiparticulates with modified release properties.

In some embodiments, the present invention provides a pharmaceutical oral fixed dose combination in the form of a multilayer tablet. A multilayer tablet has at least two layers (bilayer tablet) or can have three, four, five or more layers. In some embodiments, each of the layers contains not more than one of the active pharmaceutical ingredients (APIs). For example, in some embodiments, the tablet has two layers, with one of the APIs in each of the two layers. In some embodiments, in addition to these two layers, the tablet contains further layers containing only carrier and which may function, e.g., as separation layer(s) or outer coating layer(s). In some embodiments, if more than two layers are present, the components may be present in more than one layer as long as they are not present together in the same layer. In certain embodiments, a monolayer tablet is preferred but all information detailed below is equally applicable to multilayer tablets.

In some embodiments, the fixed dose combination may be formulated to provide a mean steady state plasma concentration level of total eflornithine and/or sulindac in the range of about 0.1 µM to about 1000 µM and preferably in the range of about 1 µM to 100 µM and more preferably in the range of about 1 µM to about 50 µM.

A. Pharmaceutically Acceptable Excipients

In some embodiments, the compositions further comprise a pharmaceutically acceptable excipient. In some of these embodiments, the pharmaceutically acceptable excipient may include a pharmaceutically acceptable diluent, a pharmaceutically acceptable disintegrant, a pharmaceutically acceptable binder, a pharmaceutically acceptable stabilizer, a pharmaceutically acceptable lubricant, a pharmaceutically acceptable pigment, or pharmaceutically acceptable glider. In a fixed dose combination formulation of the present invention, an active ingredient may be mixed at a weight ratio of 1:0.25 to 1:20 with a pharmaceutically acceptable excipient.

Diluents that can be used in pharmaceutical formulations of the present invention include, but are not limited to, microcrystalline cellulose ("MCC"), silicified MCC (e.g. PROSOLV™ HD 90), microfine cellulose, lactose, starch, pregelatinized starch, sugar, mannitol, sorbitol, dextrates, dextrin, maltodextrin, dextrose, calcium carbonate, calcium sulfate, dibasic calcium phosphate dihydrate, tribasic calcium phosphate, magnesium carbonate, magnesium oxide, and any mixtures thereof. Preferably, the diluent is silicified MCC. The diluent may be used in an amount of from about 5 to about 95 weight percent based on the total weight of the formulation, and preferably in an amount of from about 25 to about 40 percent weight, such as in an amount of from about 30 to about 35 percent weight. In certain aspects, the diluent can be a soluble diluent. When the diluent is used, its ratio to the active ingredient in each discrete layer is very important. The term "soluble diluents" refers to a diluent which is dissolved in water, like lactose, Ludipress (BASF, a mixture of lactose, crospovidone and povidone (93:3.5:3.5, w/w (%))), mannitol and sorbitol.

Disintegrants are used to promote swelling and disintegration of the tablet after exposure to fluids in the oral cavity and/or gastrointestinal tract. Examples of disintegrants useful in the fixed dose combination formulation of the present invention include crospovidone, sodium starch glycolate, croscarmellose sodium, low-substituted hydroxypropylcellulose, starch, alginic acid or sodium salt thereof, and a mixture thereof. Other disintegrants that can be used in pharmaceutical formulations of the present invention include, but are not limited to, methylcelluloses, microcrystalline celluloses, carboxymethyl cellulose calcium, carboxymethyl cellulose sodium (e.g. AC-DI-SOL™, PRIMELLOSE™), povidones, guar gum, magnesium aluminum silicate, colloidal silicon dioxide (e.g. AEROSIL™ CARBOSIL™), polacrilin potassium, starch, pregelatinized starch, sodium starch glycolate (e.g. EXPLOTAB™), sodium alginate, and any mixtures thereof. Preferably, the disintegrant is colloidal silicon dioxide. The disintegrant may be used in an amount of about 0.1 to about 30 weight percent based on the total weight of the formulation, and preferably in an amount of about 0.2 to about 5 weight percent.

Compositions of the present invention may comprise lubricants. Sticking can occur when granules attach themselves to the faces of tablet press punches. Lubricants are used to promote flowability of powders, and to reduce friction between the tablet punch faces and the tablet punches and between the tablet surface and the die wall. For example, lubricants include magnesium stearate, calcium stearate, zinc stearate, stearic acid, sodium stearyl fumarate, polyethylene glycol, sodium iauryl sulphate magnesium lauryl sulphate, and sodium benzoate. Preferably, the lubricant is magnesium stearate. In the present invention, lubricants preferably comprise 0.25 weight percent to 2 weight percent of the solid dosage form, and preferably in an amount of about 1.5 weight percent. In an exemplary formulation, the lubricant is magnesium stearate present in an amount of about 1.5 weight percent to prevent sticking.

Binders can be used in the pharmaceutical compositions of the present invention to help hold tablets together after compression. Examples of binders useful for the present invention are acacia, guar gum, alginic acid, carbomers (e.g. Carbopol™ products), dextrin, maltodextrin, methylcelluloses, ethylcelluloses, hydroxyethyl celluloses, hydroxypropyl celluloses (e.g. KLUCEL™), hydroxypropyl methylcelluloses (e.g. METHOCEL™), carboxymethylcellulose sodiums, liquid glucose, magnesium aluminum silicate, polymethacrylates, polyvinylpyrrolidones (e.g., povidone K-90 D, KOLLIDON™) copovidone (PLASDONE™), gelatin, starches, and any mixtures thereof. Preferably, the binder is starch. In the present invention, binders preferably comprise about 1 to about 15 weight percent of the solid dosage form. In other embodiments, the solid dosage form does not comprise a binder.

In certain embodiments, the stabilizer usable in the fixed dose combination formulation of the present invention may be an anti-oxidant. The use of an antioxidant enhances stability of the active ingredients against the undesirable reaction with other pharmaceutically acceptable additives and against modification by heat or moisture with time. For example, the anti-oxidant is ascorbic acid and its esters, butylated hydroxytoluene (BHT), butylated hydroxyanisole (BHA), α-tocopherol, cystein, citric acid, propyl gallate, sodium bisulfate, sodium pyrosulfite, ethylene diamine tetracetic acid (EDTA), and any mixtures thereof.

B. Tablet Manufacture Processes

A further aspect of the present invention is providing processes for the manufacturing tablets disclosed herein, including those comprising eflornithine and sulindac. In some embodiments, active agents are prepared by sifting at least one active agent and one or more excipients through a desired mesh size sieve and then mixing, using a rapid mixer granulator, planetary mixer, mass mixer, ribbon mixer, fluid bed processor, or any other suitable device. The blend can be granulated, such as by adding a solution or suspension with or without a binder, whether alcoholic or hydro-alcoholic or aqueous, in a low or high shear mixer, fluidized bed granulator and the like, or by dry granulation. The granules can be dried using a tray dryer, fluid bed dryer, rotary cone vacuum dryer, and the like. The granules can be sized using an oscillating granulator or comminuting mill or any other conventional equipment equipped with a suitable screen. Alternatively, granules can be prepared by extrusion and spheronization, or roller compaction. Also, the manufacture of granules containing active agents can include mixing with directly compressible excipients or roller compaction.

In other embodiments of the invention, small tablets (mini-tablets) can be made by compressing granules, using dies and punches of various sizes and shapes, as desired. Optionally, a coating can be applied to the tablets, if desired, by techniques known to one skilled in the art such as spray coating, dip coating, fluidized bed coating and the like. In certain embodiments of the present invention, suitable solvent systems such as alcoholic, hydroalcoholic, aqueous, or organic may be used to facilitate processing.

1. Granulation

Granulation is a process in which powder particles are made to adhere to each other, resulting in larger, multiparticle entities or granules. In embodiments of the invention, granules obtained by a dry or wet technique can be blended with one or more lubricants and/or anti-adherants and then filled into single capsule or into different capsules of different sizes, such that a smaller capsule can be filled into another larger capsule.

In certain embodiment, dry granulation by compaction is used for the production of the solid dosage composition. In dry granulation, the powder blend is compacted by applying a force onto the powder, which is general causes a considerable size enlargement. In some aspects, slugging is used in the dry granulation process in which a tablet press is used for the compaction process. In other aspects, a roller compactor is used for dry granulation including a feeding system, compaction unit and size reduction unit. In this method, the powder is compacted between two rolls by applying a force, which is the most important parameter in the dry granulation process. The applied force is expressed in kN/cm, being the force per cm roll width. Occasionally the press force is also indicated in bar. This, however, merely represents the pressure within the hydraulic system, and is in fact not an appropriate measuring unit for the force applied onto the powder. At a given force, depending on the amount of powder conveyed to the rolls, the powder will be compacted to a predefined ribbon thickness.

In other embodiments, wet granulation is used for the production of the solid dosage composition. Wet granulation of powders improves flow and compactability of the compression mix. In wet granulation, granules are formed by the addition of a granulation liquid onto a powder bed, which is under the influence of an impeller (in a high-shear granulator), screws (in a twin screw granulator) or air (in a fluidized bed granulator). The agitation resulting in the system along with the wetting of the components within the formulation results in the aggregation of the primary powder particles to produce wet granules. The granulation liquid (fluid) contains a solvent, which must be volatile so that it can be removed by drying, and be non-toxic. Typical liquids include water, ethanol and isopropanol either alone or in combination. The liquid solution can be either aqueous based or solvent-based. Aqueous solutions have the advantage of being safer to deal with than organic solvents.

Tablets may also be formed by tumbling melt granulation (TMG) essentially as described in Maejima et al, 1997; which is incorporated herein by reference. Tumbling melt granulation can be used for preparing the melt granulation. It can be done in a tumbling mixer. The molten low melting point compound is sprayed on the crystalline saccharide and powdered saccharide in the blender and are mixed until granules form. In this case, the low melting ingredient is the binder and the crystalline saccharide is the seed. An alternative method is to combine the unmelted low melting point ingredient, crystalline sugar (e.g. sucrose or maltose), and water-soluble ingredient in the powder form (e.g., mannitol or lactose) in the tumbling mixer and mix while heating to the melting point of the low melting point binder or higher. The seed should be crystalline or granular water soluble ingredient (saccharide), e.g., granular mannitol, crystalline maltose, crystalline sucrose, or any other sugar. An example of tumbling mixers is the twin-shell blender (V-blender), or any other shape of tumbling mixers. Heating can be achieved by circulating heated air through the chamber of the granulator and by heating the bottom surface of the chamber. As the seed material and the powdered tablet constituents circulate in the heated chamber, the low-melting point compound melts and adheres to the seeds. The unmelted, powdered material adheres to the seed-bound, molten low-melting point material. The spherical beads, which are formed by this process are then cooled and screen sifted to remove nonadhered powder.

Spray congealing or prilling can also be used to form the tablet compositions of the invention. Spray congealing includes atomizing molten droplets of compositions which include a low melting point compound onto a surface or, preferably, other tablet constituents. Equipment that can be used for spray congealing includes spray driers (e.g., Nero spray drier) and a fluid bed coater/granulation with top spray (e.g., Glatt fluid bed coater/granulator). In preferred embodiments, a fast-dissolve granulation is formed wherein, preferably a water soluble excipient, more preferably a saccharide, is suspended in a molten low melting point ingredient and spray congealed. After spray congealing, the resulting composition is allowed to cool and congeal. Following congealing of the mixture, it is screened or sieved and mixed with remaining tablet constituents. Spray congealing processes wherein fast-dissolve granulations comprising any combination of low melting point compound and other tablet constituents are melted and spray congealed onto other tablet constituents are within the scope of the present invention. Spray congealing processes wherein all tablet constituents, including the low-melting point compound, are mixed, the low melting point compound is melted and the mixture is spray congealed onto a surface are also within the scope of the invention.

2. Blending

In certain embodiments, the mixture is blended after granulation. Blending in solid dose manufacturing is to achieve blend uniformity and to distribute the lubricant. In certain aspects, the blend step(s) are designed to achieve homogeneity of all components prior to the final blend of the lubricant. However, blending powders is a challenge due to particle size, moisture content, structure, bulk density and flow characteristics. The key to a successful formula is the order of addition. Typically the component and pharmaceutically acceptable additives are dispatched to a suitable vessel such as a diffusion blender or diffusion mixer. An example of tumbling mixers is the twin-shell blender (V-blender), or any other shape of tumbling mixers.

3. Compression

Once tablet compositions are prepared, they may be formed into various shapes. In preferred embodiments, the tablet compositions are pressed into a shape. This process may comprise placing the tablet composition into a form and applying pressure to the composition so as to cause the composition to assume the shape of the surface of the form with which the composition is in contact. Compression into a tablet form can be accomplished by a tablet press. A tablet press includes a lower punch that fits into a die from the bottom and an upper punch having a corresponding shape and dimension which enters the die cavity from the top after the tableting material falls into the die cavity. The tablet is formed by pressure applied on the lower and upper punches. The tablets of the invention generally have a hardness of about 20 kP or less; preferably the tablets have a hardness of about 15 kP or less. Typical compression pressures are about 5 kN to about 40 kN and will vary based on the desired size and hardness of the tablet. In some aspects, the compression pressure is about 25 kN to about 35 kN. In particular aspects, the compression pressure is less than or about 37 kN, such as less than about 30 kN, such as less than about 25 kN. Hydraulic presses such as a Carver Press or rotary tablet presses such as the Stokes Versa Press are suitable means by which to compress the tablet compositions of the invention. Exemplary compression force parameters are shown in Table 3.

In certain embodiments, the lubricated blend can be compressed using a suitable device, such as a rotary machine to form slugs, which are passed through a mill or fluid energy mill or ball mill or colloid mill or roller mill or hammer mill and the like, equipped with a suitable screen to obtain the milled slugs of actives.

A pre-compression step can be used such as to prevent capping of the tablet. Capping refers to the split or fracture of the cap or top of a tablet from the body of the tablet. Capping can be caused by non-compressible fine particles that migrate when the air is pushed out during compression. For example, the pre-compression can be at about 5, 10 or 15 percent of the main compression force. In preferred embodiments, the tablet is pre-compressed into the form at a pressure, which will not exceed about 10 kN, preferably less than 5 kN. For example, pressing the tablets at less than 1, 1.5, 2, 2.1, 2.2, 2.5, 3, 3.5, 4, 4.5, 5, 6, 7, 8, 9, or 10 kN is within the scope of the invention. In particular aspects, the pre-compression force is about 2.5 kN to about 3.5 kN. Exemplary pre-compression force parameters are shown in Table 3.

4. Film Coating

The composition or solid dosage form according to the invention may also be coated with a film coating, an enteric coating, a modified release coating, a protective coating, or an anti-adhesive coating.

The composition of the invention may be enteric coated. By enteric coated or coating is meant a pharmaceutically acceptable coating preventing the release of the active agent in the stomach and allowing the release in the upper part of the intestinal tract. In other embodiments, the enteric coating is applied to delay the release of the active agent to the terminal ileum or to the colon. The enteric coating may be added as an overcoat upon the modified release coating. The enteric coating polymers can be used either alone or in combination in the enteric coating formulation. Enteric coatings can be designed as a single layer or as multilayer coating embodiments. The preferred enteric coating for the composition of the invention comprises a film-forming agent selected from cellulose acetate phthalate; cellulose acetate trimellitate; methacrylic acid copolymers, copolymers derived from methylacrylic acid and esters thereof, containing at least 40% methylacrylic acid; hydroxypropyl methylcellulose phthalate; hydroxypropylmethylcellulose acetate succinate or Polyvinylacetatephthalate. Examples of polymers suitable for enteric coating include, for example, cellulose acetate phthalate (CAP), cellulose acetate trimelletate (CAT), poly (vinyl acetate) phthalate (PVAP), hydroxypropylmethylcellulose phthalate (HP), poly(methacrylate ethylacrylate) (1:1) copolymer (MA-EA), poly (methacrylate methylmethacrylate) (1:1) copolymer (MA MMA), poly(methacrylate methylmethacrylate) (1:2) copolymer, EUDRAGIT™ L 30D (MA-EA, 1:1), EUDRAGIT™ 100 55 (MA-EA, 3:1), hydroxypropylmethylcellulose acetate succinate (HPMCAS), SURETERIC (PVAP), AQUATERIC™ (CAP), shellac or AQOAT™ (HPMCAS). Targeted colonic delivery systems which may be used with the present invention are known and employ materials such as hydroxypropylcellulose, microcrystalline cellulose (MCE, AVICEL™ from FMC Corp.), poly(ethylene-vinyl acetate) (60:40) copolymer (EVAC from Aldrich Chemical Co.), 2-hydroxyethylmethacrylate (HEMA), MMA, terpolymers of HEMA: MMA: MA synthesized in the presence of N,N'-bis(methacryloyloxyethyloxycarbonylamino)-azobenzene, azopolymers, enteric coated timed release system (TIME CLOCK® from Pharmaceutical Profiles, Ltd., UK) and calcium pectinate and the osmotic minipump system (ALZA corp.).

In some embodiments, the film coating comprises a polymer such as hydroxypropylcellulose (HPC), ethylcellulose (EC), hydroxypropylmethylcellulose (HMPC), hydroxyethylcellulose (HEC), sodium carboxymethylcellulose (CMC), poly(vinyl pyrrolidone) (PVP), poly(ethylene glycol) (PEG), dimethylaminoethyl methacrylate-methacrylic acid ester copolymer, or ethylacrylate-methylmethacrylate copolymer (EA-MMA).

In some embodiments, the composition has a modified release coating. The modified release coating may be a pH-responsive coating which when exposed to a certain pH will deliver the active agent(s) (e.g., to the colorectal tract). In some embodiments, the pH-responsive coating is a pH-responsive polymer that will dissolve when exposed to a pH greater than or equal to about 6; although, the pH-responsive polymer may dissolve at a pH greater than or equal to about 5. The pH-responsive polymer may be, for example, a polymeric compound such as EUDRAGIT™ RS and EUDRAGIT™ RL. The EUDRAGIT™ products form latex dispersions of about 30D by weight. EUDRAGIT™ RS 30D is designed for slow release since it is not very water permeable as a coating and EUDRAGIT™ RS 30D is designed for rapid release since it is relatively water permeable as a coating. These two polymers are generally used in combination. As contemplated herein, the permissible ratios of EUDRAGIT™ RS 30D/EUDRAGIT™ RL 30D is about 10:0 to about 8:2. Ethylcellulose or S100 or other equivalent polymers designed for enteric or colorectal release can also be used in place of the EUDRAGIT™ RS/EUDRAGIT™ RL combination above.

Optionally, the method comprises the step of film coating the tablet. Film coating can be accomplished using any suitable means. Suitable film coatings are known and commercially available or can be made according to known methods. Typically the film coating material is a polymeric film coating material comprising materials such as polyethylene glycol, talc and colorant. Suitable coating materials are methylcellulose, hydroxypropylmethyl-cellulose, hydroxypropylcellulose, acrylic polymers, ethylcellulose, cellulose acetate phthalate, polyvinyl acetate phthalate, hydroxypropyl methylcellulose phthalate, polyvinylalcohol, sodium carboxymethylcellulose, cellulose acetate, cellulose acetate phthalate, gelatin, methacrylic acid copolymer, polyethylene glycol, shellac, sucrose, titanium dioxide, carnauba wax, microcrystalline wax, and zein. In some aspects, the film coating is hydroxypropyl methylcellulose, titanium dioxide, polyethylene glycol, and iron oxide yellow. For example, the film coating is OPADRY® Yellow (Colorcon). Typically, a film coating material is applied in such an amount as to provide a film coating that ranges of from 1% to 6% by weight of the film-coated tablet, such as from 2% to 4%, such as about 3%. Plasticizers and other ingredients may be added in the coating material. The same or different active substance may also be added in the coating material.

In some embodiments, the coating of the tablet can improve palatability such as to mask the disagreeable taste of the active ingredient(s) such as DFMO. For example, the tablet coating composition can include a cellulose polymer, a plasticizer, a sweetener, or a powdered flavor composition, the powdered flavor composition including a flavorant associated with a solid carrier.

C. Administration Schedules and Protocols

In some embodiments, the agent(s) may be administered on a routine schedule. As used herein, a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may be taken orally and that the timing of which is or is not dependent upon food intake. Thus, for example, the agent can be taken every morning and/or every evening, regardless of when the subject has eaten or will eat.

VI. DIAGNOSIS AND TREATMENT OF PATIENTS

In some embodiments, the treatment methods may be supplemented with diagnostic methods to improve the efficacy and/or minimize the toxicity of the anti-cancer therapies comprising administration of the compositions provided herein. Such methods are described, for example, in U.S. Pat. Nos. 8,329,636 and 9,121,852, U.S. Patent Publications US2013/0217743 and US2015/0301060, and PCT Patent Publications WO2014/070767 and WO2015/195120, which are all incorporated herein by reference.

In some embodiments, compositions and formulations of the present disclosure may be administered to a subject with a genotype at position +316 of at least one allele of the ODC1 gene promoter is G. In some embodiments, the genotype at position +316 of both alleles of the patient's ODC1 gene promoters may be GG. In some embodiments, the genotype at position +316 of both alleles of the patient's ODC1 gene promoters may be GA. A statistically significant interaction was detected for ODC1 genotype and treatment in a full model for adenoma recurrence, such that the pattern of adenoma recurrence among placebo patients was: GG 50%, GA 35%, AA 29% versus eflornithine/sulindac patients: GG 11%, GA 14%, AA 57%. The adenomainhibitory effect of eflornithine and sulindac was greater among those with the major G homozygous ODC1 genotype, in contrast to prior reports showing decreased risk of recurrent adenoma among CRA patients receiving aspirin carrying at least one A allele (Martinez et al., 2003; Barry et al., 2006; Hubner et al., 2008). These results demonstrate that ODC1 A allele carriers at position +316 differ in response to prolonged exposure with eflornithine and sulindac compared to GG genotype patients, with A allele carriers experiencing less benefit in terms of adenoma recurrence, and potential for elevated risk of developing ototoxicity, especially among the AA homozygotes.

In some embodiments, the invention provides methods for the preventative or curative treatment of colorectal carcinoma in a patient comprising: (a) obtaining results from a test that determines the patient's genotype at position +316 of at least one ODC1 promoter gene allele; and (b) if the results indicate that the patient's genotype at position +316 of at least one allele of the ODC1 promoter gene is G, then administering to the patient a composition provided herein. In some embodiments, the invention provides methods for the treatment of colorectal carcinoma risk factors in a patient comprising: (a) obtaining results from a test that determines the patient's genotype at position +316 of at least one ODC1 promoter gene allele; and (b) if the results indicate that the patient's genotype at position +316 of at least one allele of the ODC1 promoter gene is G, then administering to the patient a composition provided herein, wherein the methods prevent the formation of new aberrant crypt foci, new adenomatous polyps or new adenomas with dysplasia in the patient. See U.S. Pat. No. 8,329,636, which is incorporated herein by reference.

In some embodiments, the invention provides methods for the preventative or curative treatment of familial adenomatous polyposis (FAP) or neuroblastoma in a patient comprising: (a) obtaining results from a test that determines the patient's genotype at position +316 of at least one ODC1 promoter gene allele; and (b) if the results indicate that the patient's genotype at position +316 of at least one allele of the ODC1 promoter gene is G, then administering to the patient a composition provided herein. In some embodiments, the invention provides methods for the treatment of familial adenomatous polyposis or neuroblastoma risk factors in a patient comprising: (a) obtaining results from a test that determines the patient's genotype at position +316 of at least one ODC1 promoter gene allele; and (b) if the results indicate that the patient's genotype at position +316 of at least one allele of the ODC1 promoter gene is G, then administering to the patient a composition provided herein, wherein the methods prevent the formation of new aberrant crypt foci, new adenomatous polyps or new adenomas with dysplasia in the patient. See U.S. Pat. No. 9,121,852, which is incorporated herein by reference.

In some embodiments, the invention provides methods for treating patients with carcinoma comprising administering to the patients a composition provided herein, wherein the patients have been determined to have a dietary polyamine intake, and/or tissue polyamine level, and/or tissue polyamine flux that is not high. In some of these embodiments, the dietary polyamine intake that is not high is 300 µM polyamine per day or lower. In some of these embodiments, the carcinoma is colorectal cancer. See U.S. Patent Publication US2013/0217743, which is incorporated herein by reference.

In some embodiments, the invention provides methods for the preventative or curative treatment of cancer in a patient comprising: (a) obtaining results from a test that determines an expression level of a let-7 non-coding RNA, a HMGA2 protein, and/or a LIN28 protein in a cancer cell from the patient; and (b) if the results indicate that the patient's cancer exhibits a reduced let-7 non-coding RNA expression level as compared to a reference let-7 non-coding RNA expression level, an elevated HMGA2 protein expression level as compared a reference HMGA2 protein expression level, and/or an elevated LIN28 protein expression level as compared to a reference LIN28 protein expression level, then administering to the patient a composition provided herein. In some of these embodiments, the reference level is a level observed in a non-diseased subject or a level observed in a non-cancerous cell from the patient. In some of these embodiments, "obtaining" comprises providing a sample of the cancer from the patient and assessing an expression level of a let-7 non-coding RNA, an HMGA2 protein, or a LIN28 protein in a cancer cell from the sample. In some of these embodiments, "assessing an expression level of a let-7 non-coding RNA" comprises quantitative PCR or Northern blotting. In some of these embodiments, "assessing an expression level of a HMGA2 protein or a LIN28 protein" comprises immunohistochemistry or ELISA. In some of these embodiments, the sample is blood or tissue, such as tumor tissue. In some of these embodiments, the patient is a human. In some of these embodiments, the cancer is colorectal cancer, neuroblastoma, breast cancer, pancreatic cancer, brain cancer, lung cancer, stomach cancer, a blood cancer, skin cancer, testicular cancer, prostate cancer, ovarian cancer, liver cancer, esophageal cancer, cervical cancer, head and neck cancer, non-melanoma skin cancer, or glioblastoma. In some of these embodiments, the methods further comprise (c) obtaining results from a test that determines the expression of a let-7 non-coding RNA in a second cancer cell from said patient at a second time point following the administration of at least one dose of the ODC inhibitor. In some of these embodiments, the methods further comprise increasing the amount of the ODC inhibitor administered to the patient if no or a small increase in let-7 non-coding RNA is observed. In some of these embodiments, the methods further comprise obtaining results from a test that determines the expression of a HMGA2 protein or a LIN28 protein in a second cancer cell from said patient at a second time point following the administration of at least one dose of the ODC inhibitor. In some of these embodiments, the methods further comprise increasing the amount of the ODC inhibitor administered to the patient if no or a small decrease in HMGA2 protein or LIN28 protein is observed. In some of these embodiments, the methods further comprise (i) obtaining results from a test that determines the patient's genotype at position +316 of at least one allele of the ODC1 gene promoter; and (ii) if the results indicate that the patient's genotype at position +316 of at least one allele of the ODC1 gene promoter is G, then administering to the patient a composition provided herein. In some embodiments, the methods comprise diagnosing a cancer or precancerous condition in a patient comprising obtaining a sample from the patient and (b) determining an expression level of at least two markers selected from the group consisting of a let-7 non-coding RNA, a LIN28 protein, and a HMGA2 protein in the sample, wherein if the expression level of the let-7 non-coding RNA is decreased or the LIN28 protein or HMGA2 protein is increased in the sample relative to a reference level, then the patient is diagnosed as having cancer or a precancerous condition. In some embodiments, the fixed dose combination of the present invention is administered to a patient with a low cell or tissue let-7 level. In other aspects, the present compositions are administered to a patient with a high cell or tissue HMGA2 level. In other aspects, the compositions of the present inventions are administered to a patient with a high cell or tissue LIN28 level. See U.S. Patent Publication US2015/0301060, which is incorporated herein by reference.

In some embodiments, there are provided methods for the preventative or curative treatment of carcinoma in a patient comprising: (a) obtaining results from a test that determines the patient's genotype at position +263 of at least one ODC1 allele; and (b) if the results indicate that the patient's genotype at position +263 of at least one allele of the ODC1 gene is T, then administering to the patient a composition provided herein. In some of these embodiments, the test may determine the nucleotide base at position +263 of one allele of the ODC1 gene in the patient. In some embodiments, the test may determine the nucleotide bases at position +263 of both alleles of the ODC1 gene in the patient. In some embodiments, the results may indicate that the patient's genotype at position +263 of both alleles of the ODC1 gene is TT. In some embodiments, the results may indicate that the patient's genotype at position +263 of both alleles of the ODC1 gene is TG. In some of these embodiments, the method may further comprise obtaining results from a test that determines the patient's genotype at position +316 of at least one ODC1 allele and only administering to the patient of the composition provided herein if the results indicate that the patient's genotype at position +316 of at least one allele of the ODC1 gene is G. In another aspect, there are provided methods for the treatment of colorectal carcinoma risk factors in a patient comprising: (a) obtaining results from a test that determines the patient's genotype at position +263 of at least one ODC1 allele; and (b) if the results indicate that the patient's genotype at position +263 of at least one allele of the ODC1 gene is T, then administering to the patient a composition provided herein, wherein the method prevents the formation of new aberrant crypt foci, new adenomatous polyps or new adenomas with dysplasia in the patient. In another aspect, there is provided methods for preventing the development or recurrence of a carcinoma in a patient at risk therefor comprising: (a) obtaining results from a test that determines the patient's genotype at position +263 of at least one ODC1 allele; and (b) if the results indicate that the patient's genotype at position +263 of at least one allele of the ODC1 gene is T, then administering to the patient a composition provided herein. See PCT Patent Publication WO2015/195120, which is incorporated herein by reference.

In variations on any of the above embodiments, the carcinoma may be colorectal cancer, neuroblastoma, breast cancer, pancreatic cancer, brain cancer, lung cancer, stomach cancer, a blood cancer, skin cancer, testicular cancer, prostate cancer, ovarian cancer, liver cancer, esophageal cancer, cervical cancer, head and neck cancer, non-melanoma skin cancer, or glioblastoma. In some embodiments, the carcinoma may be colorectal cancer. In some embodiments, the colorectal cancer may be stage I. In some embodiments, the colorectal cancer may be stage II. In some embodiments, the colorectal cancer may be stage III. In some embodiments, the colorectal cancer may be stage IV. In variations on any of the above embodiments, the methods may prevent the formation of new advanced colorectal neoplasms within the patient. In some embodiments, the method may prevent the formation of new right-sided advanced colorectal neoplasms. In some embodiments, the method may prevent the formation of new left-sided advanced colorectal neoplasms.

In variations on any of the above embodiments, the patient may have been identified as having one or more adenomatous polyps in the colon, rectum or appendix. In some embodiments, the patient may have been identified as having one or more advanced colorectal neoplasms. In some embodiments, the patient may have been identified as having one or more left-side advanced colorectal neoplasms. In some embodiments, the patient may have been identified as having one or more right-sided advanced colorectal neoplasms. In some embodiments, the patient may have been diagnosed with familial adenomatous polyposis. In some embodiments, the patient may have been diagnosed with Lynch syndrome. In some embodiments, the patient may have been diagnosed with familial colorectal cancer type X. In some embodiments, the patient may satisfy the Amsterdam Criteria or the Amsterdam Criteria II. In some embodiments, the patient may have a history of resection of one or more colorectal adenomas. In some embodiments, the patient may have an intraepithelial neoplasia or a precancerous lesion associated ODC hyperactivity. In some embodiments, the patient may have an intraepithelial neoplasia or a precancerous lesion and elevated cellular polyamine levels.

In variations on any of the above embodiments, the patient is human.

VII. DEFINITIONS

As used herein the specification, "a" or "an" may mean one or more. As used herein in the claim(s), when used in conjunction with the word "comprising," the words "a" or "an" may mean one or more than one.

Throughout this application, the term "about" is used to indicate that a value includes the inherent variation of error for the device, the method being employed to determine the value, or the variation that exists among the study subjects.

As used herein, the term "bioavailability" denotes the degree means to which a drug or other substance becomes available to the target tissue after administration. In the present context, the term "suitable bioavailability" is intended to mean that administration of a composition according to the invention will result in a bioavailability that is improved compared to the bioavailability obtained after administration of the active substance(s) in a plain tablet; or the bioavailability is at least the same or improved compared to the bioavailability obtained after administration of a commercially available product containing the same active substance(s) in the same amounts. In particular, it is desired to obtain quicker and larger and/or more complete uptake of the active compound, and thereby provide for a reduction of the administered dosages or for a reduction in the number of daily administrations.

The terms "compositions," "pharmaceutical compositions," "formulations," and "preparations" are used synonymously and interchangeably herein.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "derivative thereof" refers to any chemically modified polysaccharide, wherein at least one of the monomeric saccharide units is modified by substitution of atoms or molecular groups or bonds. In one embodiment, a derivative thereof is a salt thereof. Salts are, for example, salts with suitable mineral acids, such as hydrohalic acids, sulfuric acid or phosphoric acid, for example hydrochlorides, hydrobromides, sulfates, hydrogen sulfates or phosphates, salts with suitable carboxylic acids, such as optionally hydroxylated lower alkanoic acids, for example acetic acid, glycolic acid, propionic acid, lactic acid or pivalic acid, optionally hydroxylated and/or oxo-substituted lower alkanedicarboxylic acids, for example oxalic acid, succinic acid, fumaric acid, maleic acid, tartaric acid, citric acid, pyruvic acid, malic acid, ascorbic acid, and also with aromatic, heteroaromatic or araliphatic carboxylic acids, such as benzoic acid, nicotinic acid or mandelic acid, and salts with suitable aliphatic or aromatic sulfonic acids or N-substituted sulfamic acids, for example methanesulfonates, benzenesulfonates, p-toluenesulfonates or N-cyclohexylsulfamates (cyclamates).

The term "disintegration" as used herein refers to a process where the pharmaceutical oral fixed dose combination, typically by means of a fluid, falls apart into separate particles and is dispersed. Disintegration is achieved when the solid oral dosage form is in a state in which any residue of the solid oral dosage form, except fragments of insoluble coating or capsule shell, if present, remaining on the screen of the test apparatus is a soft mass having no palpably firm core in accordance with USP<701>. The fluid for determining the disintegration property is water, such as tap water or deionized water. The disintegration time is measured by standard methods known to the person skilled in the art, see the harmonized procedure set forth in the pharmacopeias USP <701> and EP 2.9.1 and JP.

The term "dissolution" as used herein refers to a process by which a solid substance, here the active ingredients, is dispersed in molecular form in a medium. The dissolution rate of the active ingredients of the pharmaceutical oral fixed dose combination of the invention is defined by the amount of drug substance that goes in solution per unit time under standardized conditions of liquid/solid interface, temperature and solvent composition. The dissolution rate is measured by standard methods known to the person skilled in the art, see the harmonized procedure set forth in the pharmacopeias USP <711> and EP 2.9.3 and JP. For the purposes of this invention, the test is for measuring the dissolution of the individual active ingredients is performed following pharmacopoeia USP <711> at the pH as set forth herein for the different embodiments. In particular, the test is performed using a paddle stirring element at 75 rpm (rotations per minute). The dissolution medium is preferably a buffer, typically a phosphate buffer (e.g., at pH 7.2). The molarity of the buffer is preferably 0.1 M.

An "active ingredient" (AI) (also referred to as an active compound, active substance, active agent, pharmaceutical agent, agent, biologically active molecule, or a therapeutic compound) is the ingredient in a pharmaceutical drug or a pesticide that is biologically active. The similar terms active pharmaceutical ingredient (API) and bulk active are also used in medicine, and the term active substance may be used for pesticide formulations.

A "pharmaceutical drug" (also referred to as a pharmaceutical, pharmaceutical preparation, pharmaceutical composition, pharmaceutical formulation, pharmaceutical product, medicinal product, medicine, medication, medicament, or simply a drug) is a drug used to diagnose, cure, treat, or prevent disease. An active ingredient (AI) (defined above) is the ingredient in a pharmaceutical drug or a pesticide that is biologically active. The similar terms active pharmaceutical ingredient (API) and bulk active are also used in medicine, and the term active substance may be used for pesticide formulations. Some medications and pesticide products may contain more than one active ingredient. In contrast with the active ingredients, the inactive ingredients are usually called excipients in pharmaceutical contexts.

The term "effective," as that term is used in the specification and/or claims, means adequate to accomplish a desired, expected, or intended result. "Effective amount," "therapeutically effective amount" or "pharmaceutically effective amount" when used in the context of treating a patient or subject with a compound means that the amount of the compound which, when administered to a subject or patient for treating or preventing a disease, is an amount sufficient to effect such treatment or prevention of the disease.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

An "excipient" is a pharmaceutically acceptable substance formulated along with the active ingredient(s) of a medication, pharmaceutical composition, formulation, or drug delivery system. Excipients may be used, for example, to stabilize the composition, to bulk up the composition (thus often referred to as "bulking agents," "fillers," or "diluents" when used for this purpose), or to confer a therapeutic enhancement on the active ingredient in the final dosage form, such as facilitating drug absorption, reducing viscosity, or enhancing solubility. Excipients include pharmaceutically acceptable versions of antiadherents, binders, coatings, colors, disintegrants, flavors, glidants, lubricants, preservatives, sorbents, sweeteners, and vehicles. The main excipient that serves as a medium for conveying the active ingredient is usually called the vehicle. Excipients may also be used in the manufacturing process, for example, to aid in the handling of the active substance, such as by facilitating powder flowability or non-stick properties, in addition to aiding in vitro stability such as prevention of denaturation or aggregation over the expected shelf life. The suitability of an excipient will typically vary depending on the route of administration, the dosage form, the active ingredient, as well as other factors.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

The term "eflornithine" when used by itself refers to 2,5-diamino-2-(difluoromethyl)pentanoic acid is any of its forms, including non-salt and salt forms (e.g., eflornithine HCl), anhydrous and hydrate forms of non-salt and salt forms (e.g., eflornithine hydrochloride monohydrate), solvates of non-salt and salts forms, its enantiomers (R and S forms, which may also by identified as d and l forms), and mixtures of these enantiomers (e.g., racemic mixture, or mixtures enriched in one of the enantiomers relative to the other). Specific forms of eflornithine include eflornithine hydrochloride monohydrate (i.e., CAS ID: 96020-91-6; MW: 236.65), eflornithine hydrochloride (i.e., CAS ID: 68278-23-9; MW: 218.63), and free eflornithine (i.e., CAS ID: 70052-12-9; MW: 182.17). Where necessary, the form of eflornithine has been further specified. In some embodiments, the eflornithine of the present disclosure is eflornithine hydrochloride monohydrate (i.e., CAS ID: 96020-91-6). The terms "eflornithine" and "DFMO" are used interchangeably herein. Other synonyms of eflornithine and DFMO include: α-difluoromethylornithine, 2-(Difluoromethyl)-DL-ornithine, 2-(Difluoromethyl)ornithine, DL-α-difluoromethylornithine, N-Difluoromethylornithine, ornidyl, αδ-Diamino-α-(difluoromethyl)valeric acid, and 2,5-diamino-2(difluro)pentanoic acid.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

The term "fixed dose combination" or "FDC" refers to a combination of defined doses of two drugs or active ingredients presented in a single dosage unit (e.g., a tablet or a capsule) and administered as such; further as used herein, "free dose combination" refers to a combination of two drugs or active ingredients administered simultaneously but as two distinct dosage units.

"Granulation" refers to the process of agglomerating powder particles into larger granules that contain the active pharmaceutical ingredient. "Dry granulation" refers to any process comprising the steps where there is no addition of a liquid to powdered starting materials, agitation, and drying to yield a solid dosage form. The resulting granulated drug product may be further processed into various final dosage forms, e.g., capsules, tablets, wafers, gels, lozenges, etc.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human patients are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

A "pharmaceutically acceptable carrier," "drug carrier," or simply "carrier" is a pharmaceutically acceptable substance formulated along with the active ingredient medication that is involved in carrying, delivering and/or transporting a chemical agent. Drug carriers may be used to improve the delivery and the effectiveness of drugs, including for example, controlled-release technology to modulate drug bioavailability, decrease drug metabolism, and/or reduce drug toxicity. Some drug carriers may increase the effectiveness of drug delivery to the specific target sites. Examples of carriers include: liposomes, microspheres (e.g., made of poly(lactic-co-glycolic) acid), albumin microspheres, synthetic polymers, nanofibers, nanotubes, protein-DNA complexes, protein conjugates, erythrocytes, virosomes, and dendrimers.

The term "physically separated" as defined herein refers to a pharmaceutical oral fixed dose combination containing both components a) and b) formulated such that they are not mixed with each other in the same carrier but are separated. This separation helps to minimize the interactions between the two components especially upon release of same. Typically the physical separation means that the two components a) and b) are present in different compartments, such as layers, or are present as different entities, such as particulates or granulates, of the formulation. It is not necessary that the two components a) and b) are further separated by additional layers or coating although this may be appropriate from case to case. This physical separation of the two components a) and b) in one dosage form can be achieved by various means known in the art. In one embodiment, this is achieved by formulating the respective components a) and b) into separate layers, e.g., a multi- or bilayer formulation. Specific examples of such formulation techniques are described herein.

The term "sticking" refers to the attachment of granules to the faces of tablet press punches including within the letter, logo or design on the punch faces.

The term "capping" refers to the split or fracture of the cap or top of a tablet from the body of the tablet. Capping can be caused by non-compressible fine particles that migrate when the air is pushed out during compression.

The term "friability" refers herein to the tendency of a tablet to chip, crumble or break following compression. It can be caused by a number of factors including poor tablet design (too sharp edges), low moisture content, insufficient binder, etc. In some aspects, the friability of a tablet sample is given in terms of % weight loss (i.e., loss in weight expressed as a percentage of the original sample weight). Generally, a maximum weight loss of not more than 1% is considered acceptable for most tablets.

The term "release" as used herein refers to a process by which the pharmaceutical oral fixed dose combination is brought into contact with a fluid and the fluid transports the drug(s) outside the dosage form into the fluid that surrounds the dosage form. The combination of delivery rate and delivery duration exhibited by a given dosage form in a patient can be described as its in vivo release profile. The release profiles of dosage forms may exhibit different rates and durations of release and may be continuous. Continuous release profiles include release profiles in which one or more active ingredients are released continuously, either at a constant or variable rate. When two or more components that have different release profiles are combined in one dosage form, the resulting individual release profiles of the two components may be the same or different compared to a dosage form having only one of the components. Thus, the two components can affect each other's release profile leading to a different release profile for each individual component.

A two-component dosage form can exhibit release profiles of the two components that are identical or different to each other. The release profile of a two-component dosage form where each component has a different release profile may be described as "asynchronous". Such a release profile encompasses both (1) different continuous releases where preferably component b) is released at a slower rate than component a), and (2) a profile where one of components a) and b), preferably component b), is released continuous and the other of components a) and b), preferably component a), is modified to be released continuous with a time delay. Also a combination of two release profiles for one drug is possible (e.g. 50% of the drug in continuous and 50% of the same drug continuous with a time delay).

Immediate release: For the purposes of the present application, an immediate release formulation is a formulation showing a release of the active substance(s), which is not deliberately modified by a special formulation design or manufacturing method.

Modified release: For the purposes of the present application, a modified release formulation is a formulation showing a release of the active substance(s), which is deliberately modified by a special formulation design or manufacturing method. This modified release can be typically obtained by delaying the time of release of one or both of the components, preferably component a). Typically for the purposes of the present invention, a modified release refers to a release over 5 h, such as a release over 3 h or even shorter. Modified release as used herein is meant to encompass both a different continuous release over time of the two components or a delayed release where one of the components, preferably component a), is released only after a lag time. Such a modified release form may be produced by applying release-modifying coatings, e.g. a diffusion coating, to the drug substance(s) or to a core containing the drug substance(s), or by creating a release-modifying matrix embedding the drug substance(s).

The term "tablet" refers to a pharmacological composition in the form of a small, essentially solid pellet of any shape. Tablet shapes maybe cylindrical, spherical, rectangular, capsular or irregular. The term "tablet composition" refers to the substances included in a tablet. A "tablet composition constituent" or "tablet constituent" refers to a compound or substance which is included in a tablet composition. These can include, but are not limited to, the active and any excipients in addition to the low melting compound and the water soluble excipient.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

Unit abbreviations used herein include average result (ar), kilopond (kp), kilonewton (kN), percent weight per weight (% w/w), pounds per square inch (psi), RH (relative humidity), color difference delta E (dE), and revolutions per minute (rpm).

VIII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Development of Eflornithine HCl and Sulindac Combination Tables

In the development process of a fixed dose combination (FDC) tablet comprising eflornithine HCl and sulindac, several formulations were tested (Table 1). The parameters that were tested included tablet disintegration time, tablet hardness, and percentage of tablet friability.

Formulation I was manufactured into a 900 mg tablet by first mixing ⅓ of the silicified MCC (PROSOLV®) with the eflornithine HCl in a 1 quart v-blender. Next, the sulindac and ⅓ of the silicified MCC (PROSOLV®) was pre-mixed in a polyethylene (PE) bag and added to the blender along with the colloidal silicon dioxide (CARBOSIL®) and the pregelatinized corn starch (STARCH 1500®). The PE bag was rinsed with the remaining ⅓ of silicified MCC (PROSOLV®) and added to the blender. The mix was blended for 10 minutes at about 25 rpm before the addition of hand screened magnesium stearate and then blended for an additional 3 minutes. This formulation was found to have some sticking on the punch surface and resulted in a rough tablet surface. Thus, for Formulation II the magnesium stearate was increased from 0.5% to 1% and silicified MCC was decreased from 38.57% to 38.07%.

Formulation II was manufactured into a 900 mg tablet by pre-mixing CARBOSIL®, STARCH 1500®, and sulindac in a PE bag. Next, ½ of the PROSOLV® and the eflornithine HCl was added to the 8-quart v-blender along with the pre-mix. The remaining ½ of the PROSOLV® was used to rinse the PE bag and added to the blender. The mix was blended for 10 minutes at about 25 rpm. The mix was then removed from the blender and delumped through a Comill 039R screen before returning to the v-blender for an additional 10 minutes of blending. Next, magnesium stearate hand-screened through a 30 mesh (i.e., 590 μm) screen was added to the v-blender by manual mixing and the mix was blended for 3 minutes at about 25 rpm. The mix was compressed into a tablet on the Key Model BBTS 10 station. The resulting tablet was determined to have a disintegration time of about 29-32 seconds, a friability of 0.077% at 4 minutes and 0.17392% at 8 minutes, and a hardness of about 28 kp (Table 1). The tablet was then film coated with OPADRY® Yellow (Colorcon) at a percent weight of 2.913 to produce a tablet of 927 mg using an O'Hara Labcoat, 12" pan. The film coated tablets had a hardness of about 36.0-42.1 kp and disintegration time of 1 minute 27 seconds to 1 minute 53 seconds.

Formulation III was manufactured into a 650 mg tablet by pre-mixing CARBOSIL®, part 2 of the PROSOLV® and sulindac in a PE bag. Next, ½ of part 1 of the PROSOLV® and eflornithine were added to the 8-quart v-blender with the pre-mix. The remaining ½ of part 1 of the PROSOLV® was used to rinse the PE bag and added to the v-blender. The mix was blended for 10 minutes at about 25 rpm. The mix was then removed from the blender and delumped through a Comill 039R screen before returning to the v-blender for an additional 10 minutes of blending. Next, magnesium stearate hand-screened through a 30 mesh (i.e., 590 µm) screen was added to the v-blender by manual mixing and the mix was blended for 3 minutes at about 25 rpm. The mix was compressed into a tablet on the Key Model BBTS 10 station. The resulting tablet was determined to have a disintegration time of about 51-57 seconds, a friability of 0.2607%-0.3373% at 4 minutes and 0.8988%-1.008% at 8 minutes, and a hardness of about 13 kp. The tablet was then film coated with OPADRY® Yellow (Colorcon) at a percent weight of 2.913 to produce a tablet of 669.5 mg using an O'Hara Labcoat, 12" pan. The film coated tablets had a hardness of about 36.0-42.1 kp and disintegration time of 1 minute 27 seconds to 1 minute 53 seconds. This formulation had a reduced weight from 900 mg to 650 mg and STARCH 1500® was replaced with PROSOLV® to increase the tablet strength. However, capping was observed during the friability testing as well as during the film coating process.

Formulation IV was manufactured into a 700 mg tablet using the same process as Formulation III. The resulting tablet was determined to have a disintegration time of 1 minutes 10 seconds to about 1 minutes 34 seconds, a friability of 0.1424%-0.1567% at 4 minutes and 0.3186%-0.5166% at 8 minutes, and a hardness of about 20 kp. The tablet was then film coated with OPADRY® Yellow (Colorcon) at a percent weight of 2.913 to produce a tablet of 721 mg using an O'Hara Labcoat, 12" pan. The film coated tablets had a disintegration time of 1 minute 43 seconds to 2 minutes 7 seconds. In this formulation, the amount of PROSOLV® was increased and the table weight increased from 650 mg to 700 mg. Although no capping was observed during friability testing, three tablets did have capping during film coating.

TABLE 1

Formulations I-IV of Eflornithine HCL and Sulindac Fixed Dose Combination Tablets.

| Components | Formulation I Unit wt (mg) | Formulation I % W/W | Formulation II Unit wt (mg) | Formulation II % W/W | Formulation III Unit wt (mg) | Formulation III % W/W | Formulation IV Unit wt (mg) | Formulation IV % W/W |
|---|---|---|---|---|---|---|---|---|
| Eflornithine HCl monohydrate racemate | 375 | 41.67 | 375 | 41.67 | 375 | 57.69 | 375 | 53.571 |
| Sulindac | 75 | 8.33 | 75 | 8.33 | 75 | 11.54 | 75 | 10.714 |
| Silicified MCC (part 1) | 347.13 | 38.57 | 342.63 | 38.07 | 149.5 | 23.0 | 199.6 | 28.514 |
| Silicified MCC (part 2) | 0 | 0 | 0 | 0 | 41.075 | 6.32 | 41.075 | 5.868 |
| Pre Gel Corn Starch | 96.12 | 10.68 | 96.12 | 10.68 | 0 | 0 | 0 | 0 |
| Colloidal silicon dioxide | 2.25 | 0.25 | 2.25 | 0.25 | 1.625 | 1.625 | 1.625 | 0.232 |
| Magnesium stearate | 4.5 | 0.5 | 9 | 1 | 7.8 | 7.8 | 7.7 | 1.1 |
| Uncoated Tablet weight | 900 | 100 | 900 | 100 | 650 | 100 | 700 | 100 |
| OPADRY ® Yellow 03B92557 | | | | 27.0 | | 19.5 | | 21.0 |
| Coated Tablet Weight | | | | 927.0 | | 669.5 | | 721.0 |

| | Formulation II | Formulation IV |
|---|---|---|
| Tablet Characteristics | | |
| Compression force | NR | 85 psi |
| Hardness (kp) | ar 28 | ar 20 |
| Disintegration time | ar30 s | ar 1 min 30 s |
| Friability (4 min) (%) | 0.08 | 0.16 |
| Friability (8 min) (%) | 0.17 | 0.52 (one capped tablet) |

TABLE 2

Exemplary Formulation of Eflornithine HCL and Sulindac Fixed Dose Combination Tablet.

| Components | Unit weight (mg) | % (w/w) |
|---|---|---|
| Eflornithine HCl monohydrate racemate | 375.00 | 52.011 |
| Sulindac | 75.00 | 10.402 |
| Silicified microcrystalline cellulose | 237.87 | 32.992 |
| Colloidal silicon dioxide | 1.63 | 0.226 |
| Magnesium stearate | 10.50 | 1.456 |
| Core tablet weight | 700.00 | |
| OPADRY ® Yellow | 21.00 | 2.913 |
| Film coated tablet weight | 721.00 | 100 |

TABLE 3

Exemplary Tablet Manufacture Parameters.

| Variable | 7107/2 R3bis | 7107/2 R4 | 7107/3 | 7107/5 R2 | 7107/5 R3 |
|---|---|---|---|---|---|
| Mixer | Turbula | Turbula | Turbula | Turbula | Turbula |
| Mixing Time | 70 cycles | 70 cycles | 70 cycles | 70 cycles | 70 cycles |
| Mg Stearate | 1.50% | 1.50% | 1.50% | 1.50% | 1.50% |
| Press | Korsch | Korsch | Korsch | Ronchi | Ronchi |
| Tool dimensions | 17.5 × 8 | 17.5 × 8 | 17 × 9 R6 | 16.5 × 7 | 16.5 × 7 |
| Tool Coating | chrome/RC02 | chrome/RC02 | chrome | chrome | chrome |
| Engraving Top | 414C | 414C | neutral | 4141 | 4141 |
| Engraving Bottom | wave logo | wave logo | neutral | logo | logo |
| Scored | no | no | cleavable | cleavable | cleavable |
| Compression Force | 37 or 30 kN | 37 kN | 30 kN | 37 kN | 25 kN |
| Pre-Compression Force | 2.1 kN | 2.5 kN | 2.0 kN | 3.7 kN | 2.5 kN |
| Test Results | | | | | |
| Cleavage | no | no | no | no | no |
| Sticking | no | no | no | no | no |
| Top Engraving Intensity | Pass | Pass | Pass | Pass | Pass |
| Bottom Engraving Intensity | Pass | Pass | Pass | Pass | Pass |
| Hardness | NA | 12.80 kp | 8.14 kp | 18.46 kp | 16.62 kp |
| Cleavaging Ability | NA | yes | yes | no | no |
| Disintegration Time | NA | 1 min 15" to 1 min 25" | 40 sec to 45 sec | 2 min 15" to 2 min 32" | 1 min 39" to 1 min 53" |
| Friability At 4 Minutes | NA | 0.08% | 0.17% | 0.21% | 0.37% |
| Friability At 30 Minutes | NA | 1.15% | 1.19% | 1.80% | 2.85% |
| Tablets Broken/Cleaved | NA | no | no | no | no |

TABLE 4

Materials used for the formulations described in Example 1.

| Material | Supplier |
|---|---|
| Eflornithine HCl monohydrate | Scino Pharm |
| Sulindac | ZACH |
| Silicified microcrystalline cellulose (MCC) (PROSOLV ®) | NF EP |
| Starch 1500 (Partially pregelatinized Maize Starch) | Colorcon Limited |
| Colloidal silicon dioxide (CARBOSIL ®) | IMCD France SAS |
| Magnesium Stearate | Mallinkroot-Tyco |
| OPADRY ® Yellow | Colorcon Limited |

| Equipment |
|---|
| PK blend master V-blender (1 quart and 8 quart) |
| Quadro Comill model 197S with 0.039" screen |
| Key Model BBTS 10 station tableting press |
| O'Hara Labcoat 12" pan, 0.8 mm nozzle |

Example 2—Development of Formulation IV

From Example 1, Formulation IV was further tested to determine which parameters can be altered to prevent capping and sticking. The first parameter tested was the compression force and the addition of a pre-compression force at about 5-15% of the compression force (Table 5). To evaluate the compression and pre-pressure forces for the Formulation IV 700 mg tablet to reach a hardness of about 20 kp, several trials were performed. In a first trial, a final blend of the Formulation IV 700 mg tablet was manufactured using Equipment C (Table 9). The manufacturing process involved pre-mixing CARBOSIL®, part 2 of the PROSOLV® and sulindac in a PE bag. Next, ½ of part 1 of the PROSOLV® and eflornithine were added to a 10-quart v-blender with the pre-mix. The remaining ½ of part 1 of the PROSOLV® was used to rinse the PE bag and added to the v-blender. The mix was blended for 35 minutes at about 7 rpm. The mix was then removed from the blender and delumped through a Frewitt TC150 1.0 mm screen before returning to the v-blender for an additional 35 minutes of blending. Next, magnesium stearate was hand-screened through a 500 μm screen and added to the v-blender by manual mixing for a final blend of 10 minutes at 7 rpm. The compression step was performed on a Courtoy Modul P tableting press equipped with five 17.5×8 mm engraved and chromium plated punches. The parameters were set in order to obtain a hardness of between 17.0 and 22.5 kp. It was found that without pre-pressure, capping was observed. However, the use of a pre-pressure force increased the hardness and avoided capping (Table 10). In addition, the tablets formed with a pre-pressure force were more resistant against attrition (i.e., lower friability). In addition, the 16.5×8 mm punch of the Key BBTS 10 station tableting press used in Example 1 appeared to be more prone to attrition.

TABLE 5

Compression parameters tested for Formulation IV.

| | Initial setting | 107/01 7 setting#3 | 7107/01 setting#2 |
|---|---|---|---|
| Punch shape | 16.5 × 8 mm smooth | 17.5 × 8 mm engraved | 17.5 × 8 mm engraved |
| Compression force | 85 psi | 34 kN | 35 kN |
| Pre-pressure force | No | No | Yes (3 kN) |
| Hardness (kp) | ar 20 | ar 13 (*) | ar 17 |
| Disintegration time | ar 1 min 30 s | ar 1 min 20 sec | ar 2 min |
| Friability (4 min) (%) | 0.16 | 0.07 | 0.03 |
| Friability (8 min) (%) | 0.52 (1 capped tablet) | NA | NA |
| Friability (10 min) (%) | NA | 0.27 | 0.13 |
| Friability (30 min) (%) | NA | 1.79 (1 capped tablet) | 0.54 (no capped tablet) |
| Thickness (mm) | ar 6.1 | ar 5.5 | ar 5.4 |

NA: not applied
(*) maximum hardness that can be reached without precompression.

In a second trial, the punch surface was varied to determine its effect on the Formulation IV tablet (Table 11). The final blend of the Formulation IV 700 mg tablet was manufactured using Equipment B in this trial. The manufacturing process involved pre-mixing CARBOSIL®, part 2 of the PROSOLV® and sulindac in a PE bag. Next, ½ of part 1 of the PROSOLV® and eflornithine were added to a 10-quart v-blender with the pre-mix. The remaining ½ of part 1 of the PROSOLV® was used to rinse the PE bag and added to the v-blender. The mix was blended for 8 minutes 30 seconds at about 30 cycles per minute. The mix was then removed from the blender and delumped through a CMA 1.0 mm screen before returning to the v-blender for an additional 8.5 minutes of blending. Next, magnesium stearate hand-screened through a 500 µm screen and added to the v-blender by manual mixing for a final blend of 2 minutes 20 seconds at 30 cycles per minute. The compression step was performed on a Korsch XL100 tableting press equipped with two 17.5×8 mm engraved and anti-sticking chromium plated punches. The pre-pressure was set at 5-10% of the main compression force which was around 30 kN. Several different punch surfaces were also tested including chromium, carbon, tungsten, and Teflon VS stainless steel. In some embodiments, Teflon may be used to reduce the sticking.

To avoid sticking, several additional variables were tested and a high constraint was applied at the very beginning of the compression. Neither lubrication with 1.1% magnesium stearate nor increasing the lubrication time from 70 rotations to 140 rotations prevented sticking (Tables 11 and 12). However, increasing the ratio of magnesium stearate to 1.5% did prevent sticking (Table 12) along with a slight decrease in tablet hardness at about 20%, but the friability was still very low at less than 0.1% after 4 minutes. With two types of punches, equipped with different kinds of break line (17×9 mm and 16.5×7 mm), breakability results were compliant for both punches tested. Thus, increasing the magnesium stearate to 1.5% prevents sticking and pre-compression prevents capping of Formulation IV.

TABLE 6

Batch weights of Formulation IV in Trial 1 and Trial 2.

| Components | Unit wt (mg) | Trial 1 wt (g) | Trial 2 wt (g) |
|---|---|---|---|
| Eflornithine HCl | 375 | 1339.500 | 1340.000 |
| Sulindac | 75 | 268.100 | 268.027 |
| Silicified MCC (part 1) | 199.6 | 712.800 | 712.000 |
| Silicified MCC (part 2) | 41.075 | 146.700 | 146.648 |
| Colloidal silicon dioxide | 1.625 | 5.796 | 5.8043 |
| Magnesium stearate | 7.7 | 27.515 | 27.504 |
| Tablet weight | 700.0 | 2500.411 | 2499.983 |

TABLE 7

Varying Amounts of Magnesium Stearate for Formulation IV.

| | 1.1% of Magnesium stearate formula | | 1.3% of Magnesium stearate formula (*) | | 1.5% of Magnesium stearate formula (*) | |
|---|---|---|---|---|---|---|
| Components | Unit wt (mg) | w/w (%) | Unit wt (mg) | w/w (%) | Unit wt (mg) | w/w (%) |
| Eflornithine HCl | 375.000 | 53.571 | 374.227 | 53.461 | 373.457 | 53.351 |
| Sulindac | 75.000 | 10.714 | 74.851 | 10.693 | 74.704 | 10.672 |
| Silicified MCC (part 1) | 199.598 | 28.514 | 199.192 | 28.456 | 198.793 | 28.399 |
| Silicified MCC (part 2) | 41.075 | 5.868 | 40.992 | 5.856 | 40.908 | 5.844 |
| Colloidal silicon dioxide | 1.625 | 0.232 | 1.624 | 0.232 | 1.617 | 0.231 |
| Magnesium stearate | 7.700 | 1.100 | 9.100 | 1.300 | 10.500 | 1.500 |
| Tablet weight | 700.0 | 100.00 | 700.0 | 100.00 | 700.0 | 100.00 |

(*) Formulae obtained after dilution to increase the percentage of magnesium stearate. APIs concentration consequently slightly below the target.

TABLE 8

Coating of Formulation IV.

| Components | Unit wt (mg) | Batch wt (g) |
|---|---|---|
| Uncoated tablets | 700.00 | 600.00 |
| OPADRY ® Yellow 03B92557 | 21.00 | 53.995 |
| Purified water | 154.00 | 395.99 |
| Coated Tablet weight | 721.00 | 653.995 |

TABLE 9

Equipment used for development of Formulation IV.

| Equipment A | Equipment B | Equipment C |
|---|---|---|
| PK blend master V-blender | Turbula T10A blender | Servolift blender |
| 1 quart and 8 quart | 10 L container | 10 L container |
| Quadro Comill 197S | CMA T1 conical mill | Frewitt TC150 conical mill |
| 0.039" screen | 1.00 mm screen | 1.00 mm screen |
| | 0.500 mm sieving screen | 0.500 mm sieving screen |

TABLE 9-continued

Equipment used for development of Formulation IV.

| Equipment A | Equipment B | Equipment C |
|---|---|---|
| Key BBTS 10 station tableting press | Korsch XL100 tableting press | Courtoy Modul P tableting press |
| O'Hara Labcoat 12" pan | Mini Glatt coater | |

TABLE 10

First trial parameters and results for testing effect of pre-compression force on Formulation IV.

| | | Compression Parameters | | | |
|---|---|---|---|---|---|
| | | 7107/01 setting#3 | 7107/01 setting#5 | 7107/01 setting#2 | 7107/01 setting#4 |
| Speed (tpm) | | 50 | 50 | 50 | 50 |
| Pre-pressure force (kN)/% of the main pressure | | 0.11/0% | 1.43/5% | 3.25/10% | 4.68/15% |
| Compression force (kN) | | 33.58 | 32.23 | 34.07 | 33.03 |
| Punches (quantity) | | 5 | 5 | 5 | 5 |
| Punch shape | | 17.5 × 8 mm engraved | 17.5 × 8 mm engraved | 17.5 × 8 mm engraved | 17.5 × 8 mm engraved |
| Punch surface treatment | | Anti-sticking chromium plating | Anti-sticking chromium plating | Anti-sticking chromium plating | Anti-sticking chromium plating |

| | | Results | | | |
|---|---|---|---|---|---|
| Test | Sampling | 7107/01 setting#3 | 7107/01 setting#5 | 7107/01 setting#2 | 7107/01 setting#4 |
| Weight (mg) | 20 tablets | 702.28 | 699.14 | 703.5 | 701.17 |
| RSD (%) | | 1.18 | 1.00 | 1.06 | 0.73 |
| Hardness (kp) | 10 tablets | 11.5 to 14.4 (Mean value: 13.2) | 15.2 to 17.9 (Mean value: 16.6) | 15.8 to 18.4 (Mean value: 17.3) | 17.0 to 18.7 (Mean value: 17.9) |
| Friability (%) | According to Pharmacopeia | | | | |
| 4 min | | 0.07/No capping | 0.07/No capping | 0.03/No capping | 0.08/No capping |
| 10 min | | 0.27/No capping | 0.20/No capping | 0.13/No capping | 0.19/No capping |
| 30 min | | 1.79/1 capping | 0.67/No capping | 0.54/No capping | 0.59/No capping |
| Disintegration time (min) | 3 tablets | 1 min 08 sec to 1 min 40 sec | 1 min 39 sec to 2 min 17 sec | 1 min 51 sec to 2 min 11 sec | 1 min 41 sec to 1 min 57 sec |
| Thickness (mm) | 10 tablets | 5.4 to 5.6 | 5.4 to 5.5 | 5.4 to 5.5 | 5.4 to 5.5 |
| Sticking | | Some sticking | Some sticking | Some sticking | Some sticking |

TABLE 11

Second trial parameters and results for testing effect of punch surface on Formulation IV.

| test | sampling | 7107/02 setting#2 | 7107/02 setting#5 | 7107/02 setting#6 | 7107/02 setting#7 | 7107/02 setting#8 |
|---|---|---|---|---|---|---|
| | | Final blend | | | | |
| Ratio of Mg stearate (%) | | 1.1 | 1.1 | 1.1 | 1.1 | 1.1 |
| Final blend (rotations) | | 140 | 140 | 140 | 140 | 140 |
| | | Compression parameters | | | | |
| Speed (tpm) | | 40 | 40 | 40 | 40 | 40 |
| Pre-pressure force (kN) | | 2.5 | 2.2 | 2.2 | 2.1 | 2.1 |
| Compression force (kN) | | 30 | 30 | 30 | 30 | 30 |
| Punches (quantity) | | 2 | 2 | 2 | 2 | 2 |
| Punch shape | | 17.5 × 8 mm engraved | 17.5 × 8 mm engraved | 17.5 × 8 mm engraved | 17.5 × 8 mm engraved | 17.5 × 8 mm engraved |
| Punch surface treatment | | Anti-sticking chromium RC-02 | Anti-sticking with carbon RB-01 | Anti-sticking with tungsten RD-03 | Anti-sticking with teflon RF-03 | Steel (no anti-sticking plating) |
| | | Results | | | | |
| Weight (mg)/RSD (%) | 20 tablets | 697.12/0.38 | NA | NA | NA | NA |
| Hardness (kp) | 5 tablets | 15.4 to 16.3 | NA | NA | NA | NA |
| Friability (%) | According to | 0.02/No capping | NA | NA | NA | NA |

TABLE 11-continued

Second trial parameters and results for testing effect of punch surface on Formulation IV.

| test | sampling | 7107/02 setting#2 | 7107/02 setting#5 | 7107/02 setting#6 | 7107/02 setting#7 | 7107/02 setting#8 |
|---|---|---|---|---|---|---|
| 4 min | Pharmacopeia | 0.04/No capping | | | | |
| 10 min | | 0.69/No capping | | | | |
| 30 min | | | | | | |
| Disintegration time (min) | 3 tablets | 0 min 58 sec to 1 min 00 sec | NA | NA | NA | NA |
| Thickness (mm) | 10 tablets | 5.5 to 5.5 | NA | NA | NA | NA |
| Sticking | 10 tablets | Some sticking | Some sticking | Some sticking | Very slightly sticking | Some sticking |

TABLE 12

Second trial parameters and results for testing effect of final mixing duration and magnesium stearate on Formulation IV.

| test | sampling | 7107/02 setting#1 | 7107/02 setting#2 | 7107/02 setting#3 | 7107/02 setting#4 | 7107/02 setting#10 |
|---|---|---|---|---|---|---|
| | | Final blend | | | | |
| Ratio of Magnesium stearate (%) | | 1.1 | 1.1 | 1.5 | 1.5 | 1.3 |
| Final mixing duration (rotations) | | 70 | 140 | 70 | 70 | 140 |
| | | Compression parameters | | | | |
| Speed (tpm) | | 40 | 40 | 40 | 40 | 40 |
| Pre-pressure force (kN) | | 3.5 | 2.5 | 2.1 | 2.5 | 2.2 |
| Compression force (kN) | | >>30 | 30 | 30 | 37 | 37 |
| Punches (quantity) | | 2 | 2 | 2 | 2 | 2 |
| Punch shape | | 17.5 × 8 mm engraved | 17.5 × 8 mm engraved | 17.5 × 8 mm engraved | 17.5 × 8 mm engraved | 17.5 × 8 mm engraved |
| Punch surface treatment | | Anti-sticking chromium plating | Anti-sticking chromium plating | Anti-sticking chromium plating | Anti-sticking chromium plating | Anti-sticking chromium plating |
| | | Results | | | | |
| Weight (mg)/RSD (%) | 20 tablets | 704.01 (*)/0.23 | 697.12/0.38 | 695.19/0.38 | 702.61/0.39 | 703.24/0.29 |
| Hardness (kp) | 5 tablets | 17.3 to 17.9 | 15.4 to 16.3 | 12.4 to 13.4 | 11.9 to 14.1 | 13.4 to 14.7 |
| Friability (%) | According to | NA | 0.02/No capping | 0.03/No capping | 0.08/No capping | 0.05/No capping |
| 4 min | Pharmacopeia | NA | 0.04/No capping | 0.15/No capping | 0.11/No capping | 0.19/No capping |
| 10 min | | NA | 0.69/No capping | 1.01/No capping | 1.15/No capping | 1.02/ No capping |
| 30 min | | | | | | |
| Disintegration time (min) | 3 tablets | 1 min 15 sec to 1 min 20 sec | 0 min 58 sec to 1 min 00 sec | 1 min 00 sec to 1 min 10 sec | 1 min 15 sec to 1 min 25 sec | 1 min 30 sec to 1 min 45 sec |
| Thickness (mm) | 10 tablets | 5.3 to 5.4 | 5.5 to 5.5 | 5.5 to 5.5 | 5.5 to 5.5 | 5.5 to 5.6 |
| Sticking | 10 tablets | Decreasing of the sticking, some lower punches are clean | Decreasing of the sticking | Very slightly sticking on the upper punches. No sticking on the lower one | No sticking but tendency to split during the hardness test | Slightly sticking on the upper punch |

TABLE 13

Trial parameters and results for testing effect of compression parameters on Formulation IV.

| | 7107/03 setting#1 | 7107/05 setting#1 | 7107/05 setting#2 | 7107/05 setting#3 |
|---|---|---|---|---|
| | Final blend | | | |
| Ratio of Mg stearate (%) | 1.5 | 1.5 | 1.5 | 1.5 |
| | Compression parameters | | | |
| Speed (tpm) | 40 | 40 | 40 | 40 |
| Pre-pressure force (kN) | 2.0 | 5.0 | 3.7 | 2.5 |
| Compression force (kN) | 30 | 24 | 37 | 25 |
| Punches (quantity) | 2 | 2 | 2 | 2 |
| Punch shape | 17 × 9R6 mm breakable | 16.5 × 7 mm breakable | 16.5 × 7 mm breakable | 16.5 × 7 mm breakable |

TABLE 13-continued

Trial parameters and results for testing effect of compression parameters on Formulation IV.

| Punch surface treatment | Anti-sticking chromium | Anti-sticking chromium | Anti-sticking chromium | Anti-sticking chromium |
|---|---|---|---|---|
| | | Results | | |
| test | sampling | 7107/03 setting#1 | 7107/05 setting#1 | 7107/05 setting#2 | 7107/05 setting#3 |

| test | sampling | 7107/03 setting#1 | 7107/05 setting#1 | 7107/05 setting#2 | 7107/05 setting#3 |
|---|---|---|---|---|---|
| Weight (mg)/RSD (%) | 20 tablets | 700.2 0 (*)/0.49 | 705.29/0.59 | 709.62/0.64 | 700.08/0.54 |
| Breaking test RSD on one half (%) | 30 tablets | 0.97 | NA | 3.19 | 2.91 |
| Hardness (kp) | 5 tablets | 7.6 to 8.8 (**) | 18.6 to 19.7 | 17.3 to 19.3 | 16.1 to 16.9 |
| Friability (%) | According to Pharmacopeia | | | | |
| 4 min | | 0.17/No capping | 0.12/No capping | 0.21/No capping | 0.37/No capping |
| 10 min | | 0.32/No capping | 0.47/No capping | 0.51/No capping | 1.04/No capping |
| 30 min | | 1.19/No capping | 1.52/No capping | 1.80/No capping | 2.85/No capping |
| Disintegration time (min) | 3 tablets | 0 min 40 sec to 0 min 45 sec | 1 min 38 sec to 1 min 43 sec | 2 min 15 sec to 2 min 32 sec | 1 min 39 sec to 1 min 53 sec |
| Thickness (mm) | 10 tablets | 5.3 to 5.3 | 6.6 to 6.7 | 6.5 to 6.7 | 6.6 to 6.7 |
| Sticking | 10 tablets | No sticking | No sticking | No sticking | No sticking |

(*) on 30 tablets
(**) on 10 tablets
NA: not applied

The stability of the Formulation IV combination tablet, eflornithine single tablet and sulindac single tablet was tested. Stability analysis of the Formulation IV tablets was performed at 6 months using the Karl Fischer titration method for determination of water content (FIG. 1). In FIG. 1, it is shown that the combination tablet of Formulation IV had a lower uptake of water over six months as compared to the eflornithine single tablet. Water can affect drug potency and drug dissolution; for example, water can increase the rate of drug degradation by hydrolysis (Gerhardt, 2009). Thus, in some embodiments, the combination tablets provided herein are more stable than one or both of the single active agent tablets.

Figure 2B:
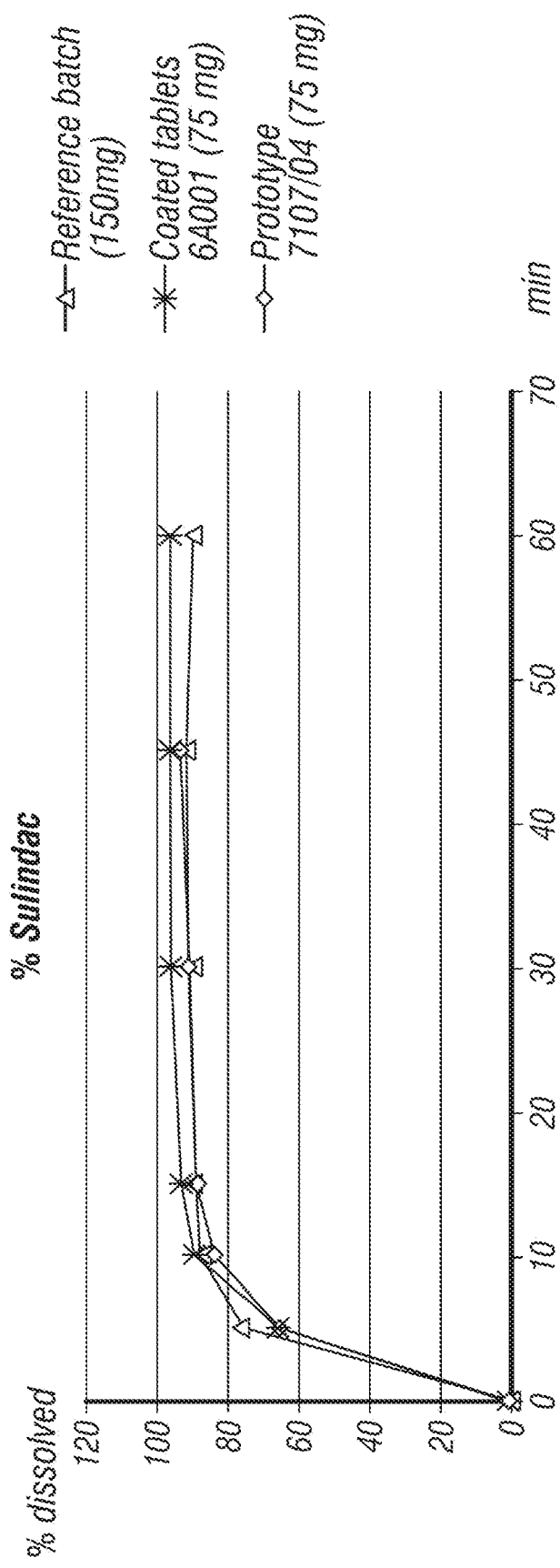
Figure 3:
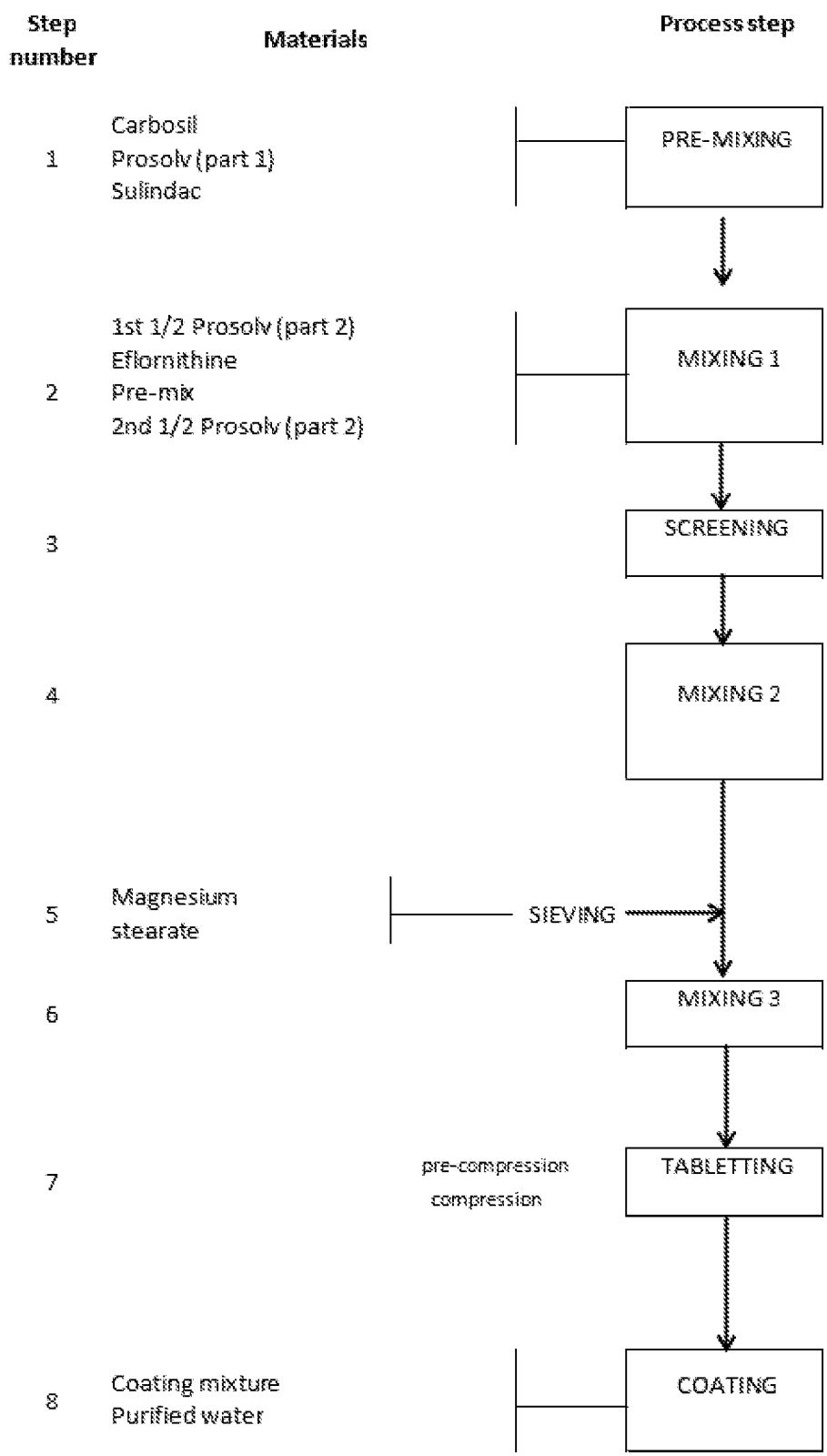
FIG. 3: Simplified scheme depicting a manufacturing process for tablets containing both eflornithine HCl monohydrate and sulindac.

Finally, the dissolution profile of Formulation IV was also tested. The dissolution study was carried out in 50 mM sodium phosphate buffer medium at a pH of 7.2 using a paddle stirring element at 75 rpm (USP <711> Dissolution Apparatus II (Paddle)) (FIGS. 2A-2B). The method was validated level II for the dissolution of elfonithine and sulindac. No interference of active pharmaceutical ingredients eflornithine and sulindac were observed between themselves, with the dissolution medium, with the phosphate buffer solution, or with the excipients. Surprisingly, the fixed dose combination of Formulation IV was observed to have an overlapping in vitro dissolution profile as compared to the single agent tablets.

Example 3—Drug Excipient and Coating Compatibility

A non-cGMP drug excipient compatibility study for eflornithine HCl/sulindac combination tablet was conducted. Appearance, HPLC Assay and XRPD properties were evaluated using a series of samples. The excipients that were tested included PVP, HPMC, lactose, EXPLOTAB™, Ac-Di-Sol®, PROSOLV®, STARCH 1500®, and OPADRY® Yellow. Samples prepared for the excipient compatibility were all 1:1 physical mixtures of API(s) with excipient(s), except the eflornithine HCl:sulindac preparation that was 5:1, and the eflornithine HCl:sulindac:H$_2$O preparation that was about 6:1:0.3. Total mass of most samples was approximately 750 mg. Preparation involved weigh off of components into 20 cc scintillation vials, closed and vortexed for approximately 30 seconds. The samples were then stored in a 40° C./75% RH stability chamber for four weeks. Lids on the vials were loosely secured and were protected from light while stored in the chamber.

Figure 4A:
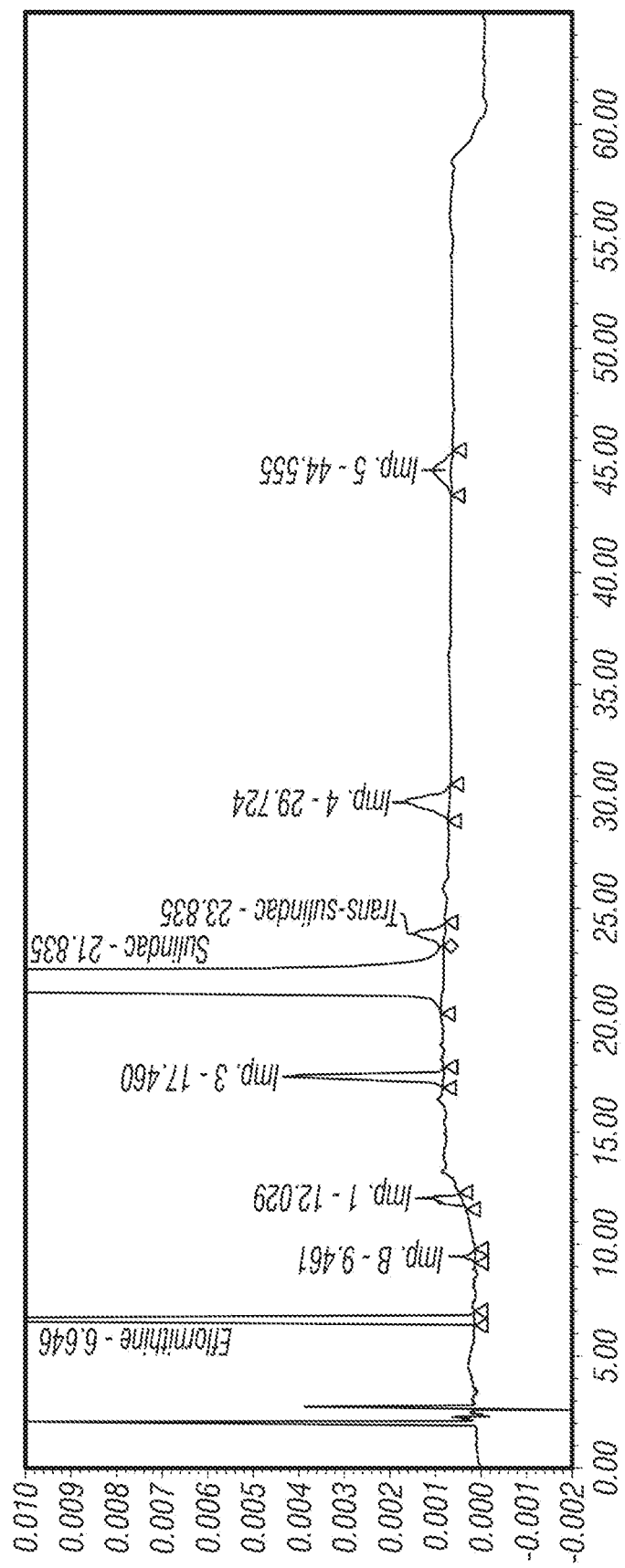
FIGS. 4A-4C: (A) A typical HPLC chromatograph of eflornithine HCl monohydrate and sulindac co-formulated tablet demonstrating the ability to measure selected impurities. (B-C) X-ray powder diffraction (XRPD) patterns of eflornithine HCl monohydrate and sulindac active ingredients mixed with tablet excipients at time zero, 2 weeks, and 4 weeks. The lack of change supports both excipient compatibility and polymorph stability.

Appearance observations were conducted by visual examination of the vials prepared for HPLC analysis. Excipient compatibility samples were extracted with 50% acetonitrile in buffer (50 mM phosphate buffer pH 2.55). Samples containing only Sulindac were prepared by weighing out portion (~150 mg) of the sample and extracted in a pre-determined volume such that the final concentration of eflornithine and sulindac is 9.5 mg/mL and 0.1 mg/mL, respectively. The rest of the compatibility samples were prepared by quantitative transfer using the extraction solvent in a pre-determined volume such that the final concentration of eflornithine and sulindac was approximately the same as above. Excipient compatibility samples were analyzed using a method capable of detecting both actives, eflornithine and sulindac (FIG. 4A). The method employs a gradient reverse phase HPLC with Ultraviolet (UV) detection at 195 nm.

Figure 4B:
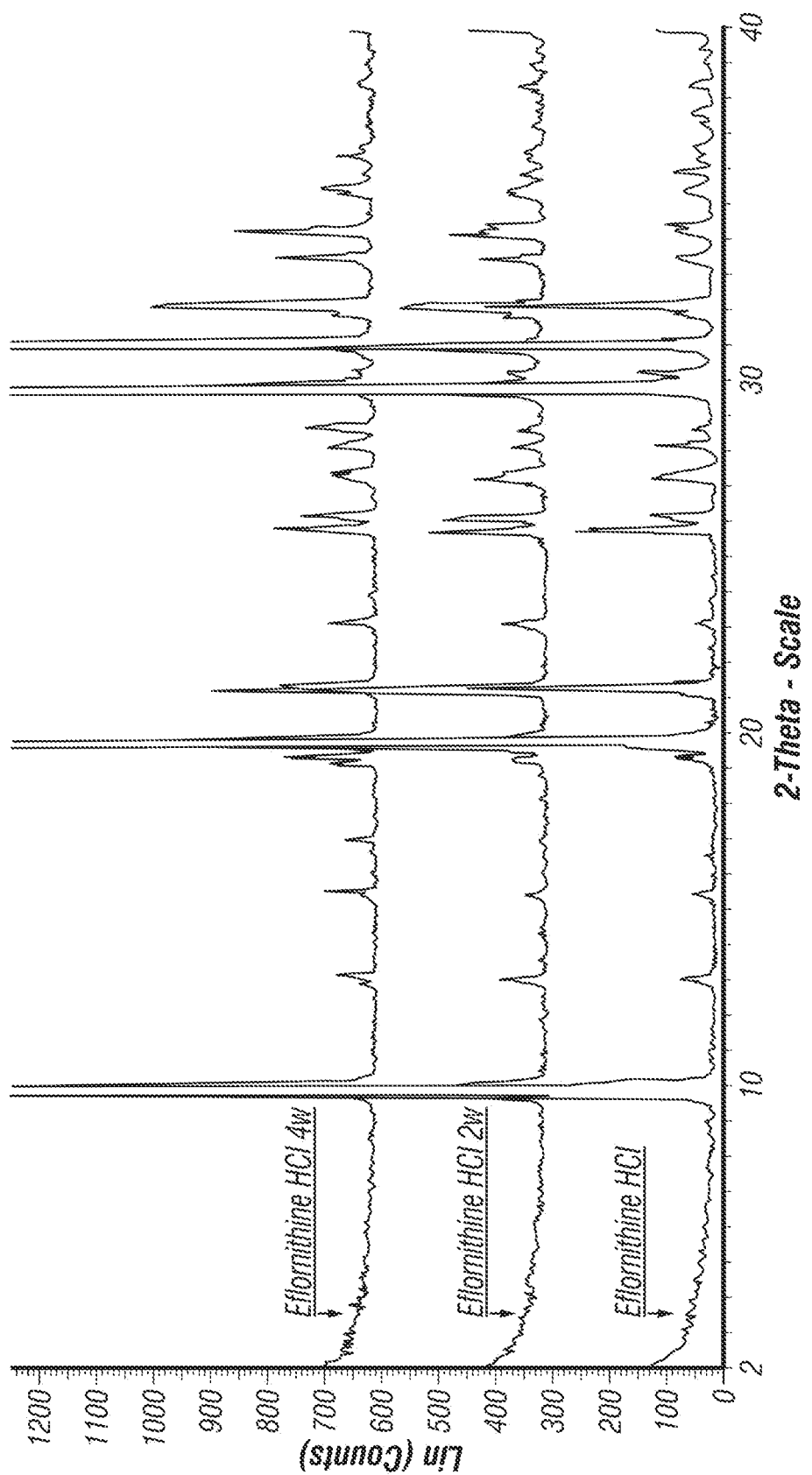
Figure 4C:
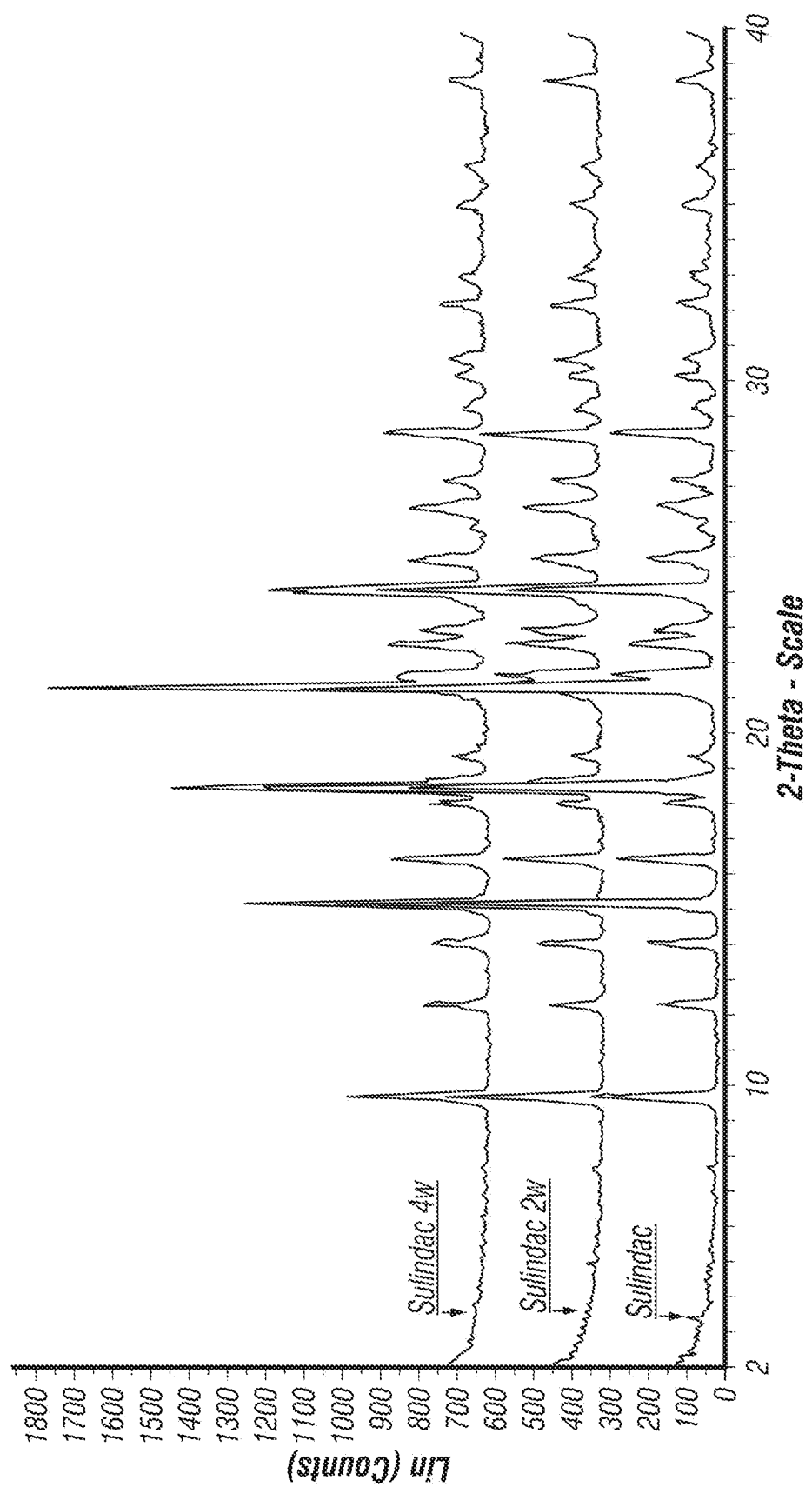

XRPD analysis was conducted on a Bruker AXS D8 Advance system with a Bragg-Brentano configuration using the CuKα radiation. Samples were analyzed at room temperature using the following parameters: 40 kV, 40 mA, 1° divergence and antiscatter slits, a method measuring in continuous mode from 2-40° 2Θ with a 0.05° step and 1 second/step time. Between 3 and 25 mg of sample was analyzed using a rotating, top-filled steel sample holder in a nine-position auto-sampler accessory. The system was calibrated using traceable standards. Results are shown in FIGS. 4B-4C.

Eflomithine HCl with PVP K30 showed moisture in the sample starting in the 2 week sample and becoming a liquid at 4 weeks. Sulindac with PVPK30 showed sticking of the sample at 2 weeks and continuing at 4 weeks. PVPK30 excipient only showed moisture starting in the 2 week sample and becoming a liquid at 4 weeks. The same behavior was observed with the Eflomithine HCl samples but not with the Sulindac samples. HPLC Assay results for the majority of the samples tested show no distinctive trend (increasing or decreasing) over the different time points. Although a number of samples had unusually low assay values, the assay levels showed more of an increasing trend or remain relatively constant over the 4 weeks period. The highest variability in assay results was observed for the Sulindac/Eflomithine ProSolv SMCC90 sample. The assay value at the 4-week time point was 10.0% higher than the assay results at initial. This variability may be contributed to the method (nonvalidated) and sample consistency at the different time points. While the acceptable random analytical error of a validated method is 2%, the variability of this method is unknown. Except for some of the samples, the assay values in each of the samples tested over the different time points are within the normally acceptable 2% random error of an analytical method. There is no distinctive trend for the API, eflornithine and sulindac under the stressed conditions tested. The results of this study suggest that both APIs (eflornithine HCl/sulindac) were compatible with the potential excipients.

The drug excipient compatibility study was conducted by XRPD analysis to determine the crystallinity of the API(s) with potential formulation excipients for eflornithine HCl/sulindac combination product. The XRPD results showed no interaction between the API(s) and excipient at 40° C./75% RH after four weeks. This indicated that both APIs (eflornithine HCl/sulindac) were compatible with the potential excipients.

Coating trials were carried out on tablets to determine effect on stability at 1 month and 3 months at a moisture content of 25° C./60% RH or 40° C./75% RH. The coatings included OPADRY® Yellow (Colorcon, 03B92557), OPADRY® White (Colorcon Y-1-7000), OPADRY® II White (Colorcon 85F18422), and OPADRY® Clear (Colorcon YS-3-7413) at a 3 percent or 4 percent weight gain. The color eye measurement was taken to evaluate the total color difference, or DE, between the tablets that were on stability and the initial coated tablets.

The tablet color was tested using a Datacolor Spectraflash 600 Series Spectrophotometer. The data was analyzed using the Commission Internationale de l'Eclairage (CIE) L* a* b* system. In the L* a* b* system color is represented as a coordinate in a three dimensional space. Lightness and darkness are plotted on the L* axis with L=100 representing pure white and L=0 representing pure black. The a* and b* axes represent the two complementary color pairs of red/green and blue/yellow respectively. By plotting colors geometrically the difference between two colors (total color difference=E*) can be determined by calculating the distance between two points using the following equation.

$$DE^* = [(L^*_1 - L^*_2)^2 + (a^*_1 - a^*_2)^2 + (b^*_1 - b^*_2)^2]^{1/2}$$

Using the Datacolor, each tablet was analyzed at each weight gain of the various coating formulations. The closer the DE value is to zero, the closer the tested tablet color is to the color standard (the initial samples). Colorcon's standard spec for white coatings (to pass QC testing) would be a DE value of less than 1.5. All stability samples with white film coating exceed that 1.5 DE and therefore would not pass Colorcon's standard QC testing (Table 14). The clear coated tablets were also well above the value of 1.5.

TABLE 14

| | \multicolumn{7}{c}{DE values for coated tablets on stability.} | | | | | | |
|---|---|---|---|---|---|---|---|
| | 3% wg Y-1-7000 (white) | 4% wg Y-1-7000 (white) | 3% wg 85F18422 (white) | 4% wg 85F18422 (white) | 3% wg 03B92557 (yellow) | 4% wg 03B92557 (yellow) | 3% wg YS-3-7413 (clear) |
| 1 mo 25/60 | 1.81 | 1.64 | 2.56 | 2.8 | 0.27 | 0.32 | 1.15 |
| 3 mo 25/60 | 1.97 | 1.94 | 2.96 | 2.31 | 0.35 | 0.22 | 1.1 |
| 1 mo 40/75 | 1.91 | 2.47 | 3.58 | 2.39 | 0.3 | 0.29 | 4.29 |
| 3 mo 40/75 | 2.71 | 2.66 | 2.72 | 3.31 | 0.64 | 0.58 | 7.6 |

The best DE results were seen with the tablets coated with the yellow formulation. The DE values were well below 1.5. A DE value (total color difference) of 1 or below is considered imperceptible to the human eye. Colorcon's typical internal specification for yellow coatings tend to be a DE value of 2.5-3. Thus, OPADRY® Yellow was used to coat the combination tablets.

Example 4—Bioequivalence Study of Fixed Co-Formulated Eflornithine/Sulindac

A pilot study was performed to compare the pharmacokinetic parameters of eflornithine, sulindac, sulindac sulfide, and sulindac sulfone in plasma following oral administration of the co-formulated tablet containing eflornithine/sulindac compared to individual tablets containing eflornithine or sulindac taken alone or co-administered in normal healthy subjects under fasting conditions. The secondary objective of this study was to determine the safety and tolerability of eflornithine/sulindac co-formulated tablets compared to individual formulations taken alone or co-administered in normal healthy subjects.

The study comprised twelve subjects, male or female, at least 18 years of age but not older than 60 years. The main inclusion criteria were: light-, non- or ex-smokers; body mass index (BMI)≥18.50 kg/m² and <30.00 kg/m²; no clinically significant abnormality found in the 12-lead ECG performed (subjects had to be in a supine position for 10 minutes prior to ECG, and the ECG was performed prior to all requested blood draws); negative pregnancy test for female subjects; and healthy according to medical history, complete physical examination (including vital signs) and laboratory tests (general biochemistry, hematology and urinalysis).

The subjects were treated in four treatment groups comprising:
  Treatment 1: a single 750/150 mg dose of co-formulated Eflornithine 375 mg/Sulindac 75 mg tablets (2×375/75 mg tablets)
  Treatment 2: a single 750 mg dose of Eflornithine 250 mg tablets (3×250 mg tablets)
  Treatment 3: a single 150 mg dose Sulindac 150 mg tablets (1×150 mg tablet)
  Treatment 4: a single 150 mg dose of Sulindac 150 mg tablets (1×150 mg tablet) and a single 750 mg dose of Eflornithine 250 mg tablets (3×250 mg tablets) administered concurrently Each subject was assigned to receive the 4 different treatments over a 28-day period. A single oral dose of the assigned treatment was administered under fasting conditions in each study period. The treatment administrations were separated by a wash-out of 7 calendar days. A total of 120 blood samples were collected in 80 occasions for each subject. The first blood sample was collected prior to drug administration while the others were collected 0.25, 0.5, 0.75, 1, 1.5, 2, 2.5, 3, 3.5, 4, 5, 6, 8, 10, 12, 16, 24, 36 and 48 hours post drug administration. The analytes were measured by HPLC with MS/MS detection. The assay range was 35.0 ng/mL to 35000.0 ng/mL for eflornithine, 30.0 ng/mL to 15000.0 ng/mL for sulindac, and 10.0 ng/mL to 8000.0 ng/mL for sulindac sulfone and sulindac sulfide. Safety was evaluated through assessment of adverse events (AEs), standard laboratory evaluations, vital signs, and ECGs.

Mathematical Model and Statistical Methods of Pharmacokinetic Parameters:

The main absorption and disposition parameters were calculated using a non-compartmental approach with a log-linear terminal phase assumption. The trapezoidal rule was used to estimate area under the curve. The terminal phase estimation was based on maximizing the coefficient of determination. The pharmacokinetic parameters of this trial were $C_{max}$, $T_{max}$, $AUC_{0-T}$, $AUC_{0-\infty}$, $AUC_{0-T/\infty}$, $\lambda_Z$ and $T_{half}$. The statistical analysis was based on a parametric ANOVA model of the pharmacokinetic parameters; the two-sided 90% confidence interval of the ratio of geometric means for the $C_{max}$, $AUC_{0-T}$ and $AUC_{0-\infty}$ was based on ln-transformed data; the $T_{max}$ was rank-transformed. The ANOVA model used fixed factors of sequence, period, and treatment; the random factor was subject nested within sequence.

The pharmacokinetic parameters included $C_{max}$ (Maximum observed plasma concentration), $T_{max}$ (Time of maximum observed plasma concentration; if it occurs at more than one time point, $T_{max}$ is defined as the first time point with this value), $T_{LQC}$ (Time of last observed quantifiable plasma concentration), $AUC_{0-T}$ (Cumulative area under the plasma concentration time curve calculated from 0 to $T_{LQC}$ using the linear trapezoidal method), $AUC_{0-\infty}$ (Area under the plasma concentration time curve extrapolated to infinity, calculated as $AUC_{0-T}+C_{LQC}/\lambda z$, where $C_{LQC}$ is the estimated concentration at time $T_{LQC}$), $AUC_{0-T/\infty}$ (Relative percentage of $AUC_{0-T}$ with respect to $AUC_{0-\infty}$), $T_{LIN}$ (Time point where log-linear elimination phase begins), $\lambda z$ (Apparent elimination rate constant, estimated by linear regression of the terminal linear portion of the log concentration versus time curve), and $T_{half}$ (Terminal elimination half-life, calculated as $\ln(2)/\lambda z$).

TABLE 15

Pharmacokinetic Parameters for Eflornithine

| PARAMETER | Treatment-1 (n = 12) | | Treatment-2 (n = 12) | | Treatment-4 (n = 12) | |
| --- | --- | --- | --- | --- | --- | --- |
| | MEAN | C.V. (%) | MEAN | C.V. (%) | MEAN | C.V. (%) |
| $C_{max}$(ng/mL) | 10643.8 | (21.6) | 10234.6 | (19.9) | 10012.8 | (25.5) |
| ln ($C_{max}$) | 9.2525 | (2.2) | 9.2134 | (2.3) | 9.1822 | (2.8) |
| $T_{max}$ (hours)* | 3.25 | (2.00-6.00) | 3.50 | (2.00-5.00) | 4.50 | (2.50-5.00) |
| $AUC_{0-T}$ (ng · h/mL) | 71459.8 | (20.4) | 68962.3 | (20.2) | 69914.9 | (18.3) |
| ln ($AUC_{0-T}$) | 11.1562 | (1.9) | 11.1229 | (1.8) | 11.1407 | (1.6) |
| $ALC_{0-\infty}$ (ng · h/mL) | 71839.3 | (20.3) | 69301.2 | (20.0) | 70326.0 | (18.1) |

TABLE 15-continued

Pharmacokinetic Parameters for Eflornithine

| PARAMETER | Treatment-1 (n = 12) | | Treatment-2 (n = 12) | | Treatment-4 (n = 12) | |
|---|---|---|---|---|---|---|
| | MEAN | C.V. (%) | MEAN | C.V. (%) | MEAN | C.V. (%) |
| ln ($AUC_{0-\infty}$) | 11.1619 | (1.9) | 11.1281 | (1.8) | 11.1468 | (1.6) |
| $AUC_{0-T/\infty}$ (%) | 99.44 | (0.3) | 99.48 | (0.2) | 99.39 | (0.3) |
| $\lambda_Z$ (hours$^{-1}$) | 0.1453 | (25.0) | 0.1642 | (21.5) | 0.1630 | (26.3) |
| $T_{half}$ (hours) | 5.07 | (27.3) | 4.43 | (24.9) | 4.65 | (39.0) |

* Median (range)

TABLE 16

Pharmacokinetic Parameters for Sulindac

| PARAMETER | Treatment-1 (n = 12)** | | Treatment-3 (n = 12)** | | Treatment-4 (n = 12)*** | |
|---|---|---|---|---|---|---|
| | MEAN | C.V. (%) | MEAN | C.V. (%) | MEAN | C.V. (%) |
| $C_{max}$ (ng/mL) | 4553.4 | (31.6) | 5236.1 | (39.2) | 5188.5 | (42.9) |
| ln ($C_{max}$) | 8.3788 | (3.7) | 8.4946 | (4.7) | 8.4562 | (5.7) |
| $T_{max}$ (hours)* | 1.54 | (0.75-5.00) | 1.50 | (1.00-2.50) | 1.50 | (0.75-5.00) |
| $AUC_{0-T}$ (ng · h/mL) | 11268.3 | (32.2) | 11569.7 | (31.4) | 11340.8 | (43.9) |
| ln ($AUC_{0-T}$) | 9.2823 | (3.5) | 9.3114 | (3.4) | 9.2621 | (4.2) |
| $AUC_{0-\infty}$ (ng · h/mL) | 11579.4 | (39.9) | 12687.8 | (34.9) | 12023.7 | (49.3) |
| ln ($AUC_{0-\infty}$) | 9.2896 | (4.2) | 9.3924 | (3.9) | 9.3019 | (4.8) |
| $AUC_{0-T/\infty}$ (%) | 96.73 | (4.9) | 98.14 | (1.2) | 97.58 | (1.6) |
| $\lambda_Z$ (hours$^{-1}$) | 0.2810 | (48.0) | 0.3408 | (45.9) | 0.2034 | (58.0) |
| $T_{half}$ (hours) | 4.97 | (142.9) | 2.88 | (83.5) | 4.61 | (55.3) |

*Median (range)
**n = 7 for $AUC_{0-\infty}$, $\lambda_Z$ and $T_{half}$
***n = 8 for $AUC_{0-\infty}$, $\lambda_Z$ and $T_{half}$ Criteria for Bioequivalence:

Statistical inference of eflornithine was to be based on a bioequivalence approach using the ratio of geometric LSmeans with corresponding 90% confidence interval calculated from the exponential of the difference between Treatment 1 vs Treatment 2, Treatment 2 vs Treatment 4 and Treatment 1 vs Treatment 4 for the ln-transformed parameters $C_{max}$, $AUC_{0-T}$ and $AUC_{0-\infty}$ were all to be compared to the 80.00 to 125.00% range. Statistical inference of sulindac was to be based on a bioequivalence approach using the ratio of geometric LSmeans with corresponding 90% confidence interval calculated from the exponential of the difference between Treatment 1 vs Treatment 3, Treatment 3 vs Treatment 4 and Treatment 1 vs Treatment 4 for the ln-transformed parameters $C_{max}$, $AUC_{0-T}$ and $AUC_{0-\infty}$ were all to be compared to the 80.00 to 125.00% range. The same criteria were to be applied for sulindac sulfide and sulindac sulfone and the results were to be presented as supportive evidence of comparable therapeutic outcome.

Safety Results:

A total of 12 subjects entered the study, and all subjects received the 4 treatments under study. No serious adverse events (SAE) and no deaths were reported for any of the subjects enrolled in this study. No subject was withdrawn by the investigator for safety reasons. A total of 4 treatment-emergent adverse events (TEAEs) were reported by 4 (33%) of the 12 subjects who participated in this study. Of these events, 2 occurred after administration Treatment 1, 1 after administration of Treatment 3, and the remaining one after administration of Treatment 4. Subjects dosed with Treatment 2 did not report any TEAEs. Half of the TEAEs experienced during the study were considered related to drug administration.

The TEAEs in this study were experienced with a low incidence; they were experienced by 1 subject (8%) per treatment group. Dry mouth was reported following administration of Treatment 4, upper respiratory tract infection was reported following administration of Treatment 3, and vessel puncture site bruise and headache were each reported following administration of Treatment 1.

The incidence of TEAEs was the same for subjects dosed with Treatment 3 and Treatment 4 (8%) and slightly lower than the one reported for subjects dosed with Treatment 1 (17%). Drug-related TEAEs were reported with the same incidence for subjects dosed with Treatment 1 and Treatment 4 (8%), whereas subjects dosed with Treatment-3 did not experience drug-related TEAEs. The TEAEs experienced during the study were deemed mild (¾, 75%) and moderate (¼, 25%) in intensity. None of the subjects experienced a severe TEAE during the study.

All the abnormal clinical laboratory values were marginally higher or lower than their reference ranges and none were considered clinically significant by the investigator. Furthermore, there were no clinically significant abnormalities in the vital signs and ECGs of the subjects in this study. All physical examinations were judged normal. Overall, the drugs tested were generally safe and well tolerated by the subjects included in this study.

Eflornithine Comparison Between Treatment 1 and Treatment 2:

The pharmacokinetic results demonstrate that the geometric LSmean ratios and the corresponding 90% confidence intervals of $C_{max}$, $AUC_{0-T}$, and $AUC_{0-\infty}$ of eflornithine were all included within the range of 80.00% to 125.00%. The results of this comparison indicate that bioequivalence criteria were met when Treatment 1 and Treatment 2 were administered under fasting conditions and demonstrate that eflornithine bioavailability is comparable between the co-formulated tablet containing eflornithine/sulindac and the tablet containing eflornithine alone.

TABLE 17

Summary of Statistical Analysis of Eflornithine in Treatment 1 vs. Treatment 2

| PARAMETER | INTRA-SUBJECT C.V. (%) | GEOMETRIC LSMEANS * | | RATIO (%) | 90% CONFIDENCE LIMITS (%) | |
|---|---|---|---|---|---|---|
| | | Treatment-1 (n = 12) | Treatment-2 (n = 12) | | LOWER | UPPER |
| $C_{max}$ | 16.8 | 10430.9 | 10030.8 | 103.99 | 92.42 | 117.01 |
| $AUC_{0-T}$ | 13.5 | 69998.7 | 67701.4 | 103.39 | 94.03 | 113.69 |
| $AUC_{0-\infty}$ | 13.4 | 70395.4 | 68056.2 | 103.44 | 94.17 | 113.61 |

* units are ng/mL for $C_{max}$ and ng · h/mL for $AUC_{0-T}$ and $AUC_{0-\infty}$ Eflornithine Comparison Between Treatment 2 and Treatment 4:

The pharmacokinetic results demonstrate that the geometric LSmean ratios and the corresponding 90% confidence intervals of $C_{max}$, $AUC_{0-T}$, and $AUC_{0-\infty}$ of eflornithine were all included within the range of 80.00% to 125.00%. The results of this comparison indicate that bioequivalence criteria were met when Treatment 2 and Treatment 4 were administered under fasted conditions and demonstrate that co-administration of sulindac with the individual tablet of eflornithine did not influence the bioavailability of eflornithine when administered alone.

TABLE 18

Summary of Statistical Analysis of Eflornithine in Treatment 2 vs. Treatment 4

| PARAMETER | INTRA-SUBJECT C.V. (%) | GEOMETRIC LSMEANS * | | RATIO (%) | 90% CONFIDENCE LIMITS (%) | |
|---|---|---|---|---|---|---|
| | | Treatment-2 (n = 12) | Treatment-4 (n = 12) | | LOWER | UPPER |
| $C_{max}$ | 16.8 | 10030.8 | 9722.7 | 103.17 | 91.69 | 116.09 |
| $AUC_{0-T}$ | 13.5 | 67701.4 | 68916.4 | 98.24 | 89.34 | 108.02 |
| $AUC_{0-\infty}$ | 13.4 | 68056.2 | 69338.0 | 98.15 | 89.36 | 107.81 |

* units are ng/mL for $C_{max}$ and ng · h/mL for $AUC_{0-T}$ and $AUC_{0-\infty}$ Eflornithine Comparison Between Treatment 1 and Treatment 4:

The pharmacokinetic results demonstrate that the geometric LSmean ratios and the corresponding 90% confidence intervals of $C_{max}$, $AUC_{0-T}$, and $AUC_{0-\infty}$ of eflornithine were all included within the range of 80.00% to 125.00%. The results of this comparison indicate that bioequivalence criteria were met when Treatment 1 and Treatment 4 were administered under fasted conditions and demonstrate that the bioavailability of eflornithine for the co-formulated tablet containing eflornithine/sulindac and the co-administration of individual tablets containing each eflornithine or sulindac is similar.

Sulindac Comparison Between Treatment 1 Between Treatment 3:

The pharmacokinetic results demonstrate that the geometric LSmean ratios and the corresponding 90% confidence intervals (90CI) of $C_{max}$, $AUC_{0-T}$, and $AUC_{0-\infty}$ of sulindac were not all included within the range of 80.00% to 125.00%. The lower bound of the 90CI of $C_{max}$ was below the 80.00% limit. Since the ratios were within the 80.00% to 125.00% range for all PK parameters, the intra-subject variability could account for the lower bound of $C_{max}$ being outside the BE range. The results obtained for this comparison demonstrate that the sample size used in this pilot study was not sufficient to demonstrate equivalence of sulindac bioavailability from the co-formulated tablet and sulindac alone.

TABLE 19

Summary of Statistical Analysis of Eflornithine in Treatment 1 vs. Treatment 4

| PARAMETER | INTRA-SUBJECT C.V. (%) | GEOMETRIC LSMEANS * | | RATIO (%) | 90% CONFIDENCE LIMITS (%) | |
|---|---|---|---|---|---|---|
| | | Treatment-1 (n = 12) | Treatment-4 (n = 12) | | LOWER | UPPER |
| $C_{max}$ | 16.8 | 10030.8 | 9722.7 | 107.28 | 95.35 | 120.72 |
| $AUC_{0-T}$ | 13.5 | 67701.4 | 68916.4 | 101.57 | 92.37 | 111.68 |
| $AUC_{0-\infty}$ | 13.4 | 68056.2 | 69338.0 | 101.53 | 92.43 | 111.51 |

* units are ng/mL for $C_{max}$ and ng · h/mL for $AUC_{0-T}$ and $AUC_{0-\infty}$

TABLE 20

Summary of the Statistical Analysis of Sulindac in Treatment 1 vs Treatment 3

| PARAMETER | INTRA-SUBJECT C.V. (%) | GEOMETRIC LSMEANS * | | RATIO (%) | 90% CONFIDENCE LIMITS (%) | |
|---|---|---|---|---|---|---|
| | | Treatment-1 (n = 12)** | Treatment-3 (n = 12)** | | LOWER | UPPER |
| $C_{max}$ | 24.6 | 4353.6 | 4888.5 | 89.06 | 75.04 | 105.69 |
| $AUC_{0-T}$ | 11.9 | 10746.4 | 11063.6 | 97.13 | 89.34 | 105.60 |
| $AUC_{0-\infty}$ | 13.6 | 12029.4 | 12743.6 | 94.40 | 82.27 | 108.30 |

* units are ng/mL for $C_{max}$ and ng · h/mL for $AUC_{0-T}$ and $AUC_{0-\infty}$
** n = 7 for $AUC_{0-\infty}$ Based on the data, the intra-subject variation, that incorporates the variability between all comparisons, is about 24.6% for $C_{max}$ and about 12% for $AUC_{0-T}$. Statistically, given that the expected Treatment 1 to Treatment 3 ratio of geometric LSmeans felt within 90 and 110%, it is estimated that the number of subjects to meet the 80.00 to 125.00% bioequivalence range with a statistical a priori power of at least 80% would be about 54 for a future pivotal study. The inclusion of 60 subjects should be sufficient to account for the possibility of drop-outs and variations around the estimated intra-subject CV.

Sulindac Comparison Between Treatment 3 and Treatment 4:

The pharmacokinetic results demonstrate that the geometric LSmean ratios and the corresponding 90% confidence intervals of $C_{max}$, $AUC_{0-T}$, and $AUC_{0-\infty}$ of sulindac were all included within the range of 80.00% to 125.00%. The results of this comparison indicate that bioequivalence criteria were met when Treatment 3 and Treatment 4 were administered under fasted conditions and demonstrate that the co-administration of individual tablets containing eflornithine or sulindac did not influence the bioavailability of sulindac when administered alone.

TABLE 21

Summary of the Statistical Analysis of Sulindac in Treatment 3 vs. Treatment 4

| PARAMETER | INTRA-SUBJECT C.V. (%) | GEOMETRIC LSMEANS * | | RATIO (%) | 90% CONFIDENCE LIMITS (%) | |
|---|---|---|---|---|---|---|
| | | Treatment-3 (n = 12)** | Treatment-4 (n = 12)** | | LOWER | UPPER |
| $C_{max}$ | 24.6 | 4888.5 | 4704.2 | 103.92 | 87.56 | 123.32 |
| $AUC_{0-T}$ | 11.9 | 11063.6 | 10530.9 | 105.06 | 96.63 | 114.22 |
| $ALC_{0-\infty}$ | 13.6 | 12743.6 | 11834.3 | 107.68 | 93.31 | 124.27 |

* units are ng/mL for $C_{max}$ and ng · h/mL for $AUC_{0-T}$ and $AUC_{0-\infty}$
** n = 7 for $AUC_{0-\infty}$ Sulindac Comparison Between Treatment 1 and Treatment 4:

The pharmacokinetic results demonstrate that the geometric LSmean ratios and the corresponding 90% confidence intervals (90CI) of $C_{max}$, $AUC_{0-T}$, and $AUC_{0-\infty}$ of sulindac were not all included within the range of 80.00% to 125.00%. The lower bound of the 90CI of $C_{max}$ was below the 80.00% limit. Since the ratios are within the 80.00% to 125.00% range for all PK parameters, the intra-subject variability could account for the lower bound of $C_{max}$ being outside the BE range. The results obtained for this comparison demonstrate that the sample size used in this pilot study was not sufficient to demonstrate bioequivalence of sulindac bioavailability from the co-formulated tablet and the co-administration of individual tablets containing eflornithine or sulindac.

TABLE 22

Summary of the Statistical Analysis of Sulindac in Treatment 1 vs. Treatment 4

| PARAMETER | INTRA-SUBJECT C.V. (%) | GEOMETRIC LSMEANS * | | RATIO (%) | 90% CONFIDENCE LIMITS (%) | |
|---|---|---|---|---|---|---|
| | | Treatment-1 (n = 12) | Treatment-4 (n = 12) | | LOWER | UPPER |
| $C_{max}$ | 24.6 | 4353.6 | 4704.2 | 92.55 | 77.98 | 109.83 |
| $AUC_{0-T}$ | 11.9 | 10746.4 | 10530.9 | 102.05 | 93.86 | 110.94 |

TABLE 22-continued

Summary of the Statistical Analysis of Sulindac in Treatment 1 vs. Treatment 4

| PARAMETER | INTRA-SUBJECT C.V. (%) | GEOMETRIC LSMEANS * Treatment-1 (n = 12)** | GEOMETRIC LSMEANS * Treatment-4 (n = 12)** | RATIO (%) | 90% CONFIDENCE LIMITS (%) LOWER | 90% CONFIDENCE LIMITS (%) UPPER |
|---|---|---|---|---|---|---|
| $AUC_{0-\infty}$ | 13.6 | 12029.4 | 11834.3 | 101.65 | 88.09 | 117.30 |

\* units are ng/mL for $C_{max}$ and ng · h/mL for $AUC_{0-T}$ and $AUC_{0-\infty}$
\*\*n = 8 for $AUC_{0-\infty}$ Based on the data, the intra-subject variation, that incorporates the variability between all comparisons, is about 24.6% for $C_{max}$ and about 12% for $AUC_{0-T}$. Statistically, given that the expected Treatment 1 to Treatment 4 ratio of geometric LSmeans felt within 92.5 and 107.5%, it is estimated that the number of subjects to meet the 80.00 to 125.00% bioequivalence range with a statistical a priori power of at least 80% would be about 36 for a future pivotal study. The inclusion of 40 subjects should be sufficient to account for the possibility of drop-outs and variations around the estimated intra-subject CV.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,647,858
U.S. Pat. No. 3,654,349
U.S. Pat. No. 4,330,559
U.S. Pat. No. 4,413,141
U.S. Pat. No. 5,814,625
U.S. Pat. No. 5,843,929
U.S. Pat. No. 6,258,845
U.S. Pat. No. 6,428,809
U.S. Pat. No. 6,702,683
U.S. Pat. No. 8,329,636
U.S. Pat. No. 9,121,852
U.S. Patent Publication US2013/0217743
U.S. Patent Publication US2015/0301060
PCT Patent Publication WO2014/070767
PCT Patent Publication WO2015/195120
Alberts et al., *J. Cell. Biochem. Supp.*, (22):18-23, 1995.
AMA Drug Evaluations Annual, 1814-1815, 1994.
Bailey et al., *Cancer Prev Res (Phila)* 3, 35-47, 2010.
Barry et al., *J. Natl. Cancer Inst.*, 98(20):1494-500, 2006.
Bedi et al., *Cancer Res.*, 55(9):1811-1816, 1995.
Bellofernandez et al., *Proc. Natl. Acad. Sci. USA,* 90:7804-8, 1993.
Childs et al., *Cell. Molec. Life Sci.*, 60:1394-1406, 2003.
DuBois et al., *Cancer Res.*, 56:733-737, 1996.
Erdman et al., *Carcinogenesis*, 20:1709-13, 1999.
European Pharmacopoeia, Strasbourg: Council of Europe, $8^{th}$ Ed., 2014.
Fultz and Gerner, *Mol. Carcinog.,* 34:10-8, 2002.
Gerhardt, *Pharmaceutical Processes,* 13(1), 2009.
Gerner et al., *Cancer Epidemoil. Biomarkers Prev.*, 3:325-330, 1994.
Gemer, E. W. & Meyskens, F. L., Jr., *Nat Rev Cancer* 4, 781-92, 2004.
Giardiello et al., *Cancer Res.*, (57):199-201, 1997.
Hanif et al., *Biochemical Pharmacology*, (52):237-245, 1996.
Hubner et al., *Clin. Cancer Res.*, 14(8):2303-9, 2008.
Ignatenko et al., *Cancer Biol. Ther.*, 5(12):1658-64, 2006.
Japanese Pharmacopoeia, Tokyp: Society of Japanese Pharmacopoeia, $16^{th}$ Ed., 2011.
Kingsnorth et al., *Cancer Res.*, 43(9):4035-8, 1983.
Ladenheim et al., *Gastroenterology*, 108:1083-1087, 1995.
Lanza et al., *Arch. Intern. Med.,* 155:1371-1377, 1995.
Lee, Y. S. & Dutta, A., *Genes Dev* 21, 1025-30, 2007.
Lipkin, *J. Cell Biochem.* Suppl., 28-29:144-7, 1997.
Lippman, *Nat. Clin. Pract. Oncol.,* 3(10):523, 2006.
Love et al., *J. Natl. Cancer Inst.,* 85:732-7, 1993.
Luk and Baylin, *N Engl. J. Med.*, 311(2):80-83, 1984.
Lupulescu, *Cancer Detect. Prev.,* 20(6):634-637, 1996.
Maejima et al, *Chemical Pharmacology Bulletin,* 45(3): 518-524, 1997.
Martinez et al., *Proc. Natl. Acad. Sci. USA,* 100:7859-64, 2003.
McLaren et al., *Cancer Prev. Res.,* 1(7):514-21, 2008.
Meyskens et al., *Cancer Prev Res (Phila)* 1, 32-8, 2008.
Meyskens et al., *J. Natl. Cancer Inst.*, 86(15):1122-1130, 1994.
Meyskens et al., *J. Natl. Cancer Inst.*, 90(16):1212-8, 1998.
Muscat et al., *Cancer,* 74:1847-1854, 1994.
Narisawa et al., *Cancer Res.,* 41(5):1954-1957, 1981.
Nigro et al., *Cancer Lett.,* (35):183-8, 1987.
Nowels et al., *Cancer. Biochem. Biophys.,* (8):257-63, 1986.
Pegg, *Biochem.,* 234(2):249-262, 1986.
Physician's Desk Reference, Medical Economics Data, Montville, N.J., 1745-1747, 1999
Piazza et al., *Cancer Res.,* (55):311 3116, 1995.
Piazza et al., *Cancer Res.,* (57):2452-2459, 1997a.
Piazza et al., *Cancer Res.,* (57):2909-2915, 1997b.
Pollard and Luckert, *Cancer Res.,* 49:6471-6473, 1989.
Psaty and Potter, *N Engl. J. Med.,* 355(9):950-2, 2006.
Rao et al., *Cancer Res.,* (55):1464-1472, 1995.
Reddy et al., *Cancer Res.,* (50):2562-2568, 1990.
Reddy et al., *Cancer Res.,* 47:5340-5346, 1987.

Simoneau et al., *Cancer Epidemiol Biomarkers Prev* 17, 292-9, 2008.
Simoneau et al., *J. Natl. Cancer Inst* 93:57-9, 2001.
Singh and Reddy, *Annals. NY Acad Sci.*, (768):205-209, 1995.
Singh et al., *Carcinogenesis*, (15):1317-1323, 1994.
Strejan et al., *Cell Immunol.*, 84(1):171-184, 1984.
Su et al., *Science*, (256):668-670, 1992.
Tempero et al., *Cancer Res.*, 49(21):5793-7, 1989.
Thomas and Thomas, *J. Cell Mol. Med.*, 7:113-26, 2003.
Thompson et al., *Cancer Res*, (45):1170-3, 1985.
Thompson et al., *J. Natl. Cancer Inst.*, (87):125-1260, 1995.
United States Pharmacopeia and National Formulary (USP 39-NF 34). Rockville, Md.; 2015.
Vander Heiden, M. G. *Nat Rev Drug Discov* 10, 671-84, 2011.
Vane and Botting, *Adv Exp Med Biol.*, 433:131-8, 1997.
Wallace, *Eur. J. Clin. Invest.*, 30:1-3, 2000.
Wang et al., *Clin Cancer Res* 17, 2570-80, 2011.
Weeks et al., *Proc. Nat'l Acad. Sci. U.S.A.*, (79):6028-32, 1982.
Zell et al., *Cancer Prev. Res.*, 2(3):209-12, 2009.
Zhang et al., *Genes Dev* 26, 461-73, 2012.

What is claimed is:

1. A composition comprising a fixed dose combination in a single dosage unit of (a) about 375 mg eflornithine hydrochloride monohydrate, which corresponds to a quantity of about 289 mg of eflornithine in its anhydrous, free base form, and (b) about 75 mg of sulindac, wherein the composition further comprises magnesium stearate in an amount of about 1.5 weight percent.

2. The composition of claim 1, wherein the eflornithine hydrochloride monohydrate is a racemic mixture of its two enantiomers.

3. The composition of claim 2, wherein the amount of eflornithine hydrochloride monohydrate racemate is 375 mg.

4. The composition of claim 1, wherein the amount of sulindac is 75 mg.

5. The composition of claim 1, further comprising an excipient.

6. The composition of claim 5, wherein the excipient is starch, colloidal silicon dioxide, or silicified microcrystalline cellulose.

7. The composition of claim 5, wherein the excipient is colloidal silicon dioxide.

8. The composition of claim 7, wherein the composition further comprises a second excipient.

9. The composition of claim 8, wherein the second excipient is silicified microcrystalline cellulose.

10. The composition of claim 1, wherein the composition is in the form of a capsule, tablet, mini-tablet, granule, pellet, solution, gel, cream, foam, or patch.

11. The composition of claim 10, wherein the composition is in the form of a tablet.

12. The composition of claim 11, wherein the weight of the tablet is from about 675 mg to about 725 mg.

13. The composition of claim 12, wherein the weight of the tablet is about 700 mg.

14. The composition of claim 11, wherein the tablet further comprises a coating.

15. The composition of claim 14, wherein the coating masks the taste of eflornithine.

16. The composition of claim 14, wherein the coating comprises hydroxypropyl methylcellulose, titanium dioxide, polyethylene glycol, and iron oxide yellow.

17. The composition of claim 14, wherein the amount of coating is from about 2 to about 4 weight percent.

18. The composition of claim 14, wherein the weight of the tablet is from about 700 mg to about 725 mg.

19. The composition of claim 18, wherein the weight of the tablet is about 721 mg.

20. A method of producing the tablet of claim 11 comprising:
 (a) pre-mixing sulindac and an excipient to form a first mixture;
 (b) mixing the first mixture with a second mixture comprising eflornithine and an excipient to form a blend;
 (c) screening the blend to form a granulated blend;
 (d) adding a lubricant to the granulated blend to obtain a final blend; and
 (e) applying a compression force to the final blend to form the tablet.

21. The method of claim 20, further comprising a pre-compression step after step (d) and prior to step (e), wherein the blend is compressed with a force lower than the force of step (e) to form a pre-compressed blend, further wherein the compression force of step (e) then acts on the pre-compressed blend to form the tablet.

22. The method of claim 21, wherein the pre-compression step prevents tablet capping.

23. The method of claim 21, wherein a compression force of the pre-compression step is applied at about 5 to about 15 percent of the compression force applied in step (e).

* * * * *